(12) United States Patent
Yang et al.

(10) Patent No.: US 10,287,291 B2
(45) Date of Patent: May 14, 2019

(54) SECO-CYCLOPROPAPYRROLOINDOLE COMPOUNDS, ANTIBODY-DRUG CONJUGATES THEREOF, AND METHODS OF MAKING AND USE

(71) Applicants: BRISTOL-MYERS SQUIBB COMPANY, Princeton, NJ (US); THE SCRIPPS RESEARCH INSTITUTE, La Jolla, CA (US)

(72) Inventors: Fukang Yang, Madison, CT (US); Qian Zhang, Danville, CA (US); Lawrence B. Snyder, Killingworth, CT (US); Sanjeev Gangwar, Foster City, CA (US); Dale L. Boger, La Jolla, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/680,424

(22) Filed: Aug. 18, 2017

(65) Prior Publication Data

US 2018/0051031 A1 Feb. 22, 2018

Related U.S. Application Data

(60) Provisional application No. 62/377,052, filed on Aug. 19, 2016.

(51) Int. Cl.
| | | |
|---|---|---|
| *C07D 487/04* | (2006.01) | |
| *C07D 519/00* | (2006.01) | |
| *A61K 31/407* | (2006.01) | |
| *A61K 31/437* | (2006.01) | |
| *A61K 47/68* | (2017.01) | |
| *A61P 35/00* | (2006.01) | |
| *A61K 39/00* | (2006.01) | |

(52) U.S. Cl.
CPC .......... *C07D 487/04* (2013.01); *A61K 31/407* (2013.01); *A61K 39/0011* (2013.01); *A61K 47/6803* (2017.08); *A61K 47/6851* (2017.08); *A61K 47/6857* (2017.08); *A61K 47/6863* (2017.08); *A61P 35/00* (2018.01); *C07D 519/00* (2013.01)

(58) Field of Classification Search
CPC ...... C07D 487/04; A61K 31/407; A61P 35/00
USPC ............... 544/111; 548/429; 514/231.5, 411, 514/231.6
See application file for complete search history.

(56) References Cited

U.S. PATENT DOCUMENTS

| | | |
|---|---|---|
| 6,281,354 B1 | 8/2001 | Boger |
| 6,548,530 B1 | 4/2003 | Boger |
| 7,129,261 B2 | 10/2006 | Ng et al. |
| 7,507,420 B2 | 3/2009 | Ng et al. |
| 7,655,660 B2 | 2/2010 | Zhao et al. |
| 7,968,586 B2 | 6/2011 | Gangwar et al. |
| 8,034,959 B2 | 10/2011 | Ng et al. |
| 8,461,117 B2 | 6/2013 | Sufi et al. |
| 8,664,407 B2 | 3/2014 | Chen et al. |
| 8,852,599 B2 | 10/2014 | Zhang et al. |
| 2008/0279868 A1 | 11/2008 | Boyd et al. |

FOREIGN PATENT DOCUMENTS

WO WO 2016/193709 A1 12/2016

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Boger, et al., "Reversed and Sandwiched Analogs of Duocarmycin SA: Establishment of the Origin of the Sequence-Selective Alkylation of DNA and New Insights into the Source of Catalysis" Journal of The American Chemical Society, vol. 119, pp. 4987-4998, 1997.
Boger, et al., "Synthesis of N-(Tert-Butyloxycarbonyl)-CBI, CBI, . . . ," J. Org. Chem., vol. 55, pp. 5823-5832, 1990.
Boger, et al., "Synthesis and Evaluation of 1,2,8,8a-Tetrahydrocyclopropa[c]Pyrrolo[3,2-e] indol-4(5H)-one, the . . . ," J. Org. Chem., vol. 65: pp. 4101-4111, 2000.
Boger and Johnson, "CC-1065 and the Duocarmycins: Unraveling the Keys to a New Class of Naturally Derived DNA Alkylating Agents," Proc. Natl. Acad. Sci., vol. 92, pp. 3642-3649, 1995.
Boger, et al., "CBI Prodrug Analogs CC-1065 and the Duocarmycins," Synthesis, No. SI, pp. 1505-1509, 1999.
Chari, et al., "Enhancement of the Selectivity and Antitumor Efficacy of a CC-1065 Analogue Through Immunoconjugate Formation," Cancer Research, vol. 55, pp. 4079-4084, 1995.
Ducry, et al., "Antibody-Drug Conjugates: Linking Cytotoxic Payloads to Monoclonal Antibodies," Bioconjugate Chem, vol. 21, pp. 5-13, 2010.

(Continued)

Primary Examiner — Venkataraman Balasubramanian
(74) Attorney, Agent, or Firm — Yuan Chao

(57) ABSTRACT seco-Cyclopropapyrroloindole compounds of formula (I)

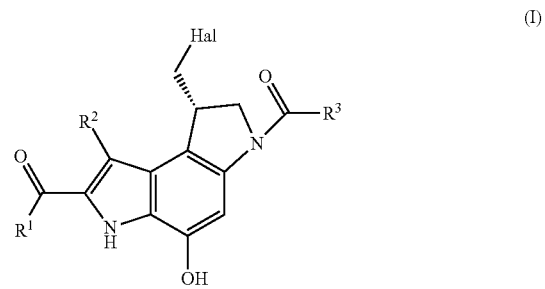

Figure 1A:
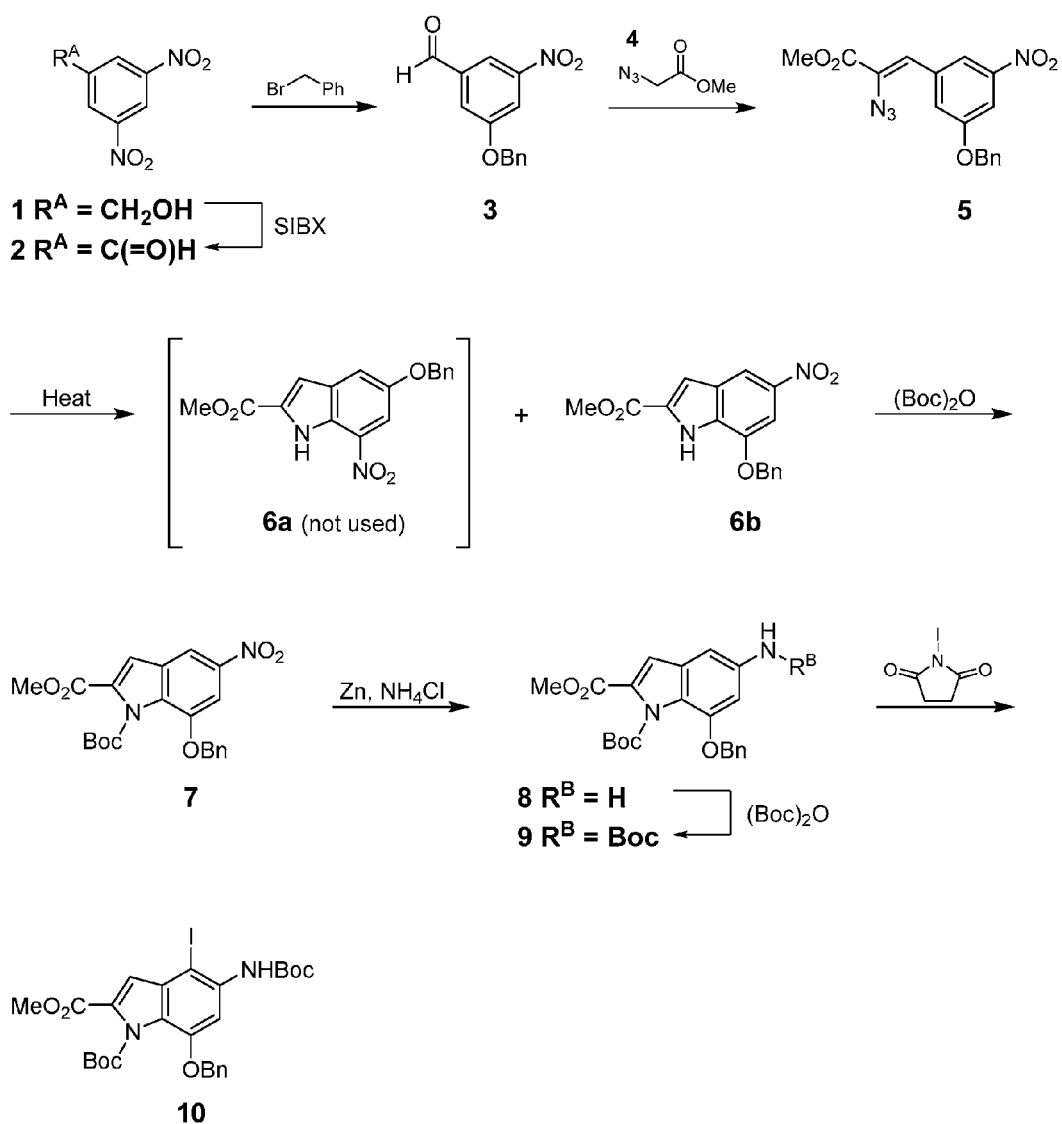
Figure 1B:
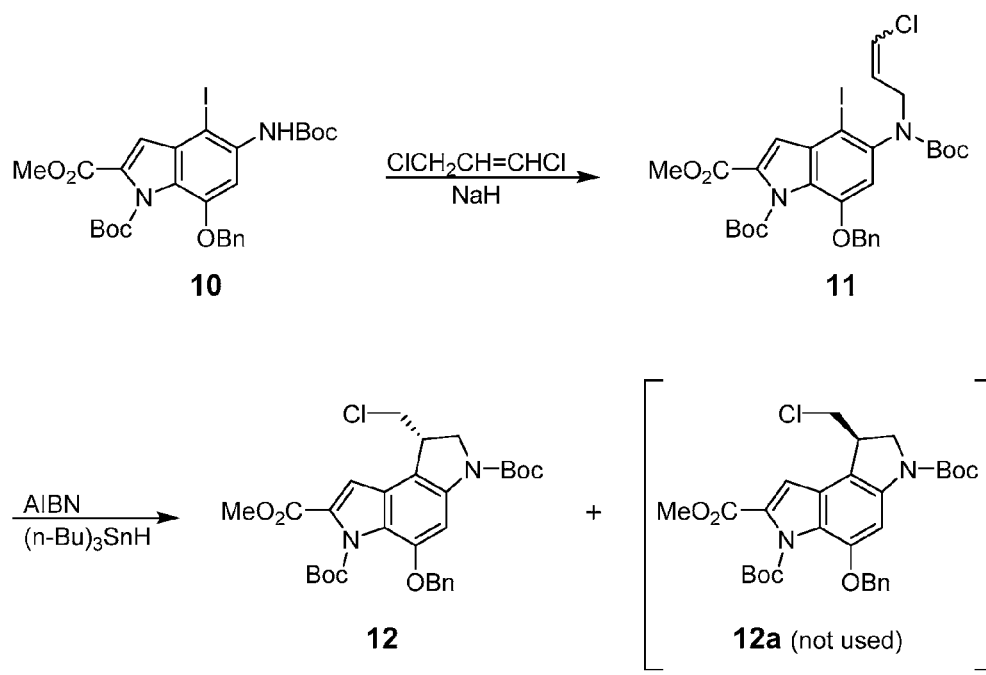

where Hal, $R^1$, $R^2$, and $R^3$ are as defined in the application, are potent anti-cancer agents that can be used in antibody-drug conjugates.

13 Claims, 14 Drawing Sheets

(56) References Cited

OTHER PUBLICATIONS

Hurley, et al., "Reaction of the Antitumor Antibiotic CC-1065 with DNA: Structure of a DNA Adduct with DNA Sequence Specificity," *Science*, vol. 226, pp. 843-844, 1984.

Kobayashi, et al., "Characterristics of Antitumor Activity of KW-2189, a Novel Water-Soluble Derivative of Duocarmycin, Against Murine and Human Tumors," *Cancer Research*, vol. 54, pp. 2404-2410, 1994.

Lajiness, et al., "Design, Synthesis, and Evaluation of Duocarmycin O-Amino Phenol Prodrugs Subject to Tunable Reductive Activation," *Journal of the American Chemical Society*., vol. 53, pp. 7731-7738, 2010.

Li, et al., "Cytotoxicity and Antitumor Activity of Carzelesin, a Prodrug Cyclopropylpyrroloindole Analogue," *Cancer Research*, vol. 52, pp. 4904-4913, 1992.

Nagamura, et al., "Synthesis and Antitumor Activity of Duocarmycin Derivatives: Modification of Segment A of Duocarmycin B2," *Chem. Pharm. Bull.*, vol. 44, No. 9, pp. 1723-1730, 1996.

Nagamura and Saito, "Antitumor Antibiotics: Duocarmycins," *Chemistry of Heterocyclic Compounds*, vol. 34, No. 12, pp. 1386-1405, 1998.

Schrama, et al., "Antibody Targeted Drugs as Cancer Therapeutics," *Nature Reviews Drug Discovery*, vol. 5, pp. 147-159, 2006.

Stephenson, et al., "Solid-Phase Synthesis of Duocarmycin Analogues and the Effect of C-Terminal Substitution on Biological Activity," *Journal of Organic Chemistry*, vol. 80, No. 19, pp. 9454-9467, 2015.

Tichenor, et al., "Systematic Exploration of the Structural Features of Yatakemycin Impacting DNA Alkylation and Biological Activity," *Journal of the American Chemical Society*, vol. 129, No. 35, pp. 10858-10869, 2007.

Tietze, et al., "Duocarmycin-Based Prodrugs for Cancer Prodrug Monotherapy," *Bioorganic & Medicinal Chemistry*, vol. 16, pp. 6312-6318, 2008.

Tietze, et al., "Highly Selective Glycosylated Prodrugs of Cytostatic CC-1065 Analogues for Antibody-Directed Enzyme Tumor Therapy," *ChemBioChem*, vol. 2, pp. 758-765, 2001.

International Search Report and Written Opinion, for PCT Application No. PCT/US2017/047465, dated Oct. 25, 2017.

* cited by examiner

SECO-CYCLOPROPAPYRROLOINDOLE COMPOUNDS, ANTIBODY-DRUG CONJUGATES THEREOF, AND METHODS OF MAKING AND USE

CROSS-REFERENCE TO RELATED APPLICATIONS

This application claims the benefit under 35 U.S.C. § 119(e) of U.S. Provisional Application Ser. No. 62/377,052, filed Aug. 19, 2016; the disclosure of which is incorporated herein by reference

BACKGROUND OF THE INVENTION

This invention relates to seco-cyclopropapyrroloindole compounds, conjugates thereof, and methods of making and using such compounds and conjugates.

Double helical DNA has two longitudinal spiral grooves running along its exterior, much like the stripes on a barbershop pole. The two grooves are not identical: one, called the major groove, is much wider than the other, called the minor groove.

The width of the minor groove is approximately equal to the thickness of a benzene ring. Many biologically active DNA-binding molecules are substantially planar polyaromatic molecules having an arcuate footprint, such shape enabling them to slide snugly in the minor groove. One class of these molecules not only bind to DNA, but also alkylate it and are referred to as DNA minor groove binder-alkylators ("MGBAs").

An MGBA subclass is represented by the natural products CC-1065, duocarmycin SA, and yatakemycin (Boger and Johnson 1995; Tichenor et al. 2007). (Full citations for the documents cited herein by first author or inventor and year are listed at the end of this specification.) They comprise an alkylating subunit and one or more binding subunits, the latter contributing to binding to DNA but being chemically unreactive towards it. In CC-1065 and duocarmycin SA, the alkylating subunit is at one end of the molecule and the binding subunit(s) are at the other end. In yatakemycin, the alkylating subunit is flanked by binding subunits. Consonant with the overall MGBA architecture, the alkylating and binding subunits themselves are polyaromatic and substantially planar. As the alkylating subunit has a cyclopropapyrrolo-indole ("CPI") core structure, MGBAs in this subclass are eponymously named CPI compounds.

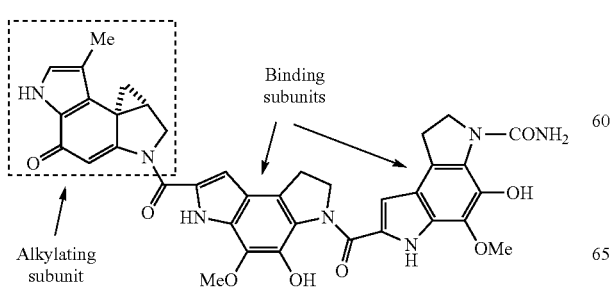
CC-1065

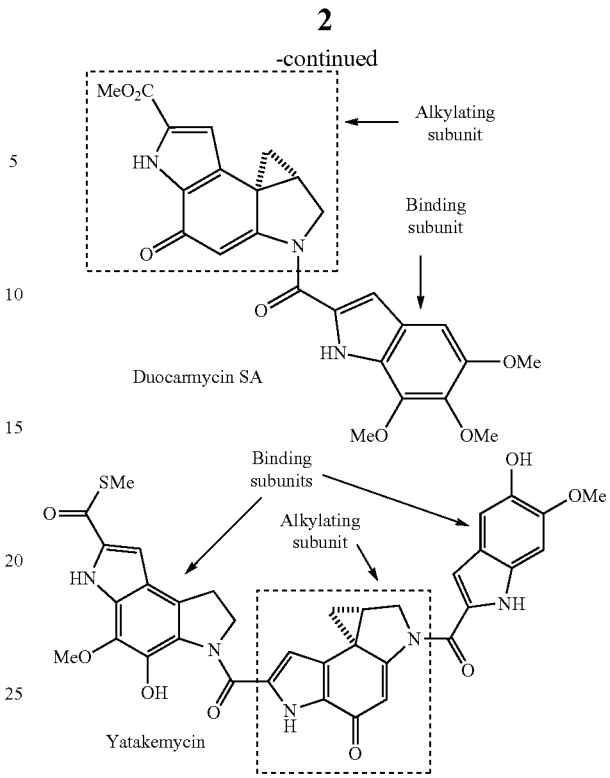
Duocarmycin SA

Yatakemycin

Upon binding to DNA, the CPI cyclopropyl ring is activated and alkylates DNA at an adenine N3 nitrogen (Hurley et al. 1984). One theory proposed to explain the activation is that binding introduces further conformational strain into the already-strained cyclopropyl ring, increasing its reactivity (Boger 2001; Boger et al. 1997; Tichenor et al. 1997).

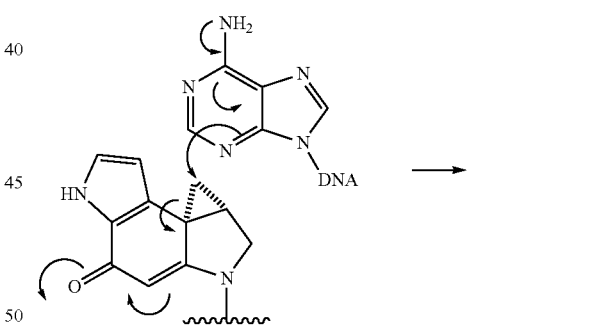

Seco-CPI compounds are variants of CPI compounds in which the cyclopropyl ring has been opened and replaced with a halomethyl group. While seco-CPI compounds themselves do not alkylate DNA, they are readily convertible in vitro or in vivo to CPI compounds and their biological activity is essentially the same as the latter's (Li et al. 2012). Thus, seco-CPI compounds are of interest as synthetically convenient functional equivalents of CPI compounds or as intermediates for their synthesis (Boger et al. 2000).

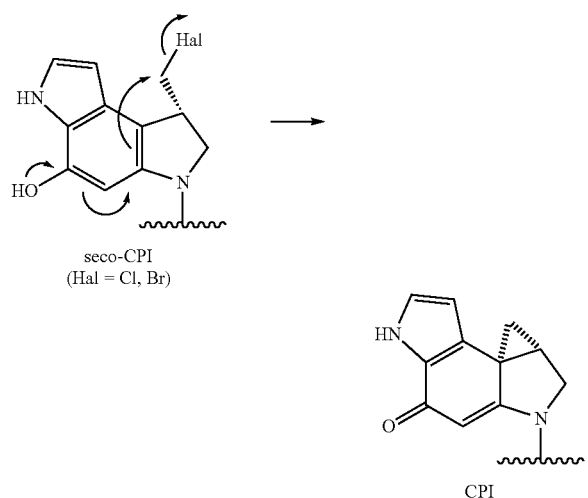

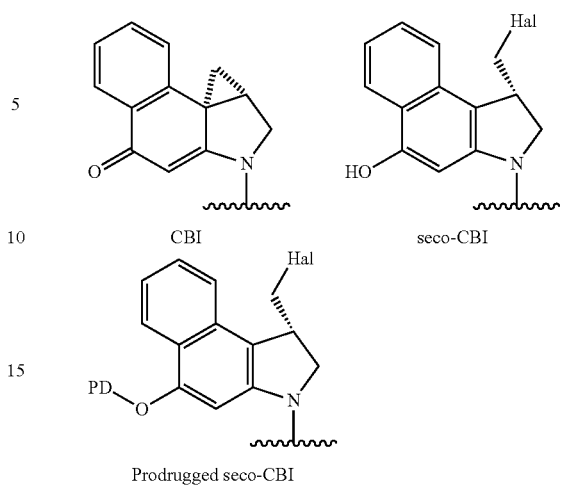

An advantage of a seco-CPI compound is that it can be prodrugged to control conversion to the CPI form. Attaching a prodrugging group PD to the phenolic hydroxyl group prevents conversion to the CPI form unless PD is cleaved off first. PD can be chosen such that it is cleaved by an agent found at or near the site of intended biological action, such as a tumor, to reduce the risk of systemic toxicity. PD preferably is an enzymatically cleavable group, such as a carbamate, phosphate, glycoside, or glucuronide, which are cleavable by carboxyesterase, phosphatase, glycosidase, or glucuronidase, respectively. See, e.g., Kobayashi et al. 1994; Lajiness et al. 2010; Sufi et al. 2013; Tietze et al. 2001; Zhang et al. 2014.

Both CPI and CBI compounds are potent cytotoxins, making them attractive candidates as anti-cancer agents. Substantial research efforts have been dedicated to synthesizing and evaluating such compounds and their seco variants for such use. See, e.g., Boger 2003; Kobayashi et al. 1994; Li et al. 1992; Nagamura and Saito 1998; Nagamura et al. 1996; Tichenor et al. 2007; Tietze et al. 2008.

A type of anticancer agent that is generating strong interest is a conjugate, in which a drug is attached to a targeting agent that binds to a ligand on the cancer cell. The targeting agent thus directs the drug to the cancer cell, where it is released by one of several mechanisms to act on the cancer cell.

A common type of conjugate is an antibody-drug conjugate (ADC, also referred to as an immunoconjugate). In an ADC, a drug (also referred to as a therapeutic agent, cytotoxin, payload, or warhead) is covalently linked to an antibody whose antigen is a tumor associated antigen—i.e., an antigen expressed by a cancer cell.

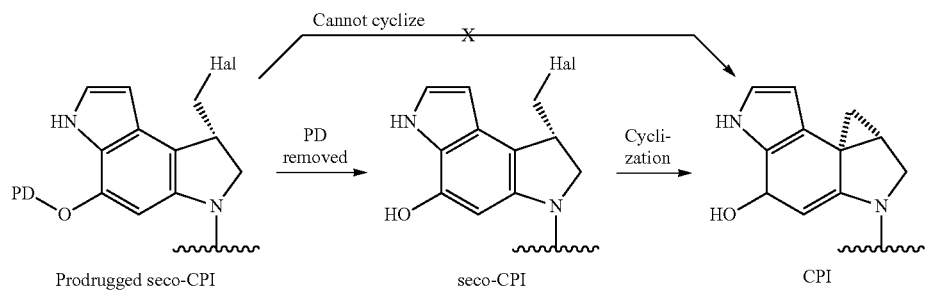

Studies on analogs of CPI compounds led to the development of another MGBA subclass, in which the CPI pyrrole group is replaced by a benzene ring. Such compounds are called CBI compounds, after the cyclopropabenzindole ("CBI") core of the alkylating subunit. Like CPI compounds, CBI compounds can exist in seco and prodrugged seco forms. The simpler CBI structure is more accessible synthetically and CBI compounds have been shown to be both stable and biologically potent (Lajiness et al. 2010; Boger et al. 1990 and 1999).

The moiety covalently linking the antibody and the drug is referred to as the linker. Where each antibody has one drug attached to it, the structure of an ADC can be represented as:

[Antibody]-[Linker]-[Drug]

The antibody, upon binding to the antigen, delivers the ADC to the cancer site. There, cleavage of the linker or degradation of the antibody releases the drug. Frequently, the ADC is internalized by endocytosis into the target cell and release of the drug takes place inside it. While the ADC is circulating in the blood, the drug is held inactive because of its linkage to the antibody. Consequently, the drug in an ADC can be much more potent (cytotoxic) than an ordinary chemotherapy agent because its localized release reduces systemic toxicity. For a review on ADCs, see Schrama et al. 2006.

CPI and CBI compounds, along with their seco counterparts, have been proposed as the drug in an ADC. See, for example, Boyd et al. 2008; Chari et al. 1995; Chen et al. 2014; Ducry et al. 2010; Gangwar et al. 2011; Ng et al. 2006, 2009, and 2011; Sufi et al. 2013; Zhang et al. 2014; Zhao et al. 2010.

BRIEF SUMMARY OF THE INVENTION

The present invention provides novel and highly potent seco-CPI compounds, which are suitable for use as the drug in an ADC or other conjugate. These compounds have an amide group attached to the pyrrole group of the seco-CPI subunit and one or more binding subunits attached to its other end.

In one aspect, this invention provides a seco-CPI compound having a structure represented by formula (I):

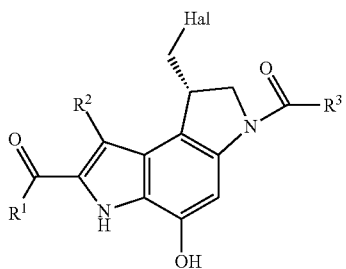

(I)

wherein
Hal is Cl or Br;
$R^1$ is

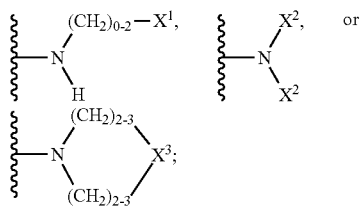

$R^2$ is H, $C_1$-$C_3$ alkyl, $CO_2H$, $CO_2(C_1$-$C_3$ alkyl), $C(=O)NH_2$, $C(=O)NH(C_1$-$C_3$ alkyl), or $C(=O)N(C_1$-$C_3$ alkyl)$_2$;
$R^3$ is

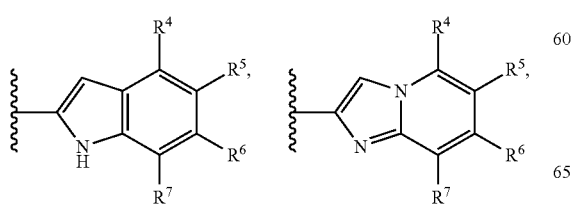

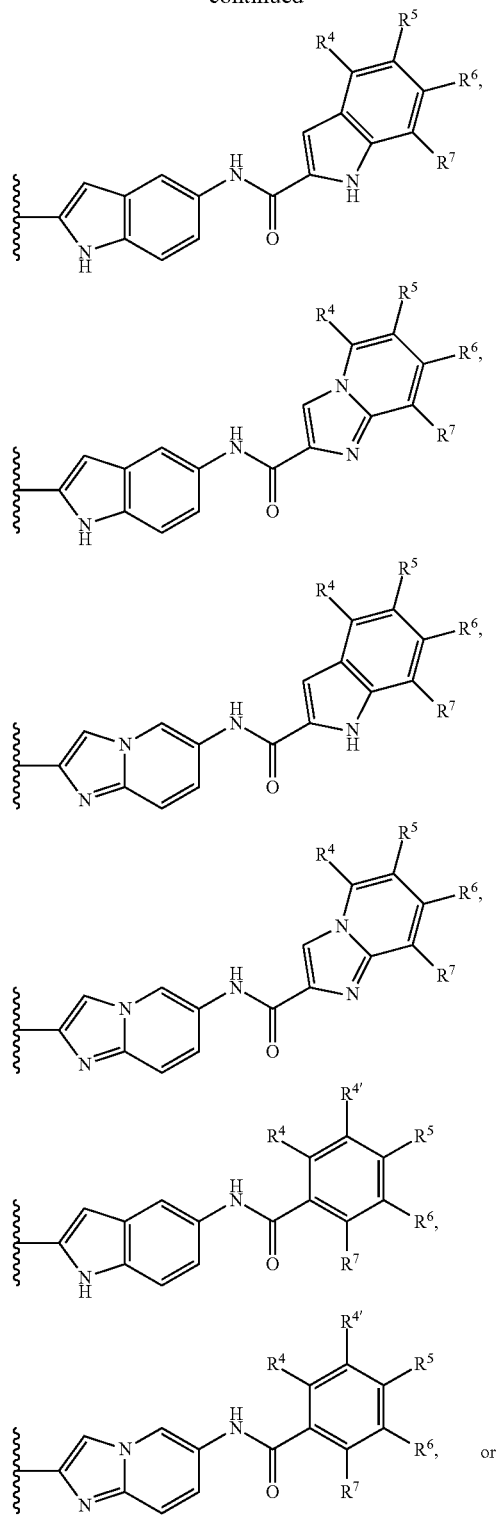

$R^4$, $R^{4'}$, $R^5$, $R^6$, or $R^7$ are independently H, OMe, OH, a 6-membered aryl (preferably phenyl) group, a 5- or 6-membered heteroaryl group, $NH_2$, NHMe, $NMe_2$, $NH(C_2-C_4$ alkyl), $N(C_2-C_4$ alkyl$)_2$, NHC(=O)$X^1$, O($C_2$-$C_4$ alkyl), O($CH_2)_{0-2}$($C_3$-$C_6$ cycloalkyl), O($CH_2)_{0-2}X^1$, or

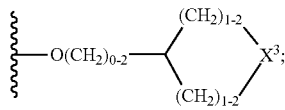

wherein a $C_2$-$C_4$ alkyl group may unsubstituted or substituted with $OCH_2CH_2OH$, $OCH_2CH_2NH_2$, $NHCH_2CH_2OH$, $NHCH_2CH_2NH_2$, OH, or $NH_2$ and an aryl or heteroaryl group may be substituted with $C_1$-$C_2$ alkyl, OH, $NH_2$, NH($C_1$-$C_2$ alkyl), N($C_1$-$C_2$ alkyl$)_2$, F, Cl, Br, $NO_2$, or CN;

with the proviso that at least one of $R^4$, $R^{4'}$, $R^5$, $R^6$, and $R^7$ is other than H;

$R^8$ and $R^{8'}$ are independently H, OH, O($C_1$-$C_3$ alkyl), Cl, Br, F, O($CH_2)_{2-4}NH_2$, or O($CH_2)_{2-4}OH$;

$R^9$ is H, C(=O)($C_1$-$C_3$ alkyl), C(=O)$NH_2$, C(=O)NH($C_1$-$C_3$ alkyl), C(=O)($C_1$-$C_3$ alkyl$)_2$, ($CH_2)_{2-4}OH$, ($CH_2)_{2-4}O$ ($C_1$-$C_3$ alkyl), ($CH_2)_{2-4}NH_2$, ($CH_2)_{2-4}NH(C_1$-$C_3$ alkyl), or ($CH_2)_{2-4}N(C_1$-$C_3$ alkyl$)_2$;

each $X^1$ is independently a 6-membered aryl (preferably pheny) or 5- to 6-membered heteroaryl group that is unsubstituted or substituted with $C_1$-$C_3$ alkyl, OH, O($C_1$-$C_3$ alkyl), $NH_2$, NH($C_1$-$C_3$ alkyl), N($C_1$-$C_3$ alkyl$)_2$, F, Cl, Br, $NO_2$, or CN;

each $X^2$ is independently H, Me, or a $C_2$-$C_4$ alkyl group that may be unsubstituted or substituted with $OCH_2CH_2OH$, $OCH_2CH_2NH_2$, $NHCH_2CH_2OH$, $NHCH_2CH_2NH_2$, OH, or $NH_2$; and each $X^3$ is independently O, NH, N($C_1$-$C_3$ alkyl), or S; or a pharmaceutically acceptable salt thereof.

In another aspect, this invention provides a seco-CPI compound of this invention attached to a linker, suitable for conjugation to a targeting moiety, especially an antibody.

In another aspect, this invention provides a conjugate of a seco-CPI compound of this invention conjugated via a linker to a targeting moiety, especially an antibody.

In another aspect, this invention provides a method of treating a cancer in a subject suffering from such cancer, comprising administering to the subject a therapeutically effective amount of a compound according to this invention, or a conjugate thereof with an antibody. In a preferred embodiment, the cancer treated is lung, gastric, ovarian, or colon cancer.

In another aspect, this invention provides a seco-CPI compound of this invention, or a conjugate thereof with an antibody, for use in treating a subject suffering from cancer. The cancer can be lung, gastric, ovarian or colon cancer.

BRIEF DESCRIPTION OF THE DRAWING(S)

FIGS. 1A and 1B show a scheme for the synthesis of a seco-CPI core structure that can be used to make compounds of this invention.

FIGS. 2, 4, 6, 7, 8, 9, 10, 11, and 12 show exemplary schemes for the synthesis of seco-CPI compounds of this invention. Those skilled in the art will appreciate that, in some instances, the schemes differ primarily in the order in which various segments of a compound are assembled or the order in which protecting groups are removed and that the order of performance of these steps can be a matter of individual preference.

FIGS. 3A, 3B, and 5 show exemplary schemes for the synthesis of seco-CPI linker compounds of this invention. Again, those skilled in the art will appreciate that variations in the order of performance of certain steps may be subject to individual preference.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology,* 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, V$_L$ and V$_H$, are encoded by separate genes, they can be joined, using recombinant methods, by a synthetic linker that enables them to be made as a single protein chain in which the V$_L$ and V$_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germ-line immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human anti-body" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "C$_3$ aliphatic," "C$_{1-5}$ aliphatic," "C$_1$-C$_5$ aliphatic," or "C$_1$ to C$_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in C$_{2-4}$ alkene, C$_4$-C$_7$ cycloaliphatic, etc. In a similar vein, a term such as "(CH$_2$)$_{1-3}$" is to be understand as shorthand for the subscript being 1, 2, or 3, so that such term represents CH$_2$, CH$_2$CH$_2$, and CH$_2$CH$_2$CH$_2$.

"Alkyl" means a saturated aliphatic moiety, with the same convention for designating the number of carbon atoms being applicable. By way of illustration, C$_1$-C$_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as CH$_2$CH$_2$, CH$_2$CH$_2$CH$_2$, and CH$_2$CH$_2$CH$_2$CH$_2$.

"Alkenyl" means an aliphatic moiety having at least one carbon-carbon double bond, with the same convention for designating the number of carbon atoms being applicable. By way of illustration, C$_2$-C$_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, C$_2$-C$_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.+

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocyclo-aliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~ ) transverse to a bond or an asterisk (*) at the end of the bond denotes a covalent attachment site. For instance, a statement that R is

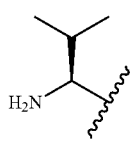

or that R is

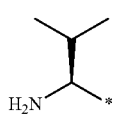

in the formula

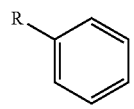

means

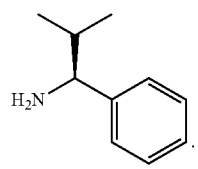

In the formulae of this specification, a bond traversing an aromatic ring between two carbons thereof means that the group attached to the bond may be located at any of the available positions of the aromatic ring. By way of illustration, the formula

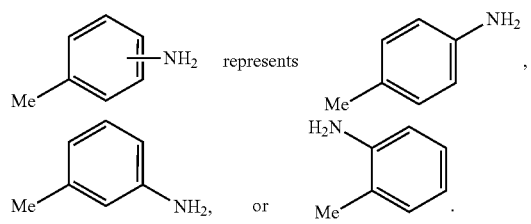

SECO-CPI Compounds

In formula (I) and other formulae where these variables are present, the following preferred embodiments apply, either individually or in combination with other preferred embodiments, unless the context indicates a different preferred embodiment or combination of preferred embodiments is applicable:

(i) Hal is Cl.

(ii) $R^2$ is H.

(iii) $R^3$ is

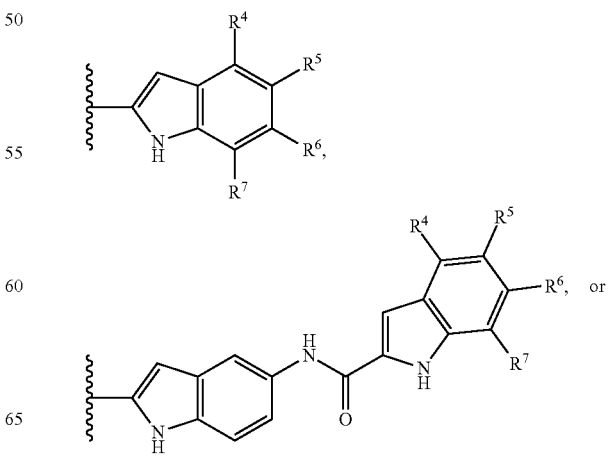

-continued

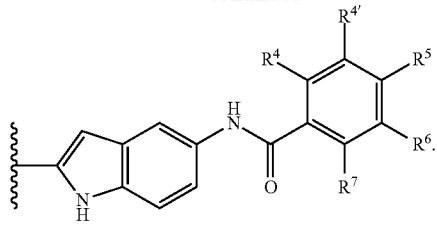

(iv) $R^5$ is OMe, OH, phenyl, $NH_2$, NHMe, $NMe_2$, $NH(C_2$-$C_4$ alkyl), $N(C_2$-$C_4$ alkyl$)_2$, NHC(=O)$X^1$, O($C_2$-$C_4$ alkyl), O$(CH_2)_{0-2}(C_3$-$C_6$ cycloalkyl), O$(CH_2)_{0-2}X^1$, or

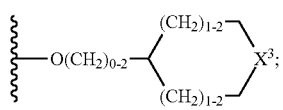

wherein a $C_2$-$C_4$ alkyl group may unsubstituted or substituted with $OCH_2CH_2OH$, $OCH_2CH_2NH_2$, $NHCH_2CH_2OH$, $NHCH_2CH_2NH_2$, OH, or $NH_2$ and a phenyl group may be substituted with $C_1$-$C_2$ alkyl, OH, $NH_2$, $NH(C_1$-$C_2$ alkyl), $N(C_1$-$C_2$ alkyl$)_2$, F, Cl, Br, $NO_2$, or CN;
(i.e., $R^5$ is the one of $R^4$, $R^{4'}$, $R^5$, $R^6$, or $R^7$ that is other than H).

(v) $R^1$ is

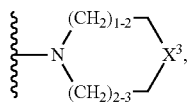

more preferably is

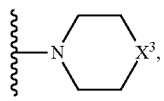

and most preferably is

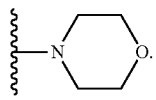

(vi) No more than three, and more preferably no more than two, of $R^4$, $R^{4'}$, $R^5$, $R^6$, and $R^7$ is other than H.

(vii) The aryl or heteroaryl group in $X^1$ is phenyl, pyrrolyl, furanyl, thienyl, imidazolyl, pyrazolyl, oxazolyl, isoxazolyl, thiazolyl, isothiazolyl, triazolyl, tetrazolyl, pyridyl, pyridazinyl, or pyrazinyl; more preferably phenyl and especially phenyl substituted with $NH_2$ or OH.

(viii) Where $R^1$ is

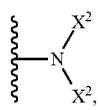

at least one $X^2$ is other than H.

In respect of preference (iii) above, $R^3$ is more preferably is

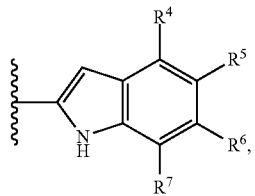

even more preferably where each of $R^4$, $R^6$, and $R^7$ is H.

In a preferred aspect of the invention, compounds according to formula (I) have a structure represented by formula (Ia), where $R^1$, $R^4$, $R^5$, $R^6$, and $R^7$ are as defined in respect of formula (I) in the BRIEF SUMMARY OF THE INVENTION section hereinabove:

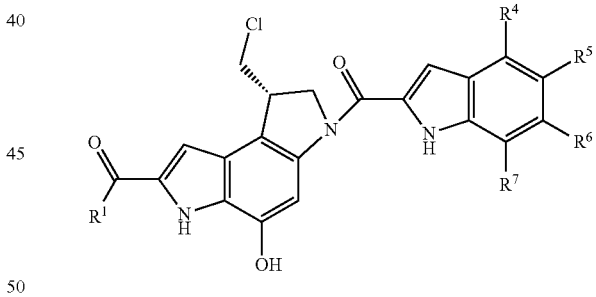

(Ia)

Examples of compounds according to formula (Ia) are listed in Table I, with $R^4$, $R^6$, and $R^7$ each being H unless otherwise noted.

TABLE I

Compounds According to Formula (Ia)

| Cpd. No. | $R^1$ | $R^5$ |
|---|---|---|
| Ia-01 | morpholinyl-CH₂ | -O-CH₂CH₂-OMe |

TABLE I-continued

Compounds According to Formula (Ia)

| Cpd. No. | R¹ | R⁵ |
|---|---|---|
| Ia-02 | morpholine (N-linked) | -O-ethyl |
| Ia-03 | morpholine (N-linked) | -O-propyl |
| Ia-04 | morpholine (N-linked) | -O-CH₂-cyclopropyl |
| Ia-05 | morpholine (N-linked) | -O-isobutyl |
| Ia-06 | morpholine (N-linked) | -O-cyclobutyl |
| Ia-07 | morpholine (N-linked) | -O-CH₂CH₂-cyclopropyl |
| Ia-08 | morpholine (N-linked) | -O-CH₂CH₂-OH |
| Ia-09 | morpholine (N-linked) | -O-CH₂CH₂CH₂-OMe |
| Ia-10 | morpholine (N-linked) | -O-CH₂-cyclohexyl |
| Ia-11 | morpholine (N-linked) | -OMe |

TABLE I-continued

Compounds According to Formula (Ia)

| Cpd. No. | R¹ | R⁵ |
|---|---|---|
| Ia-12 | morpholine (N-linked) | phenyl |
| Ia-13 | morpholine (N-linked) | —O-iPr |
| Ia-14 | morpholine (N-linked) | —O-tetrahydropyran-4-yl |
| Ia-15 | morpholine (N-linked) | —O-cyclopentyl |
| Ia-16 | morpholine (N-linked) | —OCH$_2$CH$_2$NMe$_2$ |
| Ia-17 | morpholine (N-linked) | —OCH$_2$CH$_2$NHMe |
| Ia-18 | morpholine (N-linked) | —OCH$_2$CH$_2$NH$_2$ |
| Ia-19 | morpholine (N-linked) | —NH$_2$ |
| Ia-20 | 4-methylpiperazin-1-yl | —OMe |
| Ia-21 | —N(Me)CH$_2$CH$_2$NHMe | —OMe |

TABLE I-continued
Compounds According to Formula (Ia)
| Cpd. No. | R¹ | R⁵ |
|---|---|---|
| Ia-22 | 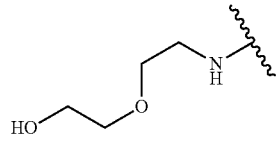 [SMILES: *NCCOCCO] | 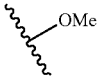 |
| Ia-23 | 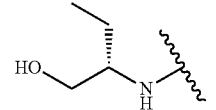 | 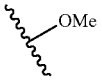 |
| Ia-24 | 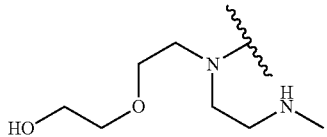 [SMILES: *N(CCNC)CCOCCO] | 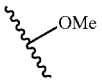 |
| Ia-25 | 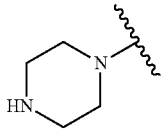 | 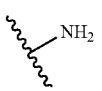 |
| Ia-26 | 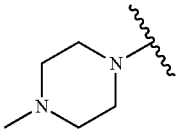 [SMILES: *N1CCN(C)CC1] | 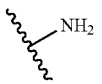 |
| Ia-27 | 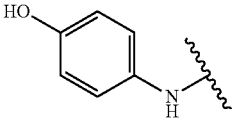 | 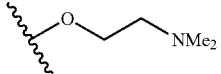 |
| Ia-28 | 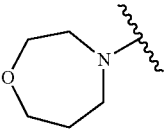 [SMILES: *N1CCCOCC1] | 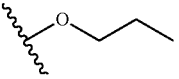 [SMILES: *OCCC] |
| Ia-29 | 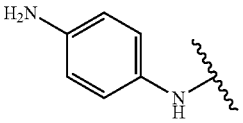 | 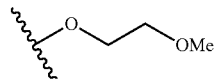 [SMILES: *OCCOC] |
| Ia-30 | 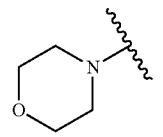 [SMILES: *N1CCOCC1] | 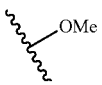 (R⁴ = H, R⁶ = R⁷ = OMe) |
| Ia-31 | 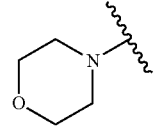 | 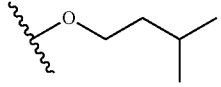 [SMILES: *OCCC(C)C] |

A preferred seco-CPI compound is (Ia-01), whose complete structure is shown following:

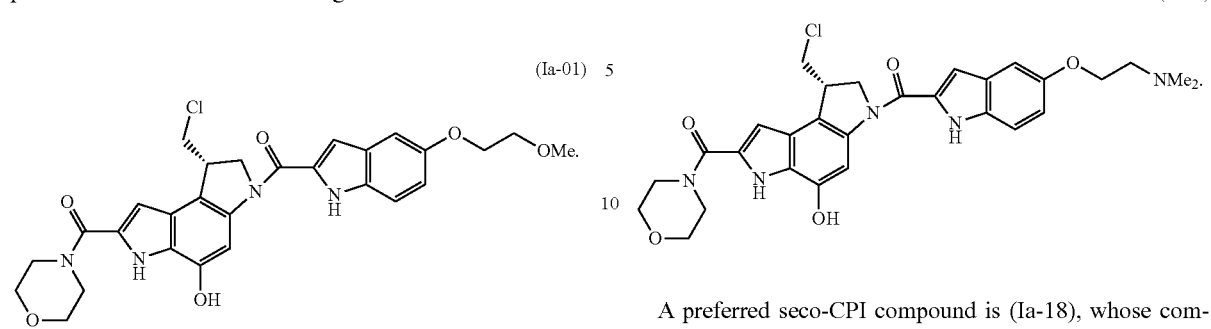

(Ia-01)

A preferred seco-CPI compound is (Ia-02), whose complete structure is shown following:

(Ia-02)

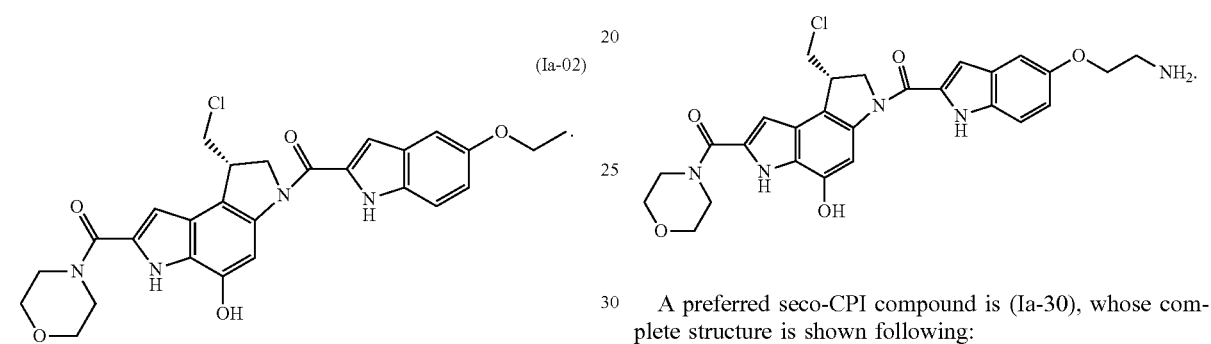

A preferred seco-CPI compound is (Ia-03), whose complete structure is shown following:

(Ia-03)

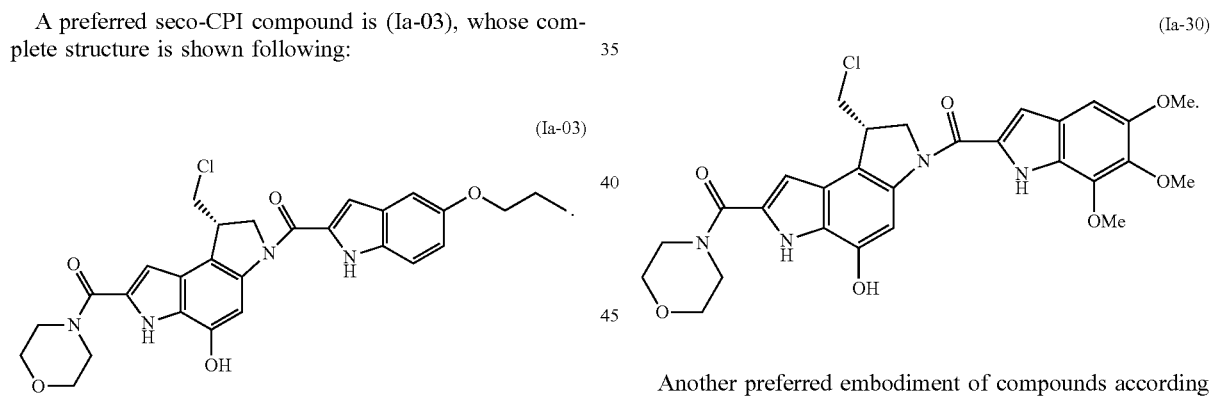

A preferred seco-CPI compound is (Ia-09), whose complete structure is shown following:

(Ia-09)

A preferred seco-CPI compound is (Ia-16), whose complete structure is shown following:

(Ia-16)

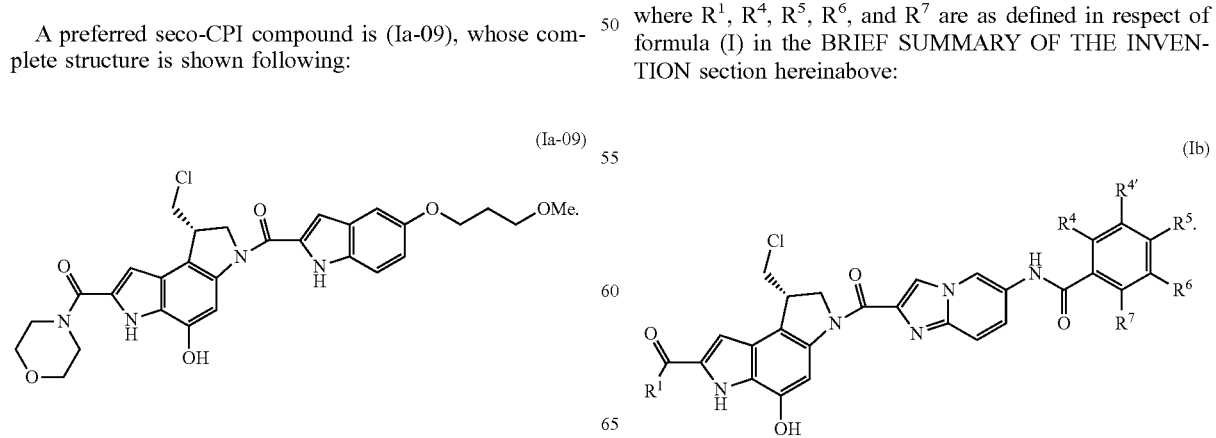

A preferred seco-CPI compound is (Ia-18), whose complete structure is shown following:

(Ia-18)

A preferred seco-CPI compound is (Ia-30), whose complete structure is shown following:

(Ia-30)

Another preferred embodiment of compounds according to formula (I) has a structure represented by formula (Ib), where $R^1$, $R^4$, $R^5$, $R^6$, and $R^7$ are as defined in respect of formula (I) in the BRIEF SUMMARY OF THE INVENTION section hereinabove:

(Ib)

Examples of compounds according to formula (Ib) are listed in Table II ($R^4$, $R^{4'}$, $R^6$, and $R^7$ each being H).

TABLE II

Compounds According to Formula (Ib)

| Cpd. No. | $R^1$ | $R^5$ |
|---|---|---|
| Ib-01 | morpholine-N- | -OH |
| Ib-02 | morpholine-N- | -O-CH₂-O-OMe |

Another preferred embodiment of compounds according to formula (I) has a structure represented by formula (Ic), where $R^1$, $R^4$, $R^5$, $R^6$, and $R^7$ are as defined in respect of formula (I) in the BRIEF SUMMARY OF THE INVENTION section hereinabove:

Another embodiment of compounds (I) has a structure represented by formula (Id), where $R^1$, $R^4$, $R^{4'}$, $R^5$, $R^6$, and $R^7$ are as defined in respect of formula (I) in the BRIEF SUMMARY OF THE INVENTION section hereinabove:

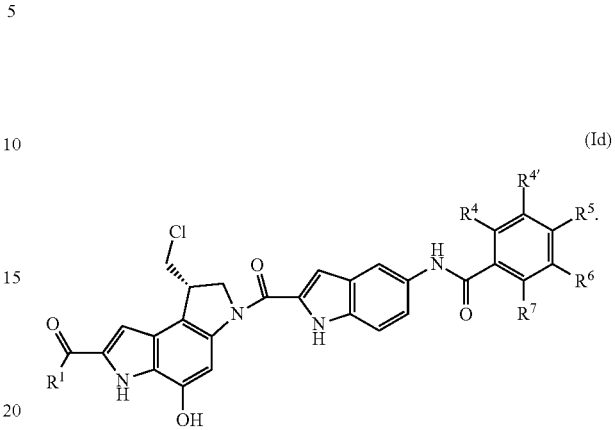

(Id)

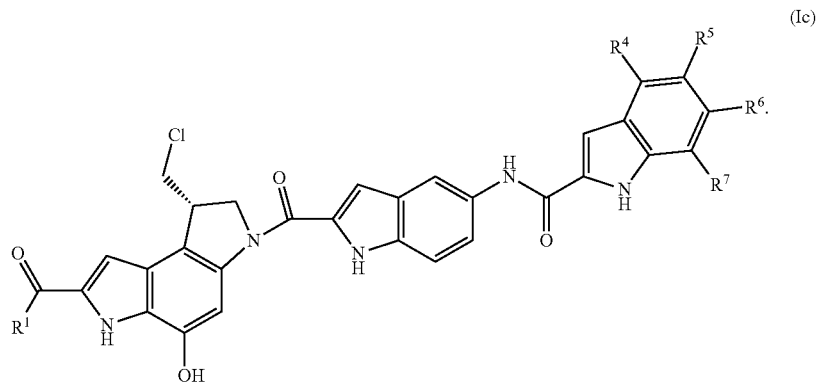

(Ic)

An example of a compound (Ic) is compound (Ic-01):

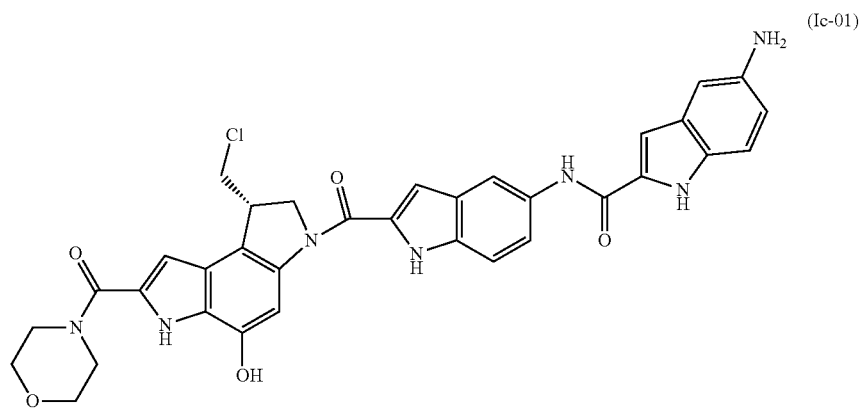 [SMILES: Nc1ccc2[nH]c(C(=O)Nc3ccc4[nH]c(C(=O)N5C[C@@H](CCl)c6c5cc(O)c5[nH]c(C(=O)N7CCOCC7)cc65)cc4c3)cc2c1]

(Ic-01)

Examples of compounds (Id) are (Id-01) and (Id-02):
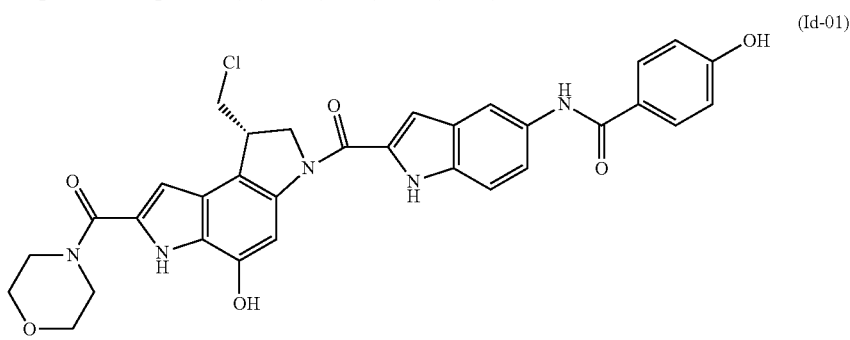
(Id-01)
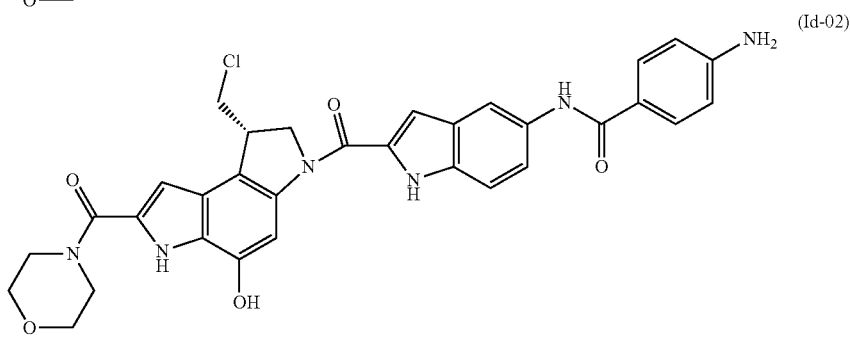
(Id-02)
Specific preferred embodiments of $R^1$ are
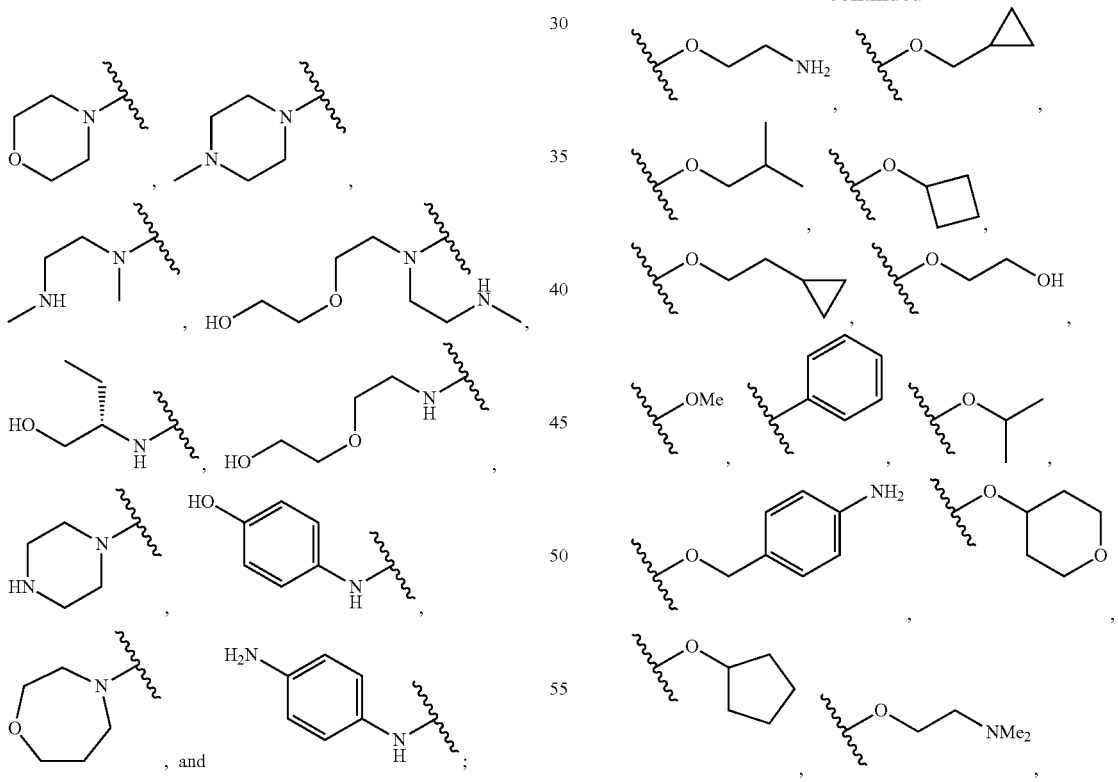
, and ;
and specific preferred embodiments of $R^5$ are
and .

Without being bound by theory, it is believed that the R¹ groups of this invention are hydrophilic, advantageously improving their properties. Having a low CLogP R¹ group can be advantageous because it increases the aqueous solubility of a seco-CPI compound and its linker construct. As noted in Examples 1 and 2 below, conjugation to an antibody is performed in an essentially aqueous medium and a more soluble seco-CPI compound-linker compound can be more efficiently conjugated. Further, in the event of unintended premature cleavage of an ADC releasing seco-CPI compound into the blood, the increased hydrophilicity reduces the likelihood that the compound will permeate through a cell membrane and cause off-target toxicity. (Entry of an ADC into a cell is by a different process: endocytosis triggered by binding of the antibody to its antigen.)

The open valence in each group R¹—see, e.g., Table I—is at a nitrogen, so that it forms an amide bond with the carboxyl group of the seco-CPI core. Their hydrophilicity can be estimated via the hydrophilicty of the corresponding amines R¹H.

The hydrophilicty (or, conversely, the hydrophobicity) of a compound can be estimated from its CLogP, which is a value calculatable from its structure: lower values indicate a more hydrophilic molecule while higher values indicating a more hydrophobic molecule. CLogP values for the amines R¹H corresponding to the R¹ groups in Table I are shown following. The CLogP values are all less than 0.300, ranging from −1.484 to 0.248. (CLogP values were calculated using CHEMBIODRAW® Ultra software (Version 14.0.0.126) from PerkinElmer. (The same software was used to calculate CLogP values cited elsewhere in this specification.)

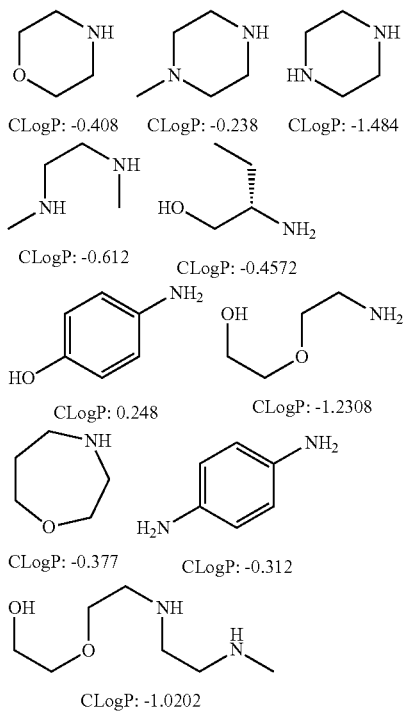

For comparison, Tichenor et al. 2007 disclose compounds 15a and 15b having a pyrrolodinyl amide attached to a seco-CPI core, but the CLogP value for the corresponding amine (pyrroline) is significantly higher, 0.376.

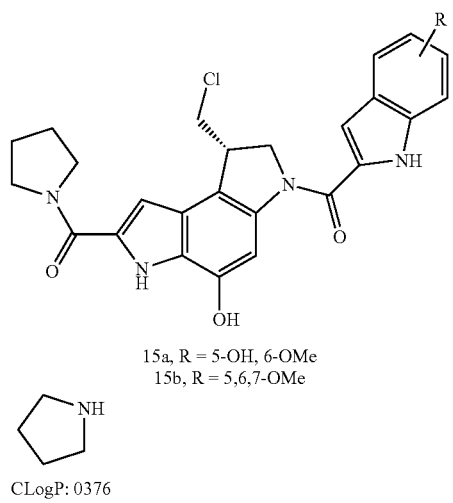

15a, R = 5-OH, 6-OMe
15b, R = 5,6,7-OMe

CLogP: 0376

Thus, in one embodiment, the groups R¹ are those whose corresponding amine R¹H have a CLogP value of less than 0.300, as calculated using the aforementioned CHEMBIO-DRAW™ software.

Conjugates

General

Seco-CPI compounds of this invention can be used as therapeutic agents per se, but preferably are used in conjugates. More preferably, the targeting moiety in the conjugate is an antibody or antigen binding portion thereof and its antigen is a tumor associated antigen, i.e., one that is expressed by a cancer cell. Preferably, the tumor associated antigen is uniquely expressed or overexpressed by the cancer cell, compared to a normal cell. The tumor associated antigen can be located on the surface of the cancer cell or secreted by the cancer cell into its environs.

Thus, another embodiment of this invention is a conjugate comprising seco-CPI compound of this invention and a ligand, represented by formula (II)

$$[D(X^D)_a(C)_c(X^Z)_b]_m Z \qquad (II)$$

where Z is a targeting moiety, D is a seco-CPI compound of this invention, and —$(X^D)_a C(X^Z)_b$— are collectively referred to as a "linker moiety" or "linker" because they link Z and D. Within the linker, C is a cleavable group designed to be cleaved at or near the site of intended biological action of D; $X^D$ and $X^Z$ are spacer moieties (or "spacers") that space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

By binding to a target tissue or cell where its antigen or receptor is located, Z directs the conjugate there. Cleavage of group C at the target tissue or cell releases D to exert its cytotoxic effect locally. In some instances, the conjugate is internalized into a target cell by endocytosis and cleavage takes place within the target cell. In this manner, precise delivery of D is achieved at the site of intended action, reducing the dosage needed. Also, D is normally biologically inactive (or significantly less active) in its conjugated state, thereby reducing undesired toxicity against non-target tissue or cells.

As reflected by the subscript m, each Z can conjugate with more than one D, depending on the number of sites Z has available for conjugation and the experimental conditions employed. Those skilled in the art will appreciate that, while each individual Z is conjugated to an integer number of Ds, a preparation of the conjugate may analyze for a non-integer ratio of D to Z, reflecting a statistical average. This ratio is referred to as the substitution ratio ("SR") or the drug-antibody ratio ("DAR").

Targeting Moiety Z

Preferably, targeting moiety Z is an antibody. For convenience and brevity and not by way of limitation, the detailed discussion in this specification about Z and its conjugates is written in the context of its being an antibody, but those skilled in the art will understand that other types of Z can be conjugated, mutatis mutandis. For example, conjugates with folic acid as the targeting moiety can target cells having the folate receptor on their surfaces (Leamon et al., Cancer Res. 2008, 68 (23), 9839). For the same reasons, the detailed discussion in this specification is primarily written in terms of a 1:1 ratio of Z to D (m=1).

Preferably, Z is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference.

In addition to being an antibody, Z can also be an antibody fragment (such as Fab, Fab', F(ab')$_2$, Fd, or Fv) or antibody mimetic, such as an affibody, a domain antibody (dAb), a nanobody, a unibody, a DARPin, an anticalin, a versabody, a duocalin, a lipocalin, or an avimer.

Any one of several different reactive groups on Z can be a conjugation site, including ε-amino groups in lysine residues, pendant carbohydrate moieties, carboxylic acid groups on aspartic or glutamic acid side chains, cysteine-cysteine disulfide groups, and cysteine thiol groups. For reviews on antibody reactive groups suitable for conjugation, see, e.g., Garnett, *Adv. Drug Delivery Rev.* 2001, 53, 171-216 and Dubowchik and Walker, *Pharmacology & Therapeutics* 1999, 83, 67-123, the disclosures of which are incorporated herein by reference.

Most antibodies have multiple lysine residues, which can be conjugated via their ε-amino groups via amide, urea, thiourea, or carbamate bonds.

In another embodiment, Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference.

In another embodiment, Z can be conjugated via an aspartic or glutamic acid side chain carboxylic acid, for example by conversion to a carbohydrazide, which is then reacted with an aldehyde-bearing linker. See Fisch et al., *Bioconjugate Chemistry* 1992, 3, 147-153.

A thiol (—SH) group in the side chain of a cysteine can be used to form a conjugate by several methods. It can be used to form a disulfide bond between it and a thiol group on the linker. Another method is via its Michael addition to a maleimide group on the linker.

Typically, although antibodies have cysteine residues, they lack free thiol groups because all their cysteines are engaged in intra- or inter-chain disulfide bonds. To generate a free thiol group, a native disulfide group can be reduced. See, e.g., Packard et al., *Biochemistry* 1986, 25, 3548; King et al., *Cancer Res.* 1994, 54, 6176; and Doronina et al., *Nature Biotechnol.* 2003, 21, 778. Alternatively, a cysteine having a free —SH group can be introduced by mutating the antibody, substituting a cysteine for another amino acid or inserting one into the polypeptide chain. See, for example, Eigenbrot et al., U.S. Pat. No. 7,521,541 B2 (2009); Chilkoti et al., *Bioconjugate Chem.* 1994, 5, 504; Urnovitz et al., U.S. Pat. No. 4,698,420 (1987); Stimmel et al., *J. Biol. Chem.* 2000, 275, 30445; Bam et al., U.S. Pat. No. 7,311,902 B2 (2007); Kuan et al., *J. Biol. Chem.* 1994, 269, 7610; Poon et al., *J. Biol. Chem.* 1995, 270, 8571; Junutula et al., *Nature Biotechnology* 2008, 26, 925 and Rajpal et al., U.S. Provisional Application No. 62/270,245, filed Dec. 21, 2015. In yet another approach, a cysteine is added to the C-terminus of the heavy of light chain. See, e.g., Liu et al., U.S. Pat. No. 8,865,875 B2 (2014); Cumber et al., *J. Immunol.* 1992, 149, 120; King et al., *Cancer Res.* 1994, 54, 6176; Li et al., *Bioconjugate Chem.* 2002, 13, 985; Yang et al., *Protein Engineering* 2003, 16, 761; and Olafson et al., *Protein*

*Engineering Design & Selection* 2004, 17, 21. The disclosures of the documents cited in this paragraph are incorporated herein by reference.

Linkers and their Components

As noted above, the linker comprises up to three elements: a cleavable group C and optional spacers $X^Z$ and $X^D$.

Group C is cleavable under physiological conditions. Preferably it is relatively stable while the conjugate is in circulation in the blood, but is readily cleaved once the conjugate reaches its site of intended action, near, at, or within the target cell. Preferably, the conjugate is internalized by a target cell upon binding of an antibody Z to an antigen displayed on the surface of the target cell. Subsequently, cleavage of C occurs in a vesicular body of the target cell (an early endosome, a late endosome, or, especially, a lysosome).

In one embodiment, C is a pH sensitive group. The pH in blood plasma is slightly above neutral, while the pH inside a lysosome is acidic, circa 5. Thus, an acid-sensitive C will cleave at a rate several orders of magnitude faster inside a lysosome than in blood. Examples of acid-sensitive groups are cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 1981, 102, 1048; and Yang et al., *Proc. Natl Acad. Sci* (USA) 1988, 85, 1189; the disclosures of which are incorporated herein by reference.

In another embodiment, C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. See, e.g., Thorpe et al., *Cancer Res.* 2008, 48, 6396-6403; Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2 (2010); and Sufi et al., U.S. Pat. No. 8,461,117 B2 (2013); the disclosures of which are incorporated herein by reference.

A preferred group C is a peptide that is cleaved selectively by a protease inside the target cell, as opposed to by a protease in the serum. Typically, the peptide comprises from 1 to 20 amino acids, preferably from 1 to 6 amino acids, more preferably from 2 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this specification, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of a cancer, e.g., a protease released by nearby dying cancer cells or a tumor-associated protease secreted by cancer cells. Exemplary extracellular tumor-associated proteases are plasmin, matrix metalloproteases (MMP), thimet oligopeptidase (TOP) and CD10. See, e.g., Trouet et al., U.S. Pat. No. 7,402,556 B2 (2008); Dubois et al., U.S. Pat. No. 7,425,541 B2 (2008); and Bebbington et al., U.S. Pat. No. 6,897,034 B2 (2005).

For conjugates designed to be internalized by a cell, C preferably comprises an amino acid sequence selected for cleavage by an endosomal or lysosomal protease, especially the latter. Non-limiting examples of such proteases include cathepsins B, C, D, H, L and S, especially cathepsin B. Exemplary cathepsin B cleavable peptides include Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit. (Herein, amino acid sequences are written in the N-to-C direction, as in $H_2N-AA^2-AA^1-CO_2H$, unless the context clearly indicates otherwise.) See Dubowchik et al., *Biorg. Med. Chem. Lett.* 1998, 8, 3341; Dubowchik et al., *Bioorg. Med. Chem. Lett.* 1998, 8, 3347; and Dubowchik et al., *Bioconjugate Chem.* 2002, 13, 855; the disclosures of which are incorporated by reference.

Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence $-AA^2-AA^1-$ wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu. More preferably, it is a two to three amino acid peptide from the foregoing group.

The preparation and design of cleavable groups C consisting of a single amino acid is disclosed in Chen et al., U.S. Pat. No. 8,664,407 B2 (2014), the disclosure of which is incorporated herein by reference.

Group C can be bonded directly to Z or D; i.e. spacers $X^Z$ or $X^D$, as the case may be, can be absent.

When present, spacer $X^Z$ provides spatial separation between C and Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

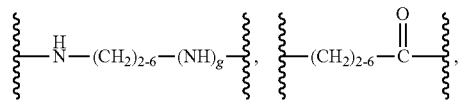

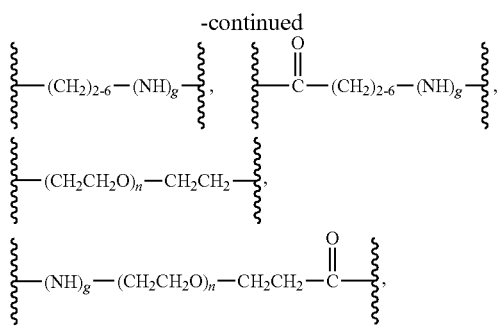

and combinations thereof,
where the subscript g is 0 or 1 and the subscript h is 1 to 24, preferably 2 to 4. These segments can be combined, such as illustrated below:

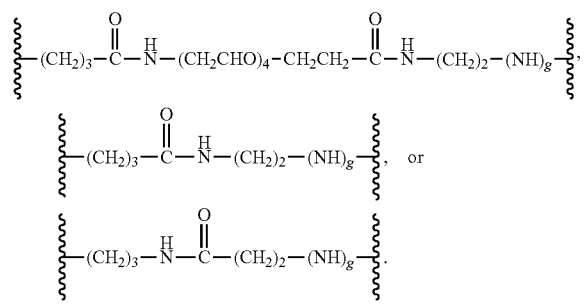

Spacer $X^D$, if present, provides spatial separation between C and D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, analogously to the description above for spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain a poly(ethylene glycol) ("PEG") group. Since the conjugation step typically involves coupling a drug-linker to an antibody in an aqueous medium, a PEG group many enhance the aqueous solubility of the drug-linker. Also, a PEG group may enhance the solubility or reduce aggregation in the resulting ADC. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to C and either Z or D and (2) has a structure such that cleavage from group C initiates a reaction sequence resulting in the self-immolating moiety disbonding itself from Z or D, as the case may be. In other words, reaction at a site distal from Z or D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to D, the biological activity of D may be impaired. The use of a self-immolating moiety is especially desirable where cleavable group C is a polypeptide, in which instance the self-immolating moiety typically is located adjacent thereto, in order to prevent D from sterically or electronically interfering with peptide cleavage.

Exemplary self-immolating moieties (i)-(v) bonded to a hydroxyl or amino group of D are shown below:

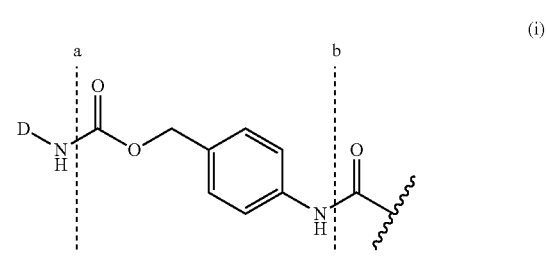

(i)

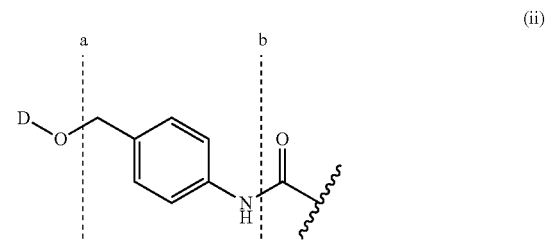

(ii)

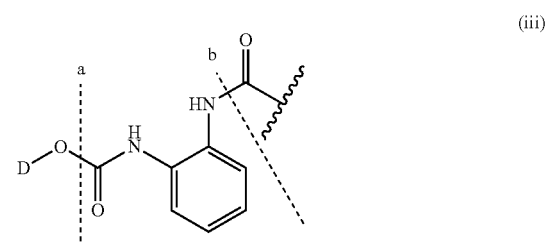

(iii)

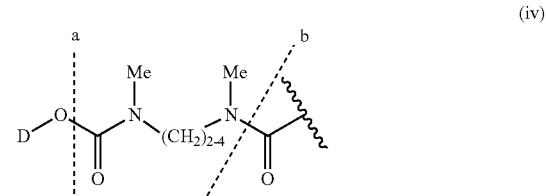

(iv)

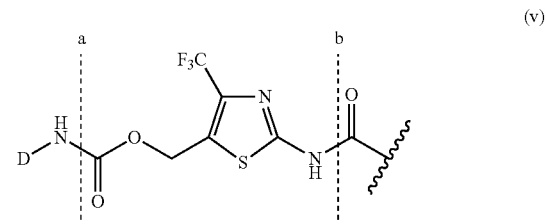

(v)

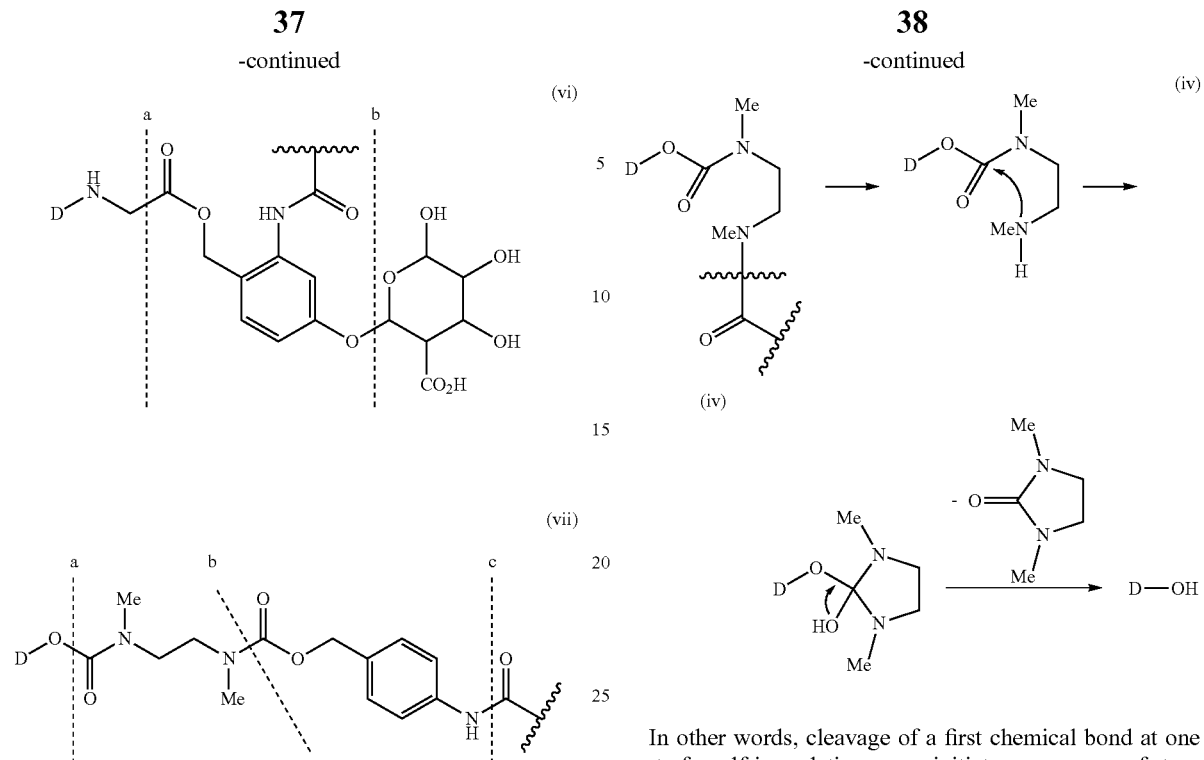

The self-immolating moiety is the structure between dotted lines a and b (or dotted lines b and c), with adjacent structural features shown to provide context. Self-immolating moieties (i) and (v) are bonded to a D-NH$_2$ (i.e., conjugation is via an amino group), while self-immolating moieties (ii), (iii), and (iv) are bonded to a D-OH (i.e., conjugation is via a hydroxyl or carboxyl group). Cleavage of the bond at dotted line b by an enzyme—a peptidase in the instance of structures (i)-(v) and a β-glucuronidase in the instance of structure (vi)—initiates a self-immolating reaction sequence that results in the cleavage of the bond at dotted line a and the consequent release of D-OH or D-NH$_2$, as the case may be. By way of illustration, self-immolating mechanisms for structures (i) and (iv) are shown below:

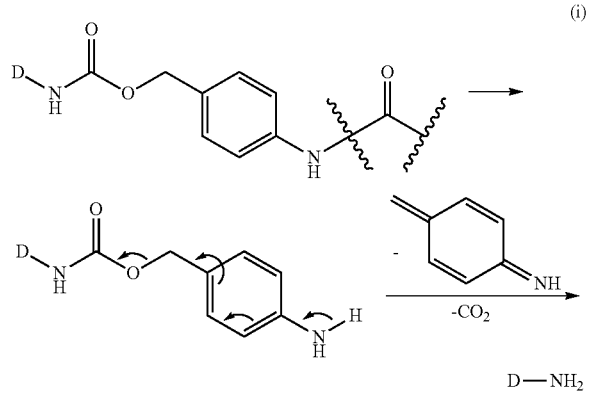

In other words, cleavage of a first chemical bond at one part of a self-immolating group initiates a sequence of steps that results in the cleavage of a second chemical bond—the one connecting the self-immolating group to the drug—at a different part of the self-immolating group, thereby releasing the drug.

In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.* 1981, 24, 479; Carl et al., WO 81/01145 (1981); Dubowchik et al., *Pharmacology & Therapeutics* 1999, 83, 67; Firestone et al., U.S. Pat. No. 6,214,345 B1 (2001); Toki et al., *J. Org. Chem.* 2002, 67, 1866; Doronina et al., *Nature Biotechnology* 2003, 21, 778 (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference.

In another embodiment, Z and D are linked by a non-cleavable linker, i.e., C is absent. Metabolism of D eventually reduces the linker to a small appended moiety that does not interfere with the biological activity of D.

Conjugation Techniques

Conjugates of this invention preferably are made by first preparing a compound comprising D and linker $(X^D)_a(C)_c(X^Z)_b$ (where $X^D$, C, $X^Z$, a, b, and c are as defined for formula (II)) to form drug-linker compound represented by formula (III):

where $R^{31}$ is a functional group suitable for reacting with a complementary functional group on Z to form the conjugate. Examples of suitable groups $R^{31}$ include amino, azide, thiol, cyclooctyne,

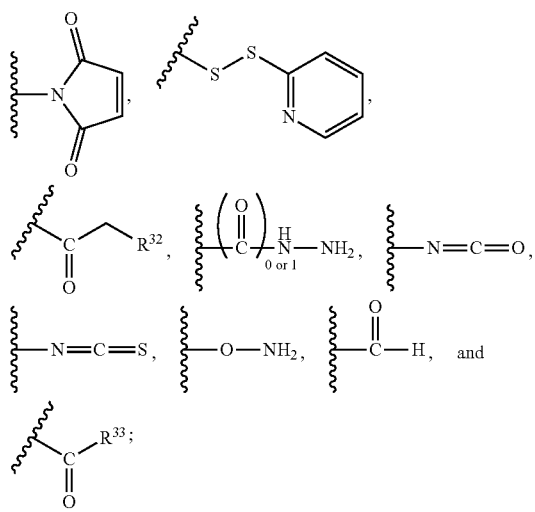

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties D-$(X^D)_a$C$(X^Z)_b$—$R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., U.S. Pat. No. 8,461,117 B2 (2013); and Chen et al., U.S. Pat. No. 8,664,407 B2 (2014); the disclosures of which are incorporated herein by reference.

Preferably reactive functional group —$R^{31}$ is —NH$_2$, —OH, —CO$_2$H, —SH, maleimido, cyclooctyne, azido (—N3), hydroxylamino (—ONH$_2$) or N-hydroxysuccinimido. Especially preferred functional groups —$R^{31}$ are:

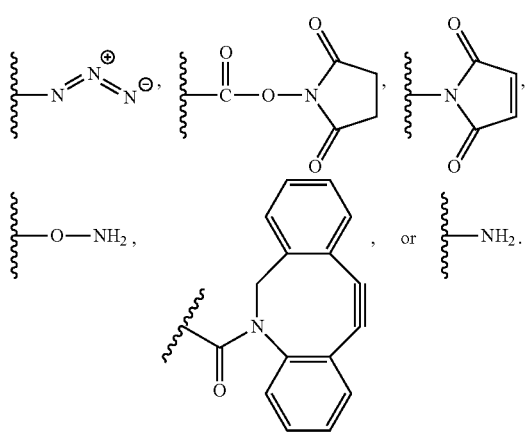

An —OH group can be esterified with a carboxy group on the antibody, for example, on an aspartic or glutamic acid side chain.

A —CO$_2$H group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Where an antibody does not have a cysteine —SH available for conjugation, an ε-amino group in the side chain of a lysine residue can be reacted with 2-iminothiolane or N-succinimidyl-3-(2-pyridyldithio)propionate ("SPDP") to introduce a free thiol (—SH) group—creating a cysteine surrogate, as it were. The thiol group can react with a maleimide or other nucleophile acceptor group to effect conjugation. The mechanism if illustrated below with 2-iminothiolane.

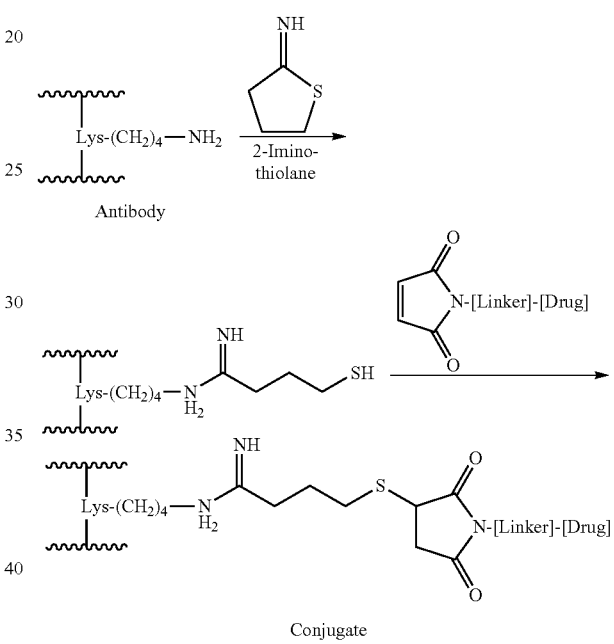

Conjugate

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody Z can be modified with N-succinimidyl 4-(maleimidomethyl)-cyclohexanecarboxylate ("SMCC") or its sulfonated variant sulfo-SMCC, both of which are available from Sigma-Aldrich, to introduce a maleimide group thereto. Then, conjugation can be effected with a drug-linker compound having an —SH group on the linker.

An alternative conjugation method employs copper-free "click chemistry," in which an azide group adds across a strained cyclooctyne to form an 1,2,3-triazole ring. See, e.g., Agard et al., J. Amer. Chem. Soc. 2004, 126, 15046; Best, Biochemistry 2009, 48, 6571, the disclosures of which are incorporated herein by reference. The azide can be located on the antibody and the cyclooctyne on the drug-linker moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

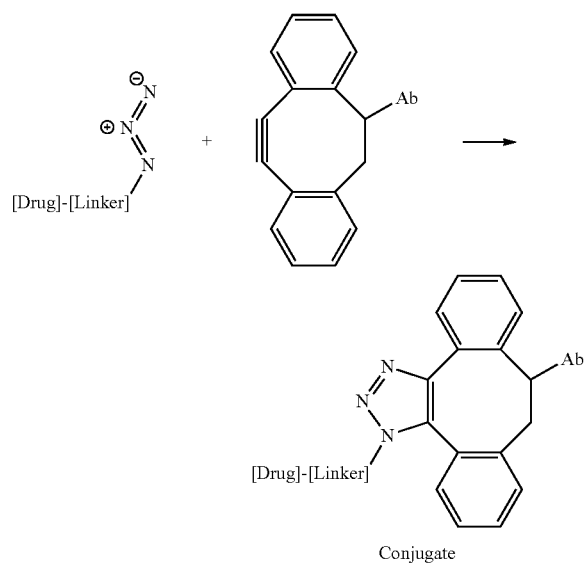

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenyalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416. The foregoing disclosures are incorporated herein by reference. Thus, in one embodiment, an antibody that is used for making a conjugate with a drug of this invention has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase from Streptomyces mobaraensis or BTG), per Jeger et al., Angew. Chem. Int. Ed. 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

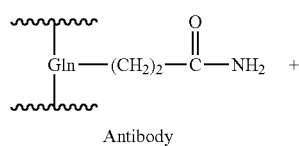

Antibody

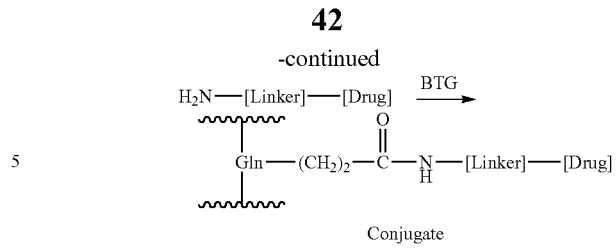

Conjugate

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest, 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, an antibody that is conjugated to a drug of this invention is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., PCT Application No. PCT/US2016/020192, filed Mar. 1, 2016.

In a complementary approach, the substrate specificity of BTG can be altered by varying its amino acid sequence, such that it becomes capable of reacting with glutamine 295 in an umodified antibody, as taught in Rao-Naik et al., U.S. Provisional Application No. 62/236,274, filed Oct. 2, 2015.

Lastly, while the most commonly available bacterial transglutaminase is that from S. mobaraensis, transglutaminase from other bacteria, having somewhat different substrate specificities, can be considered, such as transglutaminase from Streptoverticillium ladakanum (Hu et al., US 2009/0318349 A1 (2009), US 2010/0099610 A1 (2010), and US 2010/0087371 A1 (2010)).

Conjugation can also be effected using the enzyme Sortase A, as taught in Levary et al., PLoS One 2011, 6(4), e18342; Proft, Biotechnol. Lett. 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

Seco-CPI-Linker Compounds

An ADC of a seco-CPI compound of this invention includes a linker attached to a functional group on the seco-CPI compound, which linker is attached to the antibody. Reflecting the diversity of conjugation techniques known in the art, the seco-CPI compounds of this invention can be elaborated into many different seco-CPI compound-linker compounds suitable for conjugation to an antibody.

Generally, there are three different sites for attachment of a linker to a seco-CPI compound of this invention, as illustrated below:

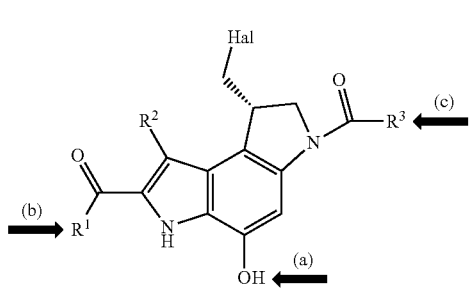

In type (a) seco-CPI-linker compounds, the linker is attached to the phenolic hydroxyl of the binding subunit and, while attached, acts as a prodrugging group preventing cyclization to the CPI structure. In type (b) seco-CPI-linker compounds, the linker is attached via a suitable functionality in the group $R^1$, such as an amino, carboxy, or hydroxyl group. In type (c) seco-CPI-linker compounds, the linker is attached via a suitable functionality in the group $R^3$, such as an amino, carboxy, or hydroxyl group. In types (b) and (c), the phenolic hydroxyl group optionally can be prodrugged, as discussed above.

In one embodiment, type (a) seco-CPI-linker compounds can be represented by the formula (IIIa):

u is 0 or 1;
p is 1, 2, 3, or 4;
q is 1, 2, 3, 4, 5, 6, 7, 8, 9, 10, 11, or 12 (preferably 2, 3, 4, or 8);
r is 1, 2, 3, 4, or 5;
s is 0 or 1;
v is 0 or 1;
$R^{31}$ is H,

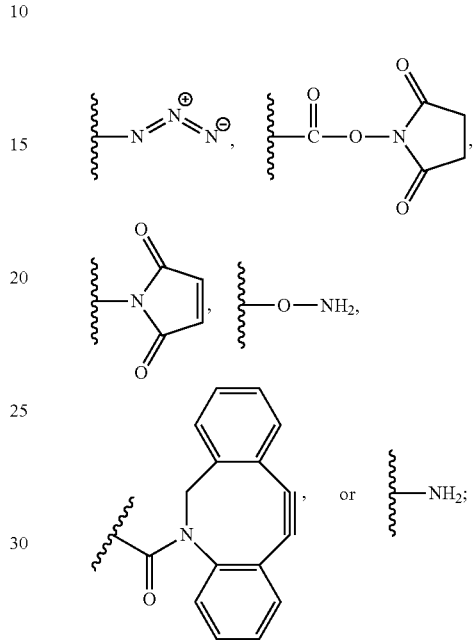

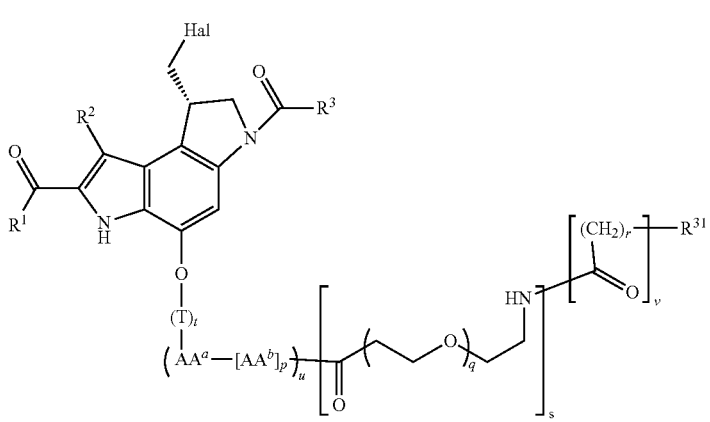

wherein
T is a self-immolating group;
t is 0 or 1;
$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

with the provisos that $R^{31}$ can be H only if s is 1 and v is 0 and that v can be 0 only if s is 1 and $R^{31}$ is H;
and
$R^1$, $R^2$, and $R^3$ are as defined in the BRIEF SUMMARY OF THE INVENTION section hereinabove in respect of formula (I).

In one embodiment of seco-CPI linkers according to formula (IIIa), $R^3$ is

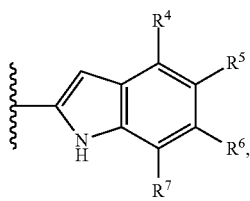

especially where $R^4$, $R^6$, and $R^7$ are each H.

In one embodiment, u is 1 in formula (IIIa).

The moiety -AA$^a$-[AA$^b$]$_p$- represents a polypeptide whose length is determined by the value of p (dipeptide if p is 1, tetrapeptide if p is 3, etc.). AA$^a$ is at the carboxy terminus of the polypeptide and its carboxyl group forms a peptide (amide) bond with an amine nitrogen of the seco-CPI compound. Conversely, the last AA$^b$ is at the amino terminus of the polypeptide and its α-amino group forms a peptide bond with

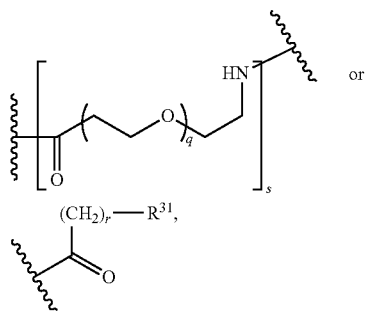

depending on whether s is 1 or 0, respectively. Preferred polypeptides -AA$^a$-[AA$^b$]$_p$- are Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in H$_2$N-Val-Cit-CO$_2$H). More preferably, the polypeptide is Val-Cit, Val-Lys, or Val-Ala. Preferably, a polypeptide -AA$^a$-[AA$^b$]$_p$- is cleavable by an enzyme found inside the target (cancer) cell, for example a cathepsin and especially cathepsin B.

As indicated by the subscript t equals 0 or 1, a self-immolating group T is optionally present. A preferred self-immolating group T is a p-aminobenzyl alcohol (PABA) group, which has the structure is shown below (phenolic oxygen not shown), with an asterisk (*) denoting the end bonded to the phenolic oxygen of the seco-CPI compound and a wavy line (⌇) denoting the end bonded to the polypeptide -AA$^a$-[AA$^b$]$_p$-.

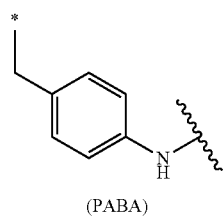 [SMILES: *Nc1ccc(CC)cc1]

(PABA)

Another preferred self-immolating group T is a p-aminobenzyl oxycarbonyl (PABC) group, which has the structure shown below:

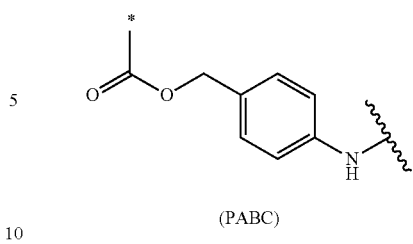

(PABC)

In some instances a PABA group may be preferable over a PABC group, as being more hydrolytically stable.

In a preferred embodiment, the group $R^{31}$ is

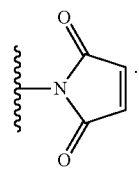 [SMILES: *N1C(=O)C=CC1=O]

In another preferred embodiment, the group $R^{31}$ is

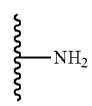

or $R^{31}$ is H while v is 0 and s is 1. In each case, the result is a seco-CPI-linker compound that has an amino-terminal group, of the structure

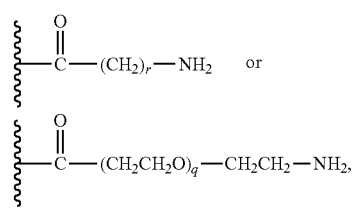

respectively, which is suitable as an amine donor for a transglutaminase-mediated conjugation.

Preferred type (a) seco-CPI-linker compounds are according to formula (IIIa')

(IIIa')

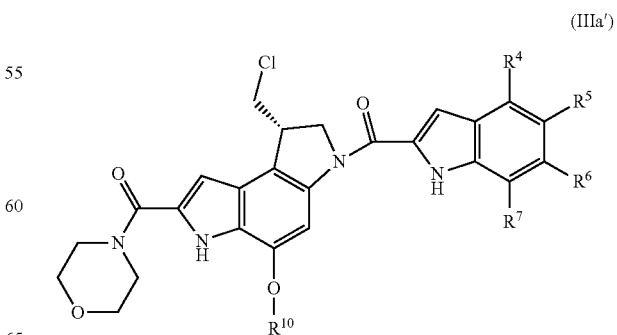

where
$R^4$, $R^5$, $R^6$, and $R^7$ are as defined in respect of formula (I) the BRIEF SUMMARY OF THE INVENTION section hereinabove;
$R^{10}$ is

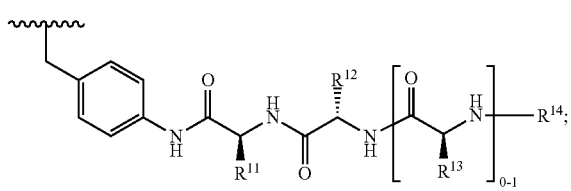

$R^{11}$, $R^{12}$ and $R^{13}$ are independently H, CH$_3$, CH(CH$_3$)$_2$, CH$_2$CO$_2$H, CH$_2$CH$_2$CO$_2$H, CH$_2$C(=O)NH$_2$, CH$_2$CH$_2$C(=O)NH$_2$, (CH$_2$)$_4$NH$_2$, (CH$_2$)$_3$NHC(=NH)NH$_2$ or (CH$_2$)$_3$NHC(=O)NH$_2$ (that is, $R^{11}$, $R^{12}$, and $R^{13}$ correspond to the side chain residues of the amino acids glycine, valine, aspartic acid, glutamic acid, asparagine, glutamine, lysine, arginine, and citrulline); and
$R^{14}$ is

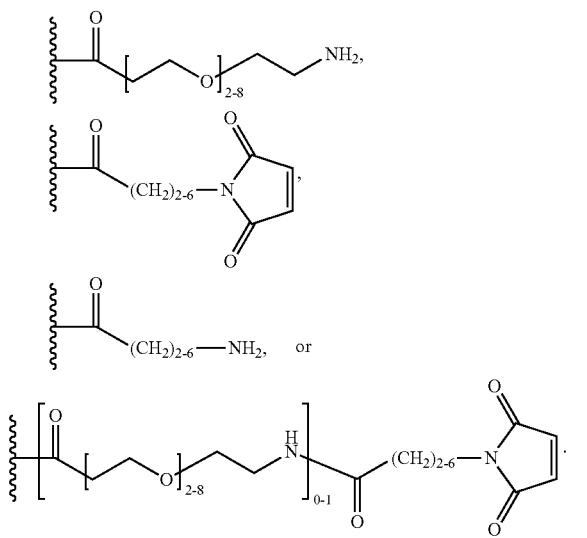

Preferably, the peptide in $R^{10}$ is a dipeptide—i.e., the suffix associated with the amino acid HO$_2$CCH(R$^{13}$)NH$_2$ in the peptide is zero—corresponding to the formula

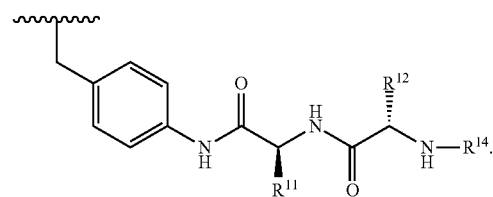

Specific compounds according to formula (IIIa') are shown in Table III, where $R^4$, $R^6$, and $R^7$ are H unless noted otherwise and $R^{10}$ is A or B:

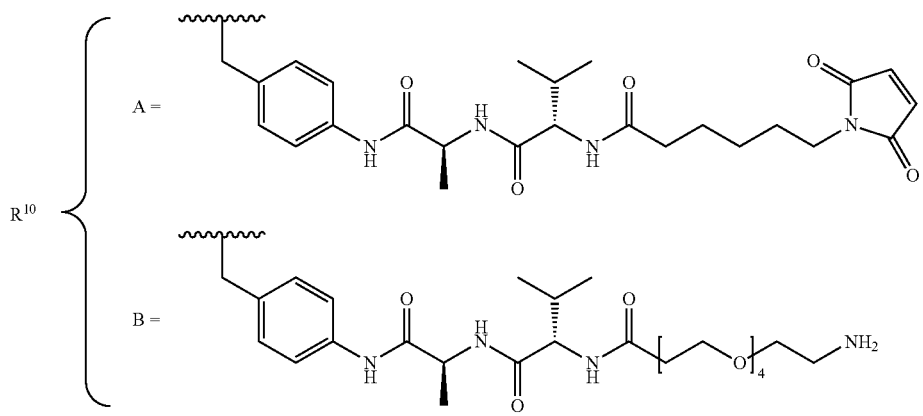

TABLE III seco-CPI-Linker Compounds

| seco-CPI-Linker | $R^{10}$ | $R^5$ |
|---|---|---|
| IIIa-01 | A | —O—CH$_2$CH$_2$—NMe$_2$ |
| IIIa-02 | A | —NH—C(O)—C$_6$H$_4$—NH$_2$ |
| IIIa-03 | A | —O—CH$_2$CH$_2$—O—CH$_3$ |
| IIIa-04 | A | —O—CH$_2$CH$_3$ |
| IIIa-05 | B | —O—CH$_2$CH$_2$—O—CH$_3$ |

TABLE III-continued
seco-CPI-Linker Compounds
| seco-CPI-Linker | $R^{10}$ | $R^5$ |
|---|---|---|
| IIIa-06 | B | 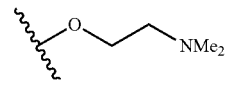 [SMILES: *OCCN(C)C] |
| IIIa-07 | B | 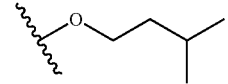 [SMILES: *OCCC(C)C] |
| IIIa-08 | B | 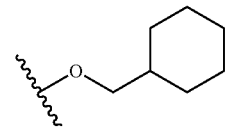 [SMILES: *OCC1CCCCC1] |
| IIIa-09 | B |  ($R^4$ = H, $R^6$ = $R^7$ = OMe) |
| IIIa-10 | B | 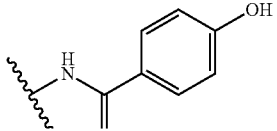 |
| IIIa-11 | B | 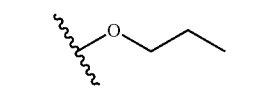 [SMILES: *OCCC] |
| IIIa-12 | B | 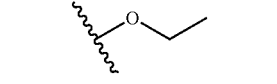 [SMILES: *OCC] |
| IIIa-13 | A | 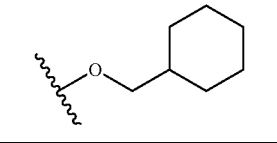 |
A preferred seco-CPI-linker compound is (IIIa-06), whose complete structure is shown following:
(IIIa-06)
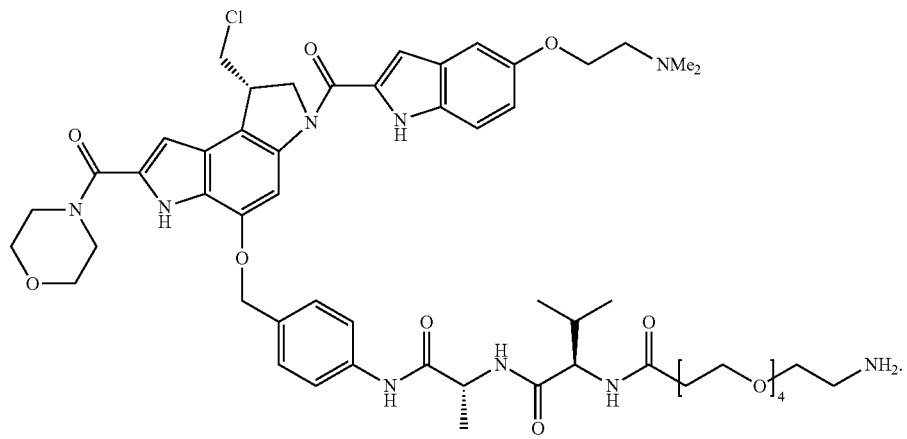
A preferred seco-CPI-linker compound is (IIIa-09), whose complete structure is shown following:
(IIIa-09)
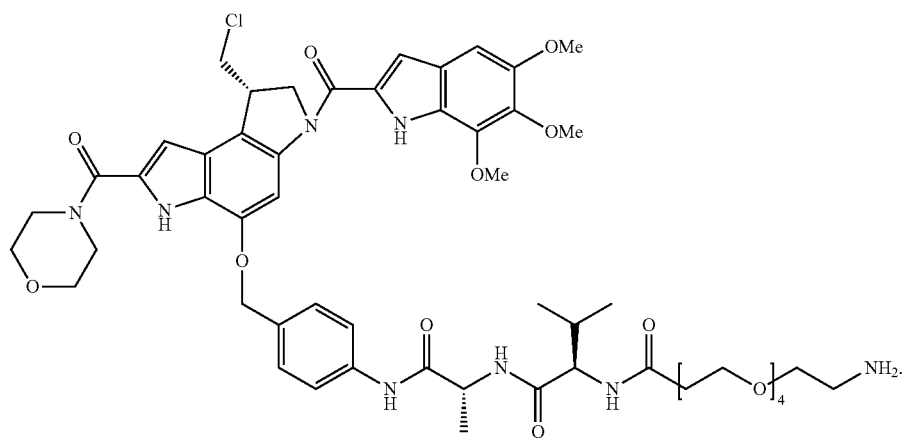

A preferred seco-CPI-linker compound is (IIIa-12), whose complete structure is shown following:

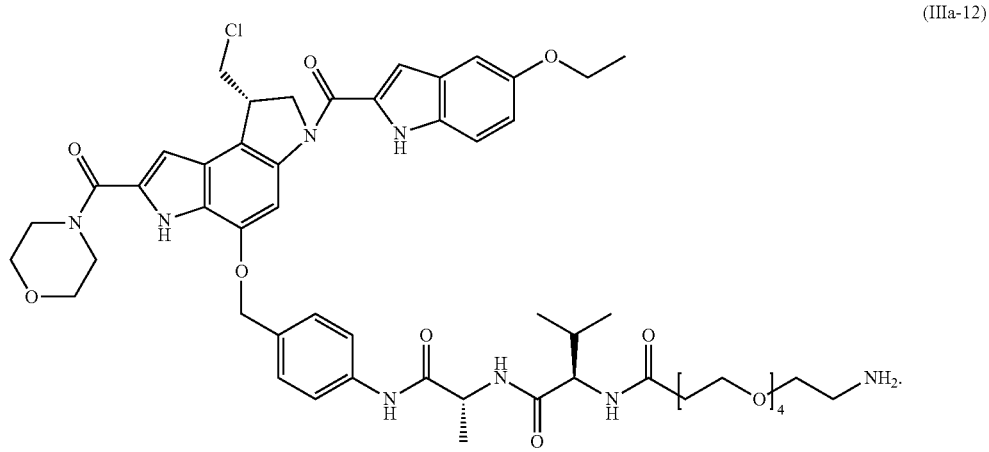
(IIIa-12)

seco-CPI-linker compounds having a A-type linkers are designed for conjugation via a Michael addition reaction with a thiol group on the antibody, as discussed above. Those having a B-type linker are designed for transglutaminase mediated conjugation, again as discussed above.

More preferably, in formula (IIIa') $R^4$, $R^6$, and $R^7$ are each H; and $R^5$ is

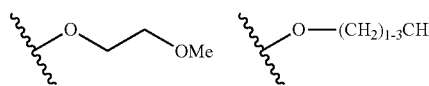

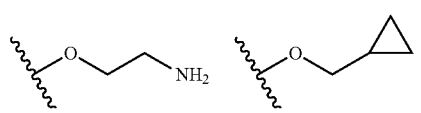

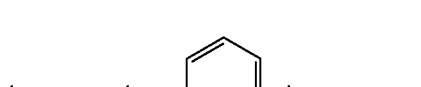

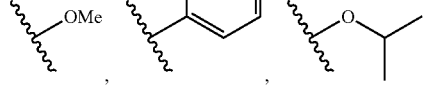

-continued

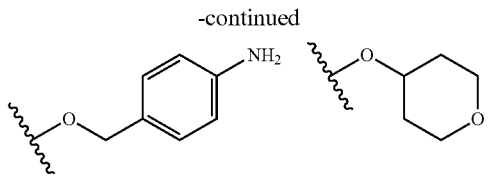

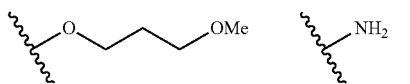

or

Conjugates

In one embodiment, conjugates of this invention are derived from type (a) seco-CPI-linker compounds and can be represented by the formula (IVa):

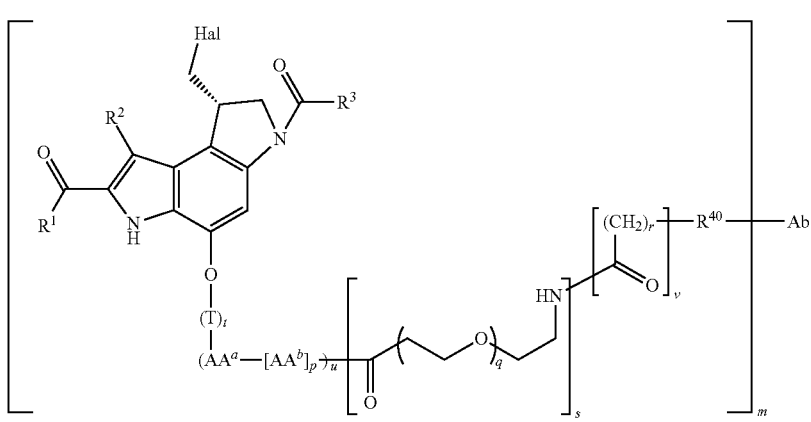

wherein

Ab is an antibody;

$R^{40}$ is a bond,

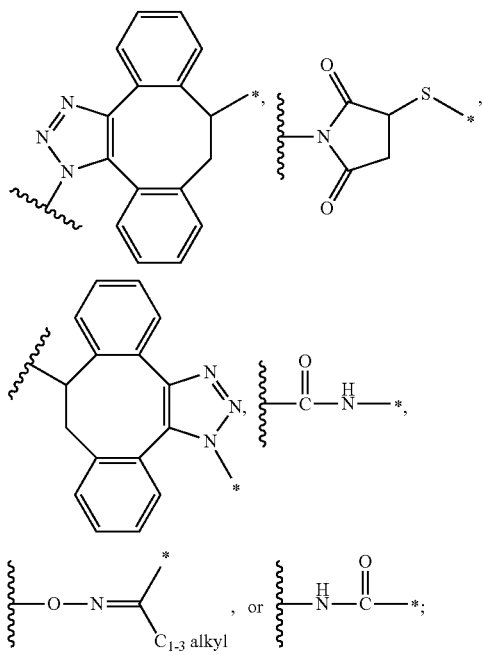

where the open valence of $R^{40}$ that is bonded to Ab is denoted by an asterisk (*) and the open valence of $R^{40}$ that is bonded to $(CH_2)_r$ is denoted by a wavy line (〰);

m is 1, 2, 3, or 4;

v is 0 or 1, with the provisos that v can be 0 only if s is 1 and $R^{40}$ is a bond and that $R^{40}$ can be a bond only if v is 0 and s is 1;

T, t, $AA^a$, $AA^b$, u, p, q, s, r, and $X^A$ are as defined in respect of formula (IIIa); and $R^1$, $R^2$, and $R^3$ are as defined in the BRIEF SUMMARY OF THE INVENTION section hereinabove.

Where $R^{40}$ is a bond, the nitrogen in

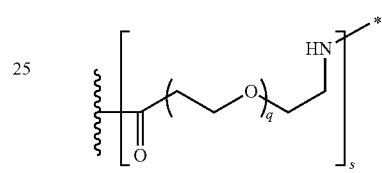

is bonded to directly antibody Ab, per the formula below:

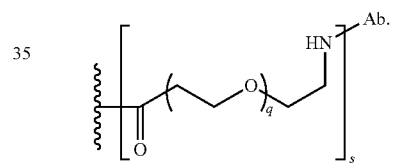

In one embodiment of conjugates according to formula (IVa), $R^3$ is

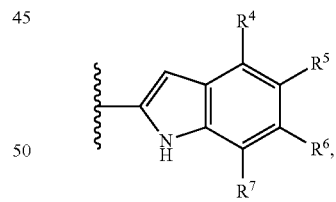

especially where $R^4$, $R^6$, and $R^7$ are each H.

In a preferred embodiment, u is 1 in formula (IVa).

In formula (IVa), if the subscripts t and u are both 0, then the linker is of the non-cleavable type and relies on degradation of the antibody Ab to release the drug. The polyethylene glycol component optionally may be present (i.e., s is 1) if its presence is beneficial, for example by increasing the solubility of the drug-linker compound during conjugation and does not interfere with the biological activity of the drug.

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, poly-glycolic acid, collagen, polyorthoesters, and polylactic acid. See, e.g., *Sustained and Controlled Release Drug Delivery Systems,* J. R. Robinson, ed., Marcel Dekker, Inc., New York, 1978.

Administration can be via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; Ranade, *J. Clin. Pharmacol.* 1989, 29, 685; Umezawa et al., *Biochem. Biophys. Res. Commun.* 1988, 153, 1038; Bloeman et al., *FEBS Lett.* 1995, 357, 140; Briscoe et al., *Am. J. Physiol.* 1995, 1233, 134; Schreier et al., *J. Biol. Chem.* 1994, 269, 9090; Keinanen and Laukkanen, *FEBS Lett.* 1994, 346, 123; and Killion and Fidler, *Immunomethods* 1994, 4, 273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colo-rectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immuno-modulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxo-rubicin, duocarmycin, dynemycin A, epothilones, etoposide, floxuridine, fludarabine, 5-fluoro-uracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, nivolumab, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation.

Example 1

Conjugation by Michael Addition

This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at room temperature ("RT," circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the seco-CPI-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols. The sample is then filtered via a 0.2µ filter The material is buffer exchanged via TFF VivaFlow 50 Sartorius 30 MWCO PES membrane into 10 mg/mL glycine, 20 mg/mL sorbitol, 15% acetonitrile ("ACN") pH 5.0 (5×TFF buffer exchange volume), to remove any unreacted drug. The final formulation is carried out by TFF into 20 mg/mL sorbitol, 10 mg/mL glycine, pH 5.0.

Example 2

Transglutaminase-Mediated Conjugation

The following procedure can be used for transglutaminase mediated conjugation of seco-CPI-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5. The eluted fractions are neutralized with 1M Tris pH 9.0. The conjugated can be formulated in 20 mg/mL Sorbitol, 10 mg/mL Glycine, pH 5.0.

Those skilled in the art will understand that the conditions and methodologies in these two examples are illustrative and non-limiting and that variations thereof or other approaches for conjugation are known in the art and usable in the present invention.

Example 3

Properties of Seco-CPI Compounds

Table IV shows properties of compounds of this invention, including proliferation inhibition efficacy against various human cancer cell lines and CLogP. Proliferation inhibition was measured using a 72 hr ATP luminescence assay (Cheng et al., U.S. Pat. No. 8,394,922 B2 (2013)).

Proliferation inhibition was measured against: (a) H226 (human mesothelioma (lung) cancer cell line); (b) N87 (human gastric (stomach) cancer cell line); (c) OVCAR3 (human ovarian cancer cell line); (d) HCT116 (human colon cancer cell line); and (e) HCT116/VM46 (multidrug and paclitaxel resistant subline of HCT116).

TABLE IV

Properties of seco-CPI Compounds

| Cpd. No. | Proliferation Inhibition of Cancer Cells (Cell Line & $EC_{50}$, nM) | | | | | CLogP |
|---|---|---|---|---|---|---|
| | H226 | N87 | OVCAR3 | HCT116 | HCT116/ VM46 | |
| Ia-01 | 0.014 | 0.007 | — | — | — | 1.81 |
| Ia-02 | 0.042 | 0.097 | 0.048 | 0.045 | 0.045 | 2.45 |
| Ia-03 | 0.038 | 0.048 | 0.026 | 0.034 | 0.034 | 2.97 |
| Ia-04 | 0.11 | 0.15 | 0.11 | 0.12 | 0.12 | 2.89 |
| Ia-05 | 0.18 | 0.21 | 0.076 | 0.17 | 0.17 | 3.37 |
| Ia-06 | 0.47 | 0.56 | 0.32 | 0.36 | 0.36 | 2.83 |
| Ia-07 | 0.72 | 0.81 | 0.41 | 0.67 | 0.67 | 3.41 |
| Ia-08 | 3.4 | 1.3 | 2.1 | — | — | 1.04 |
| Ia-09 | 0.055 | 0.016 | 0.025 | — | — | 2.19 |
| Ia-10 | 0.25 | 0.15 | — | — | — | 4.57 |
| Ia-11 | 1.0 | 1.2 | 0.52 | 0.58 | 0.92 | 1.92 |
| Ia-12 | 0.53 | 1.3 | 0.54 | 0.40 | 0.29 | 3.68 |
| Ia-13 | 0.32 | 0.48 | 0.12 | 0.18 | 0.24 | 2.75 |
| Ia-14 | 0.43 | 0.36 | 0.10 | 0.26 | 0.77 | 1.55 |
| Ia-15 | 0.28 | 0.32 | 0.21 | 0.22 | 0.26 | 3.39 |
| Ia-16 | 0.40 | 0.50 | — | — | — | 2.01 |
| Ia-17 | 1.6 | 36 | 18 | 19 | 25 | 1.42 |
| Ia-18 | 32 | 48 | 12 | 25 | 19 | 1.12 |
| Ia-19 | 4.2 | 3.1 | 1.1 | 3.2 | 3.5 | 0.78 |
| Ia-20 | 6.5 | 3.5 | 1.5 | 1.9 | 2.6 | 2.36 |
| Ia-21 | 0.99 | 2.2 | 1.2 | 0.85 | 0.50 | 1.81 |
| Ia-22 | 5.1 | 1.9 | 1.1 | 1.2 | 1.2 | 1.65 |
| Ia-23 | 7.5 | 2.6 | 1.1 | 0.9 | 1.9 | 2.42 |
| Ia-24 | 250 | — | 250 | 250 | 250 | 1.60 |
| Ia-25 | 23 | 38 | 22 | 13 | 24 | 0.78 |
| Ia-26 | 9.5 | — | 2.7 | 4.1 | 12 | 1.34 |
| Ia-27 | 1.4 | 3.5 | — | — | — | 3.37 |
| Ia-28 | 0.30 | 0.066 | 0.058 | 0.079 | 0.090 | 2.85 |
| Ia-29 | 0.63 | 0.26 | — | — | — | 2.60 |
| Ia-30 | 0.018 | 0.045 | 0.032 | 0.033 | 0.097 | 1.11 |
| Ia-31 | 0.24 | 0.43 | 0.53 | 0.62 | 0.86 | 3.90 |
| Ib-01 | 2.39 | 3.6 | 2.8 | 3.2 | 3.5 | 1.92 |
| Ib-02 | 1.0 | 0.96 | 0.53 | 0.64 | 1.9 | 1.83 |
| Ic-01 | 0.91 | 1.5 | 0.89 | 0.43 | 0.75 | 1.93 |
| Id-01 | — | 2.3 | 1.1 | 0.93 | — | 2.18 |
| Id-02 | 1.2 | 1.4 | — | — | — | 1.60 |

Example 4

Compound 10

This example and FIG. 1A relate to the synthesis of compound 10.

A solution of 3,5-dinitrobenzyl alcohol 1 (5 g, 25.2 mmol) in EtOAc (160 mL) was added to 2-iodoxybenzoic acid ("SIBX,", available from Sigma-Aldrich, 17.67 g, 63.1 mmol). The reaction mixture was refluxed at 90° C. for 20 h, cooled to RT and filtered. The solid was discarded and the filtrate was concentrated by under vacuum to yield crude product 2 as a yellow solid, which was dissolved in 100 mL of EtOAc and washed with saturated $NaHCO_3$ solution and then water. Then it was dried over anhydrous $Na_2SO_4$. The solution was concentrated under vacuum to provide 4.2 g (81%) of 3,5-dinitrobenzaldehyde 2 as a yellow solid. $^1H$ NMR (500 MHz, DMSO-$d_6$) δ 10.24 (s, 1H), 9.08-9.06 (m, 1H), 9.04 (d, J=2.0 Hz, 2H); Anal. Calcd. for $C_7H_4N_2O_5$: 196.01; found 194.99 $[M-H]^+$.

A stirred solution of syn-benzaldehyde oxime (6.18 g, 51.0 mmol) in N,N-dimethyl-formamide ("DMF," 50 mL) was treated with $K_2CO_3$ (14.38 g, 102 mmol) and stirred for 10 min. A solution of 3,5-dinitrobenzaldehyde 2 (5 g, 25.5 mmol) in DMF (50 mL) was added. The reaction mixture was stirred for 2 h at 90° C. and cooled to RT. (Bromomethyl)benzene (7.12 mL, 58.6 mmol) was added to the reaction mixture, which was then stirred for 18 h. The reaction mixture was diluted with $Et_2O$ (200 mL). Aqueous HCl (1 N, 100 mL) was added slowly with stirring. The ether layer was collected and the aqueous layer was extracted with $Et_2O$ (80 mL×2) and EtOAc (80 mL). The combined organic layers were washed with saturated $NaHCO_3$ solution and then brine, and dried over by $MgSO_4$, filtered, and concentrated under vacuum to yield 16 g of a brown oil which was purified on a 330 g column from Biotage (45 to 55% dichloromethane/hexane) to provide 3.41 g (52.1%) of 3-(benzyloxy)-5-nitrobenzaldehyde 3 as a white solid. $^1H$ NMR (500 MHz, chloroform-d) δ 10.07 (s, 1H), 8.37-8.29 (m, 1H), 8.10 (t, J=2.2 Hz, 1H), 7.82 (dd, J=2.4, 1.2 Hz, 1H), 7.53-7.36 (m, 5H), 5.24 (s, 2H); Anal. Calcd. for $C_{14}H_{11}N_1O_4$: 257.0; found 279.3 $[M+Na]^+$.

Sodium methanolate (25%) (1.313 mL, 5.91 mmol) was added dropwise to a stirred solution of 3-(benzyloxy)-5-nitrobenzaldehyde 3 (400 mg, 1.555 mmol) and methyl 2-azido-acetate 4 (available from Sigma-Aldrich, 591 mg, 5.13 mmol) in a mixture of tetrahydrofuran ("THF," 3 mL) and MeOH (3 mL) at −25° C. over 20 min. The reaction mixture was stirred for 64 h at −20° C. and then 0° C. for 1 h. The reaction mixture was poured into a mixture of ice and water, extracted with dichloromethane ("DCM," 15 mL×3), washed with water, and then brine. The organic layer was dried over $MgSO_4$ to yield a crude product which was purified on a 330 g column from Biotage (5% to 9% EtOAc/Hex,) to provide 323 mg (58.6%) of compound 5: $^1$H NMR (500 MHz, chloroform-d) δ 8.22 (s, 1H), 7.84 (s, 1H), 7.80 (t, J=2.1 Hz, 1H), 7.53-7.33 (m, 5H), 6.86 (s, 1H), 5.20 (s, 2H), 3.96 (s, 3H); 13C NMR (126 MHz, chloroform-d) δ 163.4, 159.1, 149.2, 135.6, 135.3, 128.8, 128.5, 128.2, 127.6, 122.8, 122.0, 118.0, 109.8, 70.9, 53.3; Anal. Calcd. for $C_{17}H_{14}N_4O_5$: 354.09; found 377.30 [M+Na]+.

Compound 5 (313 mg, 0.883 mmol) was added to xylene (80 mL) and sonicated for 5 min. A homogenous solution formed, which was degassed twice. The reaction mixture was refluxed for 20 h at 160° C. and cooled to RT. The xylene was evaporated under vacuum to yield a yellow solid which was purified on a 24 g column from Biotage (5% to 15% EtOAc/Hexane) to provide 47.3 mg (16.41%) of compound 6a and 160.3 mg (55.6%) of compound 6b.

Compound 6a: $^1$H NMR (500 MHz, chloroform-d) δ 10.19 (br. s., 1H), 8.06 (d, J=2.2 Hz, 1H), 7.63 (d, J=1.9 Hz, 1H), 7.52-7.47 (m, 2H), 7.44 (t, J=7.4 Hz, 2H), 7.41-7.35 (m, 1H), 5.20 (s, 2H), 4.01 (s, 3H); $^{13}$C NMR (126 MHz, chloroform-d) δ 161.2, 152.7, 136.2, 133.2, 131.2, 130.5, 128.8, 128.3, 127.6, 125.6, 115.2, 112.0, 108.9, 71.5, 52.4; Anal. Calcd. for $C_{17}H_{14}N_2O_5$: 327.1; found 327.3 [M+H]+.

Compound 6b: 1H NMR (500 MHz, chloroform-d) δ 9.38 (br. s., 1H), 8.38 (s, 1H), 7.75 (d, J=1.3 Hz, 1H), 7.57-7.51 (m, 2H), 7.51-7.42 (m, 3H), 7.38 (d, J=2.0 Hz, 1H), 5.32 (s, 2H), 3.99 (s, 3H); 13C NMR (126 MHz, chloroform-d) δ 161.4, 145.2, 143.3, 135.3, 130.9, 129.7, 128.9, 128.8, 128.2, 126.7, 113.2, 111.0, 100.5, 71.1, 52.4; Anal. Calcd. for $C_{17}H_{14}N_2O_5$: 327.1; found 327.3 [M+H]+.

To a stirred solution of compound 6b (150 mg, 0.460 mmol) in THF (4 mL) was added Boc-anhydride (0.192 mL, 0.827 mmol) and 4-dimethylaminopyridine ("DMAP," 11.23 mg, 0.092 mmol). The reaction mixture was stirred for 18 h at RT. Brine (5 mL) and EtOAc (5 mL) were added and stirring was continued for 5 min. The organic layer was collected. The aqueous layer was extracted with 10 mL of EtOAc. The combined organic layers were dried over MgSO$_4$, filtered, and concentrated under vacuum to yield a yellow solid which was purified on a 24 g column from Biotage (5% to 40% EtOAc/Hexane) to provide 184.2 mg (94%) of compound 7: 1H NMR (500 MHz, chloroform-d) δ 8.29 (d, J=1.7 Hz, 1H), 7.70 (d, J=1.6 Hz, 1H), 7.50 (d, J=7.3 Hz, 2H), 7.45-7.39 (m, 2H), 7.39-7.33 (m, 2H), 5.35 (s, 2H), 3.97 (s, 3H), 1.50 (s, 9H); 13C NMR (126 MHz, chloroform-d) δ 160.4, 149.2, 145.5, 143.5, 135.1, 130.1, 130.0, 128.8, 128.6, 128.1, 126.3, 112.6, 112.4, 102.1, 86.4, 71.2, 52.4, 27.2; Anal. Calcd. for $C_{22}H_{22}N_2O_7$: 426.1; found 449.4 [M+Na]+.

Zinc powder (130 mg, 1.982 mmol) and NH$_4$Cl (212 mg, 3.96 mmol) were added to a stirred solution of compound 7 (169 mg, 0.396 mmol) in acetone (4 mL)/water (0.800 mL). The reaction mixture was stirred for 18 hour at RT. The reaction mixture was concentrated under vacuum to yield 180 mg crude compound 8, which was re-dissolved in EtOAc (8 mL), washed with water (8 mL) and then brine (8 mL), and dried over MgSO$_4$. It was concentrated under vacuum to yield 160 mg crude compound 8 (brown) which was purified on a 12 g column from Biotage (15% to 35% EtOAc/Hexane) to provide 138.1 mg (88%) of compound 8: $^1$H NMR (500 MHz, chloroform-d) δ 7.46 (d, J=7.3 Hz, 2H), 7.39 (t, J=7.4 Hz, 2H), 7.35-7.30 (m, 1H), 7.03 (s, 1H), 6.50 (d, J=1.4 Hz, 1H), 6.29 (d, J=1.4 Hz, 1H), 5.22 (s, 2H), 3.91 (s, 3H), 3.53 (br. s., 2H), 1.49 (s, 9H); Anal. Calcd. for $C_{22}H_{24}N_2O$: 397.17; found 397.13 [M+H]+.

Boc-anhydride (0.112 mL, 0.484 mmol was added to a stirred solution of compound 8 (128 mg, 0.323 mmol) in THF (3.5 mL). The reaction mixture was stirred for 20 h at RT and concentrated under vacuum to yield 178 mg of brown, waxy crude compound 9, which was purified on a 12 g column from Biotage (5% to 15% EtOAc/Hexane) to provide 156 mg (97%) compound 9: $^1$H NMR (500 MHz, chloroform-d) δ 7.48 (d, J=7.3 Hz, 2H), 7.39 (t, J=7.4 Hz, 2H), 7.36-7.30 (m, 2H), 7.13 (s, 1H), 6.86 (s, 1H), 6.41 (br. s., 1H), 5.24 (s, 2H), 3.92 (s, 3H), 1.54 (s, 9H), 1.47 (s, 9H). Anal. Calcd. for $C_{27}H_{32}N_2O_7$: 496.2; found 497.5 [M+H]+.

N-Iodosuccinimide (127 mg, 0.564 mmol) and acetic acid (0.065 mL, 1.128 mmol) were added to a stirred solution of compound 9 (140 mg, 0.282 mmol) in toluene (8 mL). The reaction flask was covered with aluminum foil and stirred for 18 h at RT. The reaction mixture was poured into water (20 mL). EtOAc (10 mL) was added and the mixture was stirred for 2 min. The organic layer was collected. The aqueous layer was extracted with EtOAc (10 mL). The combined organic layers were dried with MgSO$_4$, filtered, and concentrated under vacuum to yield a dark purple wax which was purified on a 12 g column from Biotage (5% to 12% EtOAc/Hexane) to provide 110.6 mg (63.0%) compound 10 as yellow wax: $^1$H NMR (500 MHz, chloroform-d) δ 7.81 (br. s., 1H), 7.50 (d, J=7.1 Hz, 2H), 7.43-7.36 (m, 2H), 7.35-7.30 (m, 1H), 7.12 (s, 1H), 6.79 (br. s., 1H), 5.27 (s, 2H), 3.94 (s, 3H), 1.56 (s, 9H), 1.43 (s, 9H); Anal. Calcd. for $C_{27}H_{31}IN_2O_7$: 622.1; found 623.4 [M+H]+.

Example 5

Ester 12

Figure 3A:
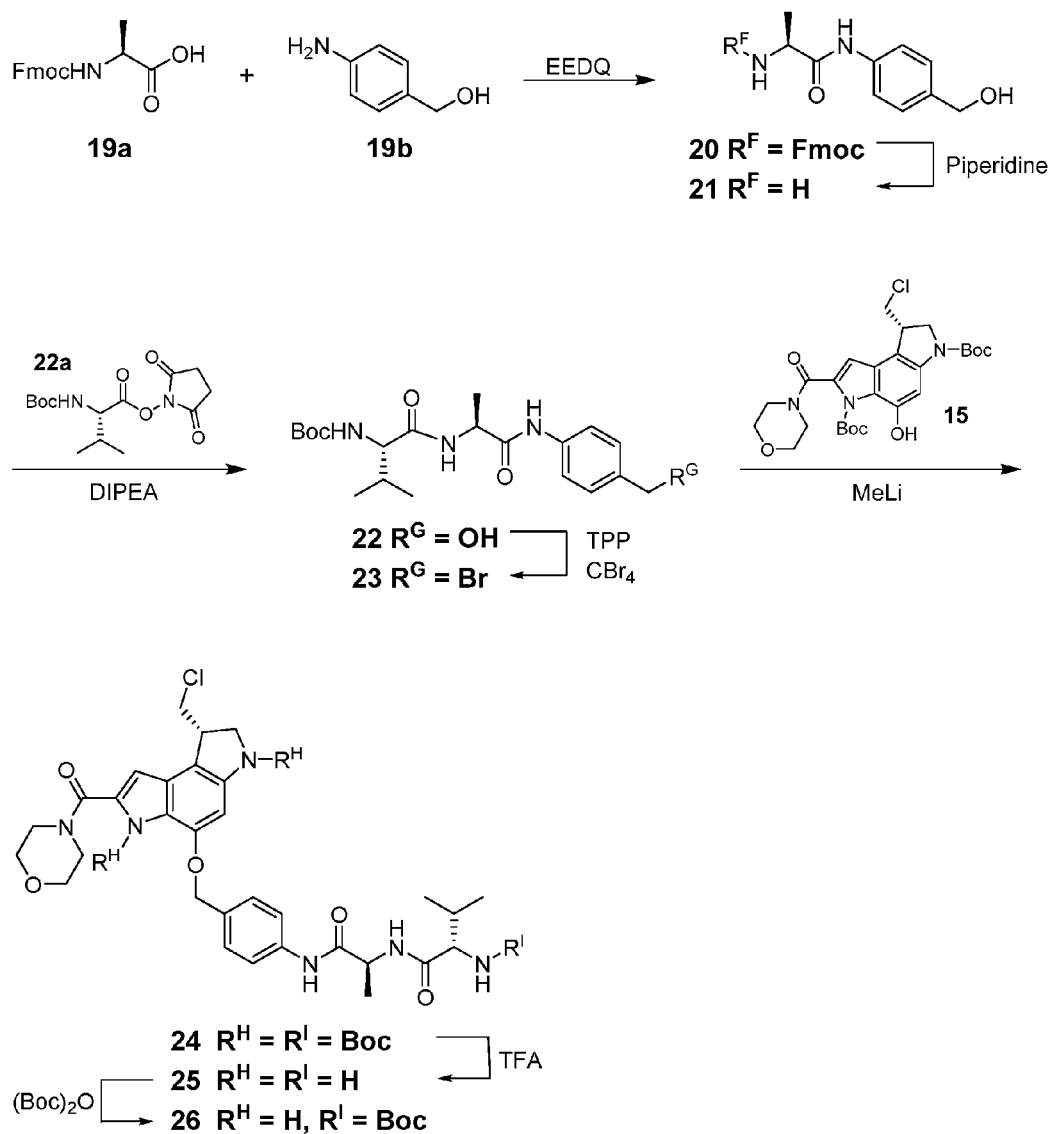
Figure 3B:
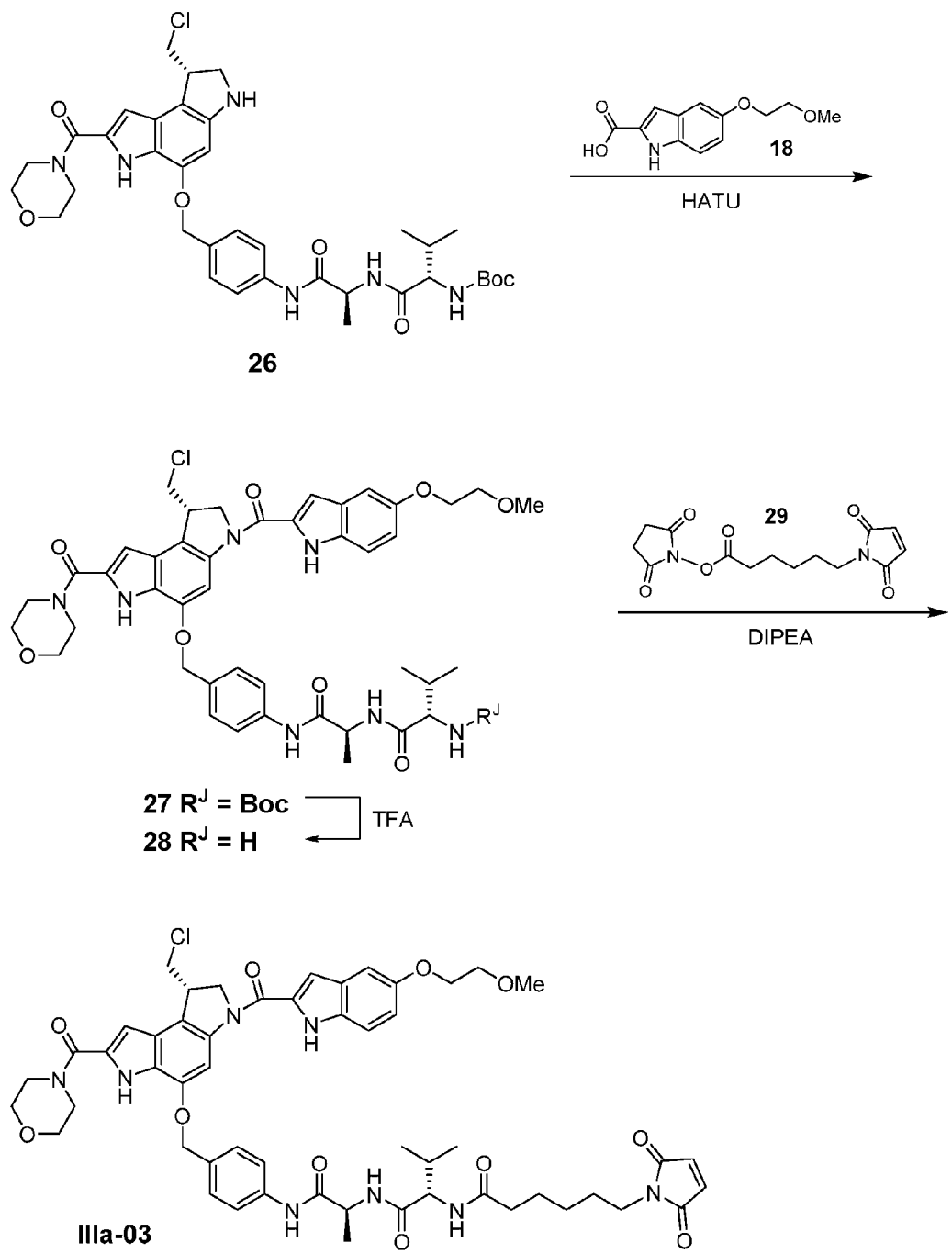

This example and FIG. 3B relate to the preparation of ester 12.

NaH (7.71 mg, 0.193 mmol) and 1,3-dichloropropene (23.50 µl, 0.241 mmol) were added to a stirred solution of compound 10 (100 mg, 0.161 mmol) in DMF at 0° C. The reaction mixture was stirred for 3 h. The reaction mixture was poured into a saturated NH$_4$Cl 100 mL) solution and extracted with Et$_2$O (2×80 mL). The extract was dried over MgSO$_4$, filtered, and concentrated under vacuum to yield a brown wax which was purified on a 12 g column from Biotage (5% to 12% EtOAc/Hexane) to provide 88.7 mg (79%) of compound 11: $^1$H NMR (500 MHz, chloroform-d) δ 7.47-7.31 (m, 5H), 7.21 (s, 1H), 6.53 (d, J=18.3 Hz, 1H), 6.03-5.83 (m, 3H), 5.34-5.21 (m, 2H), 3.96 (s, 2H), 4.57-3.70 (m, 2H), 1.58 (s, 9H), 1.30 (d, J=9.8 Hz, 9H). Anal. Calcd. for $C_{30}H_{34}ClIN_2O_7$: 696.1; found 719.5 [M+Na]+.

Tri-n-butyltin hydride (1.793 mL, 6.59 mmol) and 2,2'-azobis(2-methylpropionitrile) ("AIBN," 0.085 g, 0.507 mmol) were added to a stirred solution of compound 11 (3.5305 g, 5.07 mmol) in benzene (100 mL). The reaction mixture was degassed once and stirred for 4 h at 80° C. The reaction mixture was cooled to RT under vacuum to yield a brown wax that was purified on a 120 g column from Biotage (5% to 10% EtOAc/Hexane) to provide 2.7552 g mixture of compounds 12 and 12a. The mixture was separated by SFC chiral separation: Chiralpak: AD-H preparative column, 30×250 mm, 5 m; Mobile Phase: 35% MeOH in CO$_2$ at 130 bar; temperature: 35° C.; Flow rate: 70.0 mL/min for 13 min; UV monitored at 220 nm. This procedure provided 0.9562 g (33.1%) of compound 12. $^1$H NMR (500 MHz, chloroform-d) δ 7.52-7.30 (m, 6H), 7.11 (s, 1H), 5.27 (s, 2H), 4.20-4.13 (m, 1H), 4.01-3.82 (m, 6H), 3.53 (t, J=9.9 Hz, 1H), 1.57 (s, 9H), 1.43 (br. s., 9H). Anal. Calcd. for: $C_{30}H_{35}ClN_2O_7$ 570.2; found 571.5 [M+H]+; [α]$^{20}$D −17.06

(c 2.45, CHCl$_3$) and 0.9252 g (32.0%) of compound 12b. $^1$H NMR (500 MHz, chloroform-d) δ 7.53-7.30 (m, 6H), 7.11 (s, 1H), 5.27 (s, 2H), 4.22-4.13 (m, 1H), 4.12-3.83 (m, 6H), 3.53 (t, J=10.1 Hz, 1H), 1.57 (s, 9H), 1.43 (br. s., 9H). Anal. Calcd. for C$_{30}$H$_{35}$ClN$_2$O$_7$: 570.2; found 571.5 [M+H]+; [α]$^{20}$D+17.06 (c 2.45, CHCl$_3$).

Example 6

Compound 16

Figure 2:
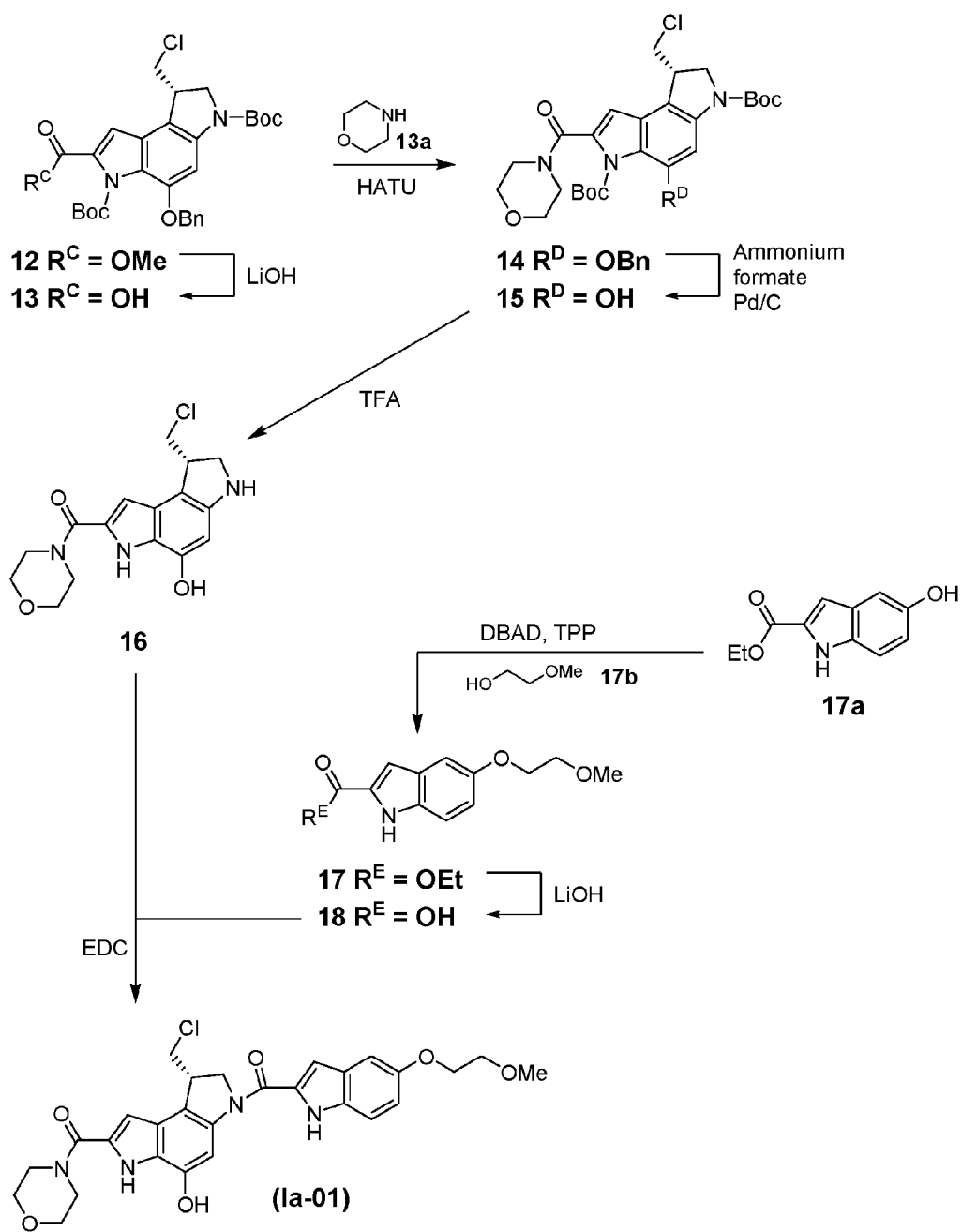

This example and FIG. 2 relate to the preparation of compound 16.

A solution of ester 12 (1 g, 1.751 mmol) in ACN (Aldrich, 40 mL) was prepared. LiOH (0.125 g, 5.22 mmol) in distilled water (10 mL) was added. The reaction mixture was stirred at 50° C. for 2 h. LCMS analysis showed the reaction to be complete. The reaction mixture was acidified with 6 N HCl to pH 4 and concentrated under vacuum to remove the ACN. The reaction mixture was extracted with EtOAC (2×50 mL). The organic phases were washed with water and brine, dried with anhydrous Na$_2$SO$_4$, and concentrated and dried under high vacuum overnight to yield crude acid 13 (0.98 g). ESI-LCMS (M+H): 557.0.

N,N-Diisopropylethylamine ("DIPEA," Aldrich, 0.612 mL, 3.50 mmol) was added to a solution of acid 13 (0.98 g), morpholine 13a (Aldrich, 0.458 g, 5.25 mmol) and N,N,N',N'-tetramethyl-O-(7-azabenzotriazol-1-yl)uronium hexafluorophosphate ("HATU", CAS Reg. No. 148893-10-1, Oakwood Chemical, 0.999 g, 2.63 mmol) in anhydrous DMF (Acros, 5 mL). The reaction mixture was stirred at RT for 45 min. LCMS analysis showed the reaction to be complete. The reaction mixture was worked up with EtOAc, water and brine. The organic phases were combined and concentrated with 2 g of silica gel to a slurry. The slurry was purified on a 24 g COMBIFLASH™ column, eluting with 0-35% EtOAc in hexane gradient. The fractions expected to contain product were combined, concentrated and dried under high vacuum to yield compound 14 as a solid (0.872 g, 80% yield over two steps). ESI-LCMS (M+H): 626.1.

A solution of compound 14 (396 mg, 0.633 mmol) in anhydrous THF (Acros, 5 mL) was prepared. Ammonium formate (Aldrich, 1.104 g, 8.76 mmol) in distilled water (1 mL) was added. Nitrogen gas was bubbled through the reaction mixture for 5 min and then Pd on carbon (Aldrich-Sigma, 10%, 60 mg) was added. The reaction mixture was stirred at RT for 0.5 h. LCMS analysis showed the reaction to be complete. The reaction mixture was diluted with EtOAC (50 mL) and filtered. The filtrate was washed with water and brine, dried over anhydrous Na$_2$SO$_4$, and concentrated in vacuo to leave a residue, which was freeze-dried with ACN and water to yield compound 15 (white solid, 225 mg, 66% yield). ESI-LCMS (M+H): 536.2.

Trifluoroacetic acid ("TFA," Aldrich, 1 mL) was added to a solution of compound 15 (78 mg, 0.146 mmol) in anhydrous DCM (Acros, 1 mL). The reaction mixture was stirred at RT for 30 min. LCMS analysis showed the reaction to be complete. The reaction mixture was concentrated under vacuum and freeze-dried with ACN and water to yield compound 16 as green solid (81 mg, double TFA salt, 98%). ESI-LCMS (M+H): 336.0.

Example 7

Compound 18

This example relates to the preparation of compound 18, as shown in FIG. 2.

A solution of ethyl ester 17a (Alfa Aesar, 300 mg, 1.46 mmol) and triphenyl-phosphine ("TPP," Aldrich-Sigma, 767 mg, 2.92 mmol) in anhydrous THF (Acros Organics, 10 mL) was prepared. Di-tert-butyl azodicarboxylate ("DBAD," Aldrich, 673 mg, 2.92 mmol) in anhydrous THF (Acros, anhydrous, 2 mL) was added dropwise over 10 min, followed by 2-methoxyethanol 17b (Aldrich, 445 mg, 5.85 mmol). The reaction mixture was stirred at RT overnight. LCMS analysis showed the reaction was almost complete. The reaction mixture was worked up with EtOAc, water, and brine. The organic phases were combined and concentrated with silica gel (1 g) under vacuum to yield a slurry. The slurry was purified on 24 g COMBIFLASH™ column, eluting with 0-30% EtOAc in hexane gradient. The fractions expected to contain product were combined and concentrated and dried under high vacuum to yield compound 17 as a solid (314 mg, 1.19 mmol, 82%). ESI-LCMS (M+H): 264.1.

LiOH (Aldrich, 50 mg) in distilled water (1 mL) was added to a solution of compound 17 (314 mg, 1.19 mmol) in ACN (Acros, 10 mL). The reaction mixture was stirred at 40° C. for 3 h. LCMS analysis showed the reaction to be complete. The reaction mixture was neutralized with acetic acid (0.5 mL) and concentrated under vacuum to 2 mL. The resultant mixture was loaded on a COMBIFLASH™ AQ Gold 50 g column and eluted with 0-60% ACN in water gradient (both with 0.05% formic acid, 50 mL/min). The fractions expected to contain product were combined and freeze-dried to yield compound 18 as white powder (226 g, 0.961 mmol, 81%). ESI-LCMS (M+H): 236.0.

Example 8

Seco-CPI Compound Ia-01

This example and FIG. 2 relate to the preparation of seco-CPI compound Ia-01.

A solution of compounds 16 (5 mg, 0.015 mmol) and 18 (7.0 mg, 0.030 mmol) in anhydrous DMF (Acros, 1 mL) was prepared. N-(3-Dimethylaminopropyl)-N'-ethylcarbodiimide hydrochloride ("EDC," Aldrich, 5.71 mg, 0.030 mmol) was added. The reaction mixture was stirred at RT for 2 h. LCMS analysis showed the reaction to be complete. The reaction mixture was purified by preparative HPLC, eluting with 45-60% ACN in water (with 0.1% TFA, 20 mL/min) on a KINETEX™ 5 μm EVO C18 150×21.2 mm column. The fractions expected to contain product were combined and freeze-dried to yield Ia-01 as an off-white solid (4.1 mg, 7.4 μmol, 50% yield). ESI-LCMS (M+H): 553.1. $^1$H NMR (DMSO-d$_6$, 400 MHz) 11.54 (1H, s), 11.29 (1H, s), 9.75 (1H, s), 7.75 (1H, s), 7.39 (1H, d), 7.15 (1H, d), 7.02 (1H, d), 6.91 (2H, d), 4.74 (1H, t), 4.45 (1H, d), 4.14 (4H, m), 3.89 (2H, m), 3.40-3.80 (12H, m).

Generally following the procedures of this example and FIG. 2, but using alternative precursor materials, additional seco-CPI compounds were prepared as listed in Table V below.

TABLE V

Seco-CPI Compounds Made Following FIG. 2

| Compound No. | Mass spectrum | Remarks |
|---|---|---|
| Ia-02 | $[M - H]^- = 521.2$ | Ethanol was used instead of compound 17b. |
| Ia-08 | $[M + H]^+ = 541.1$ | Ethane-1,2-diol was used instead of compound 17b. |
| Ia-09 | $[M + H]^+ = 567.1$ | 3-Methoxy-1-propanol was used instead of compound 17b. |
| Ia-10 | $[M + H]^+ = 591.1$ | Cyclohexylmethanol was used instead of compound 17b. |
| Ia-16 | $[M + H]^+ = 566.1$ | 2-(Dimethylamino)ethanol was used instead of compound 17b. |
| Ia-30 | $[M + H]^+ = 569$ | 5,6,7-Trimethoxy-1H-indole-2-carboxylic acid (CAS Reg. No. 128781-0707) was used instead of compound 18. |
| Ia-31 | $[M + H]^+ = 565.0$ | 3-Methybutan-1-ol was used instead of compound 17b. |

Example 9

Compound 26

This example and FIG. 3A relate to the synthesis of compound 26.

A solution of compound 19a (Bachem, 7.5 g, 24.09 mmol) and (4-aminophenyl)-methanol 19b (Aldrich, 3.86 g, 31.3 mmol) in anhydrous DCM (Acros, 50 mL) and anhydrous methanol (Acros, 50 mL) was prepared. 2-Ethoxy-1-ethoxycarbonyl-1,2-dihydroquinoline ("EEDQ," Bachem, 8.94 g, 36.1 mmol) was added. The reaction mixture was stirred at RT overnight. LCMS analysis showed the reaction was almost complete. The reaction mixture was diluted with EtOAc (400 mL) and the resultant solution was washed with water and brine. The organic phases were dried over anhydrous $Na_2SO_4$ and concentrated under vacuum to 100 mL volume. The precipitated white solid was collected by filtration and air dried over a weekend to yield compound 20 (white solid, 8.9 g, 21.37 mmol, 89%). ESI-LCMS (M+H): 417.1.

Piperidine (Aldrich, 1 mL) was added to a solution of compound 20 (2.2 g, 5.28 mmol) in DMF (Acros, anhydrous, 10 mL). The reaction mixture was stirred at RT for 1 h. LCMS analysis showed the reaction to be complete. The reaction mixture was freeze-dried with ACN and water to yield crude compound 21 with some Fmoc residue as white solid (2.12 g). ESI-LCMS (M+H): 195.0.

A solution of compound 21 (2.12 g, crude) and compound 22a (Aldrich, 1.610 g, 5.28 mmol) in DMF (Acros, anhydrous, 10 mL) was prepared. DIPEA (Aldrich) was added to adjust the pH of reaction mixture to above 8. The reaction mixture was stirred at RT for 2 h. LCMS analysis showed the reaction to be complete. The reaction mixture was worked up with EtOAc, water and brine. The organic phases were combined and concentrated to leave a residue. The residue was re-dissolved with ACN (Aldrich, 5 mL) and distilled water (10 mL). The suspension was filtered. The filtrate was loaded onto a 130 g COMBIFLASH™ AQ Gold column and eluted at 75 mL/min with 25-40% ACN (with 0.05% formic acid) and water (also with 0.05% formic acid). The fractions expected to contain product were combined and freeze-dried to yield compound 22 as a white solid (0.89 g, 2.262 mmol, 42.8%). ESI-LCMS (M+H): 394.1.

A solution of compound 22 (147 mg, 0.374 mmol) and perbromomethane (Aldrich, 217 mg, 0.653 mmol) in anhydrous DCM (Acros, 4 mL) was prepared. TPP (Aldrich, 171 mg, 0.653 mmol) was added. The reaction mixture was stirred at RT for 5 min, after which a clear solution had formed. LCMS analysis showed the reaction to be complete. The reaction mixture was loaded onto a 12 g COMBIFLASH™ Gold column and eluted with 50-100% EtOAc in hexane (25 mL/min). The fractions expected to contain product were combined, concentrated and dried under high vacuum for 15 min to yield compound 23 as a solid (92 mg, 54%). ESI-LCMS (M+H): 456.1.

Methyl lithium in diethyl ether (Aldrich, 1.6 M, 0.233 mL, 0.373 mmol) was added to a solution of compound 15 (FIG. 2, 100 mg, 0.187 mmol) in anhydrous THF (Acros, 1 mL). The reaction mixture was stirred at RT for 5 min. Compound 23 (92 mg, 0.202 mmol) was added. The reaction mixture was stirred at RT for 10 min. LCMS showed the reaction to be complete. The reaction mixture was worked up with EtOAc, water and brine. The organic phasess were dried over anhydrous $Na_2SO_4$, concentrated and dried under high vacuum to yield compound 24 (153 mg, crude). ESI-LCMS (M+H): 911.2.

TFA (Aldrich, 2 mL) was added to a solution of crude compound 24 (153 mg) in anhydrous DCM (Acros, 0.5 mL). The reaction mixture was stirred at RT for 30 min. LCMS analysis showed the reaction to be complete. The reaction mixture was concentrated and purified on a COMBIFLASH™ AQ Gold 30 g column, eluting with 15-30% ACN (with 0.05% formic acid) in deionized water (with 0.05% formic acid) at 35 mL/min. The fractions expected to contain product were combined and freeze-dried to yield compound 25 as a white solid (61 mg, 53.5%). ESI-LCMS (M+H): 611.2.

A solution of compound 25 (61 mg, 0.100 mmol) and BOC-anhydride (Oakwood, 0.030 mL, 0.130 mmol) in anhydrous DMF (Acros, 1 mL) was prepared. DIPEA (Aldrich, 0.060 mL, 0.348 mmol) was added. The reaction mixture was stirred at RT for 30 min. LCMS analysis showed the reaction to be complete. The reaction mixture was purified by preparative HPLC with 30-50% ACN in water (with 0.1% TFA, 20 mL/min) on a KINETEX™ C18 EVO 5µ 150×22.1 mm column. The fractions expected to contain product were combined and freeze-dried to yield compound 26 as a white solid (60 mg, 84.4%). ESI-LCMS (M+H): 711.2.

Example 10

Seco-CPI-Linker Compound IIIa-03

This example and FIG. 3B relate to the preparation of compound IIIa-03.

DIPEA (Aldrich, 0.074 mL, 0.422 mmol) was added to a solution of compound 18 (FIG. 2, 29.8 mg, 0.127 mmol) and HATU (Oakwood, 48.1 mg, 0.127 mmol) in anhydrous DMF (Acros, 0.7 mL). The reaction mixture was stirred at RT for 5 min. Compound 26 (FIG. 3B, 30 mg, 0.042 mmol) was added. The reaction mixture was stirred at RT overnight. LCMS analysis showed the reaction was 70% complete. The reaction was purified by preparative HPLC, eluting with 50-65% ACN in water (with 0.1% TFA, 20 mL/min) on a KINETEX™ C18 EVO 5µ 150×22.1 mm column. The fractions expected to contain product were combined and freeze-dried to yield compound 27 as a powder (27 mg, 68.8%). ESI-LCMS (M+H): 928.3.

TFA (Sigma, 1 mL) was added to a solution of compound 27 (27 mg, 0.029 mmol) in anhydrous DCM(Acros, 1 mL). The reaction mixture was stirred at RT for 15 min. LCMS analysis showed the reaction to be complete. The reaction was purified by preparative HPLC, eluting with 40-50% ACN in water (with 0.1% TFA, 20 mL/min) on a KINETEX™ C18 EVO 5μ 150×22.1 mm column. The fractions expected to contain product were combined and freeze-dried to yield compound 28 as a powder (20 mg, 83.0%). ESI-LCMS (M+H): 828.2.

DIPEA (Sigma, 20 μL, 0.114 mmol) was added to a solution of compound 28 (20 mg, 0.024 mmol) and 6-maleimidohexanoic acid N-hydroxysuccinimide ester 29 (available from SIGMA-Aldrich, 11.17 mg, 0.036 mmol) in anhydrous DMF (Acros, 0.7 mL). The reaction mixture was stirred at RT for 30 min. LCMS analysis showed the reaction to be complete. The reaction mixture was purified by preparative HPLC, eluting with 50-65% acetonitrile in water (with 0.1% TFA, 20 mL/min) on a KINETEX™ C18 EVO 5μ 150×22.1 mm column. The fractions expected to contain product were combined and freeze-dried to yield seco-CPI-linker compound IIIa-03 as a powder (12.8 mg, 51.9%). ESI-LCMS (M+H): 1021.5. $^1$H NMR (DMSO-d6): δ 11.98 (s, 1H), 11.77 (s, 1H), 9.79 (s, 1H), 8.11 (d, 1H, J=6.9 Hz), 7.79 (d, 1H, J=8.6 Hz), 7.42 (d, 1H, J 8.8 Hz), 7.29 (d, 3H, J=8.3 Hz), 7.19 (s, 1H), 6.98-7.03 (m, 4H), 6.61 (d, 1H, J=7.19 Hz), 6.53 (d, 2H, J=8.5 Hz), 5.05 (t, 2H, J=4.7 Hz), 4.45 (d, 1H, J=10.7 Hz), 4.34 (d, 1H, J=7.1 Hz), 4.11-4.17 (m, 3H), 3.52-3.72 (m, 10H), 3.09-3.38 (m, 9H), 2.15 (m, 2H), 1.95 (m, 1H), 1.48 (m, 4H), 1.27 (m, 3H), 1.17 (m, 2H), 0.84 (m, 6H).

Additional seco-CPI-linker compounds as listed in Table VI below were prepared generally following the procedures of this example and the scheme of FIGS. 3A-3B, but using alternative precursor materials.

Preparation of Compound 66

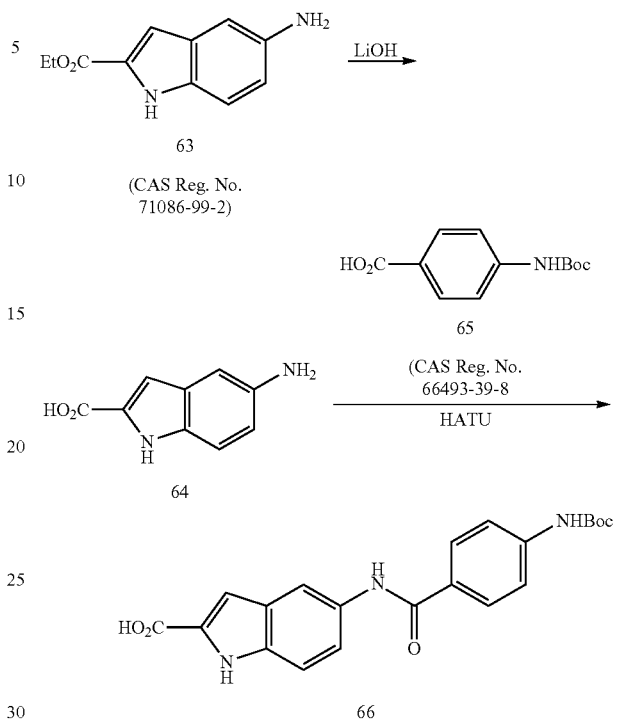

TABLE VI

Seco-CPI-Linker Compounds Made Following FIGS. 3A-3B

| Compound No. | Mass spectrum | Remarks |
|---|---|---|
| IIIa-01 | [M + H]⁺ = 1034.4 | 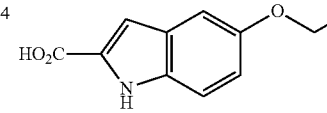 made analogously to compound 18 in FIG. 2, was used instead. |
| IIIa-02 | [M + H]⁺ = 1081.4 | Compound 66, with later removal of Boc protecting group, was used instead of compound 18. Scheme for synthesis of compound 66 is shown below. |
| IIIa-04 | [M + H]⁺ = 991.4 | 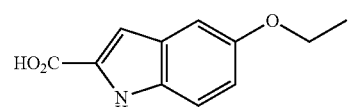 made analogously to compound 18 in FIG. 2, was used instead. |
| IIIa-13 | [M + H]⁺ = 1059.4 | 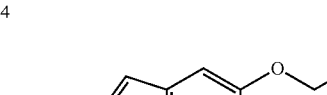 made analogously to compound 18 in FIG. 2, was used instead. |

Example 11

Seco-CPI Compound Ia-21

Figure 4:
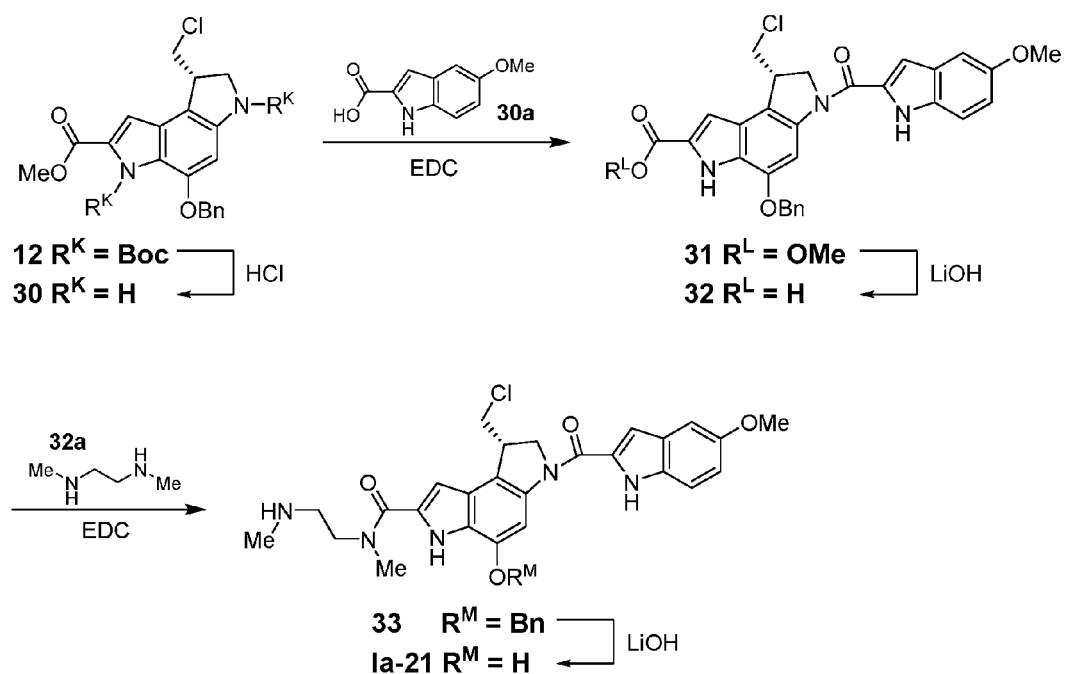

This example and FIG. 4 relate to the preparation of seco-CPI compound Ia-21.

HCl in dioxane (4 N, 15 mL) was added to ester 12 (0.25 g, 0.4388 mmol). The reaction mixture was stirred at 50° C. for 5 h. LCMS analysis showed the reaction to be complete. The reaction mixture was blow dried under nitrogen to yield a dark blue residue as crude acid 30, used in next step without further purification. ESI-LCMS (M+H): 371.1.

N,N-Dimethylacetamide ("DMA," 5 mL) was added to crude acid 30 (hydrochloride salt, 178 mg, 0.437 mmol), 5-methoxy-1H-indole-2-carboxylic acid 30a (CAS Reg. No. 4382-54-1, available from Sigma-Aldrich, 125 mg, 0.656 mmol), EDC (251 mg, 1.311 mmol), 1-hydroxybenzotriazole ("HOBT," 201 mg, 1.311 mmol), and NaHCO$_3$ (184 mg, 2.185 mmol). The black solution was stirred at RT for 4.5 h. LCMS analysis showed appearance of the product peak. The reaction mixture was diluted with water (15 mL), stirred at RT for 15 min and filtered. The crude product was collected as a brown solid and re-dissolved in DCM/methanol. The resultant solution was concentrated to dryness with silica gel (1.3 g) to form a slurry. The slurry was purified on a 15 g silica gel column with 0-3% ethyl acetate in DCM eluent gradient. The fractions containing expected product were combined, concentrated and dried under vacuum to yield crude product (206 mg). The crude product was re-dissolved in 20% methanol in chloroform and concentrated with 1.3 g silica gel to a slurry. The slurry was purified on silica gel column with 100% DCM and 1-5% ethyl acetate in hexane eluent. The fractions containing expected product were combined, concentrated and dried under high vacuum to yield slightly impure compound 31(0.108 g, 0.199 mmol, 45.4%). ESI-LCMS (M+H): 544.4.

THF (3 mL), water (1.000 mL), and MeOH (2.000 mL) were added to compound 31 (104 mg, 0.191 mmol) and lithium hydroxide hydrate (138 mg, 3.29 mmol) was added). The yellow heterogeneous mixture stirred overnight. LC/MS showed the reaction to be complete. The reaction mixture was acidified with 1 N HCl and then filtered. The solid was collected and dried to yield crude compound 32 (0.168 g, 88%). ESI-LCMS (M+H): 529.9.

DMA (0.5 mL) was added to compound 32 (15 mg, 0.028 mmol), N,N'-dimethyl-ethane-1,2-diamine 32a (CAS Reg. No. 110-70-3, available from Sigma-Aldrich, 1.247 mg, 0.014 mmol), EDC (10.85 mg, 0.057 mmol), HOBT (8.67 mg, 0.057 mmol), and NaHCO$_3$ (9.51 mg, 0.113 mmol). LC/MS shows reaction to be 50% complete. The reaction mixture was diluted with MeOH and purified by preparative LC with 15-100% ACN in water (both with 0.1% TFA, 40 mL/min) gradient. The fractions containing expected product were combined and freeze-dried to yield compound 33 (5.8 mg, 7.98 μmol, 28.2%). ESI-LCMS (M+H): 600.10.

MeOH (0.5 mL) was added to compound 33 (TFA salt, 5.7 mg, 7.98 μmol), ammonium formate (15.10 mg, 0.239 mmol), and Pd—C(1.699 mg, 1.596 μmol). The reaction mixture was heated to reflux for 30 sec. After 10 min, LC/MS showed the reaction to be complete. The reaction mixture was filtered and the filtrate was purified by preparative HPLC with 0-75% ACN in water (both with 0.1% TFA, 25 ml/min) on Waters-YMC-OBD S5 20×100 mm column. The fractions containing expected product were combined and freeze-dried to yield seco-CPI compound Ia-21 as an amber solid (1.5 mg, 2.12 μmol, 26.5%). ESI-LCMS (M+H): 510.15. $^1$H NMR (MeOD, 500 MHz) 7.92 (1H, s), 7.41 (1H, d, J=5 Hz), 7.18 (1H, d, J=1 Hz), 7.14 (1H, s), 7.07 (1H, s), 6.96 (1H, dd, J=10 Hz), 4.76 (1H, t), 4.61 (1H, dd), 4.09 (2H, m), 3.86 (3H, s), 3.80 (3H, m), 3.40 (2H, t, J=5 Hz), 3.03 (6H, s).

Generally following the procedures of this example and FIG. 4, but using alternative precursor materials, additional seco-CPI compounds were prepared as listed in Table VII below.

TABLE VII

| Seco-CPI Compounds Made Following FIG. 4 | | |
|---|---|---|
| Compound No. | Mass spectrum | Remarks |
| Ia-11 | [M + H]$^+$ = 509.3 | Morpholine was used instead of compound 32a. |
| Ia-19 | [M + H]$^+$ = 494.1 | Morpholine was used instead of compound 32a and 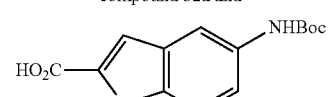 was used instead of compound 30a, with later removal of Boc protecting group. |
| Ia-20 | [M + H]$^+$ = 522.2 | 1-Methylpiperazine was used instead of compound 32a. |
| Ia-22 | [M + H]$^+$ = 527.2 | 2-(2-Aminoethoxy)ethanol was used instead of compound 32a. |
| Ia-23 | [M + H]$^+$ = 511.2 | (S)-2-Aminobutan-1-ol was used instead of compound 32a. |

TABLE VII-continued

Seco-CPI Compounds Made Following FIG. 4

| Compound No. | Mass spectrum | Remarks |
|---|---|---|
| Ia-24 | [M + H]$^+$ = 584.4 | 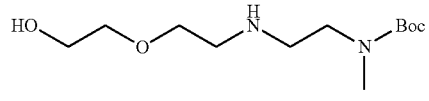 was used instead of compound 32a, with later removal of Boc protecting group. |

Example 12

Seco-CPI-Linker Compound IIIa-05

Figure 5:
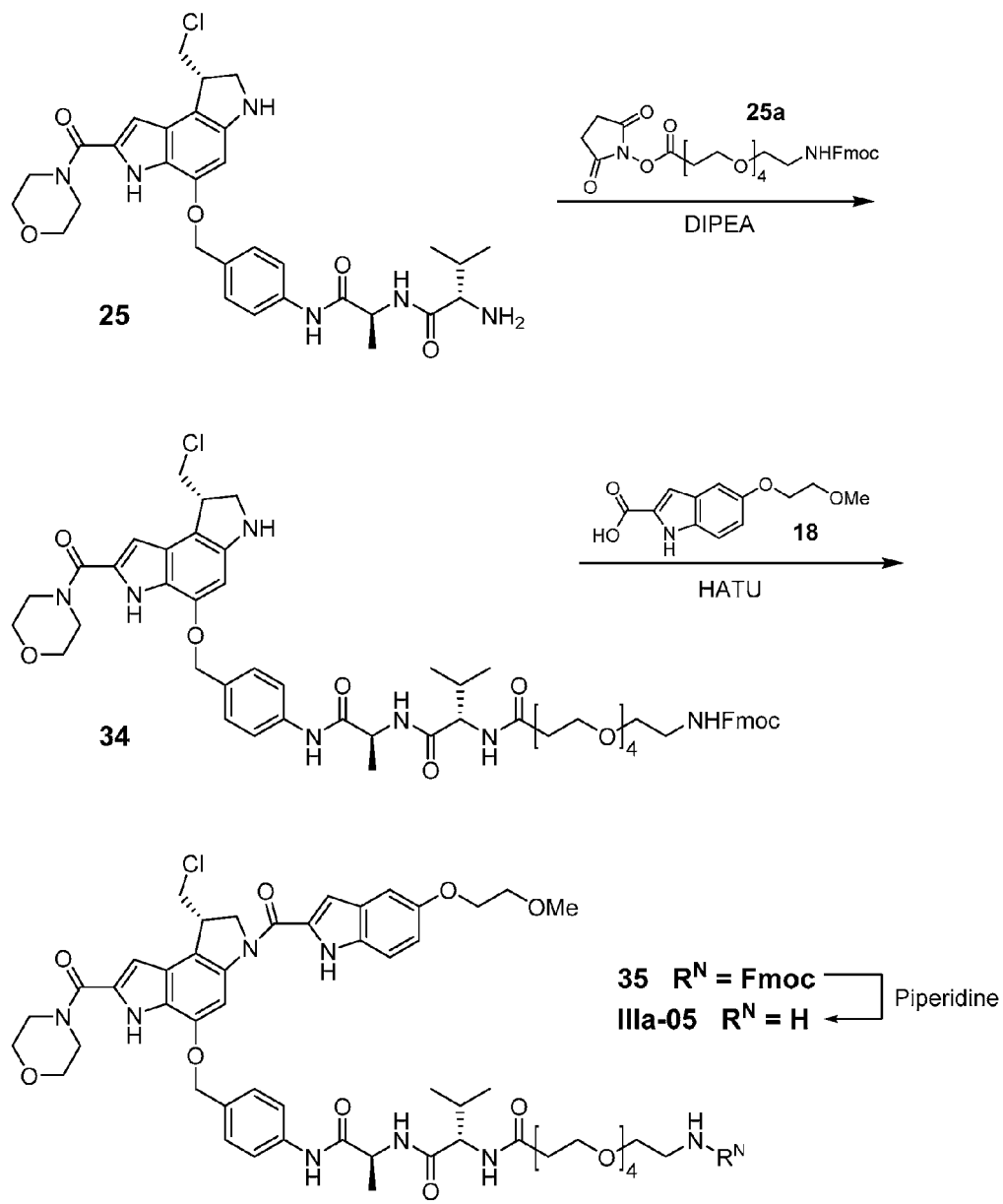

This example and FIG. 5 relate to the preparation of seco-CPI-linker compound IIIa-05.

DIPEA (Sigma, 0.052 mL, 0.299 mmol) was added to a solution of compound 25 (61 mg, 0.100 mmol) and hydroxysuccinimide ester 25a (QuiantaBiodesign, 76 mg, 0.130 mmol) in DMF (Acros, anhydrous, 1 mL). The reaction mixture was stirred at RT for 60 min. LCMS analysis showed the reaction to be complete. The reaction mixture was neutralized with acetic acid (40 uL), loaded onto 30 g COMBIFLASH™ AQ Gold column and purified with 50-75% ACN in water (both with 0.05% formic acid, 35 mL/min). The fractions containing the expected product were combined and freeze-dried to yield compound 34 (52 mg, 0.048 mmol, 48.2% yield). ESI-LCMS (M+H): 1080.3.

DIPEA (Sigma, 0.042 mL, 0.241 mmol) was added to a solution of acid 18 (34.0 mg, 0.144 mmol), compound 34 (52 mg, 0.048 mmol) and HATU (Oakwood, 54.9 mg, 0.144 mmol) in DMF (Acros, anhydrous, 0.7 mL). The reaction mixture was stirred at RT overnight. LCMS analysis showed the reaction to be 70% complete. The reaction mixture was purified by preparative HPLC with 45-65% ACN in water (with 0.1% TFA, 20 mL/min) on a KINETEX™ 5μ C18 EVO 150×21.2 mm column. The fractions containing product were combined and freeze-dried to yield compound 35 (31 mg, 49.8%). ESI-LCMS (M+H): 1297.3.

Piperidine (Aldrich, 50 μL) was added to a solution of compound 35 (31 mg) in DMF (Acros, anhydrous, 0.5 mL). The reaction mixture was stirred at RT for 30 min. LCMS analysis showed the reaction to be complete. The reaction mixture was neutralized with AcOH (50 μL) and purified by preparative HPLC with 30-40% ACN in water gradient (with 0.1% TFA, 20 mL/min) on a KINETEX™ C18 5μ 150×21.2 mm column. The fractions containing the expected product were combined and freeze-dried to yield seco-CPI-linker compound IIIa-05 (22 mg. 64.2%), as a TFA salt. ESI-LCMS (M+H): 1075.6. $^1$H NMR (DMSO-d6): δ 11.97 (s, 1H), 11.77 (s, 1H), 9.81 (s, 1H), 8.15 (d, 1H, J=3.1 Hz), 7.88 (d, 1H, J=8.8 Hz), 7.79 (s, 3H), 7.42 (d, 1H, J 9.1 Hz), 7.30 (d, 3H, J=8.6 Hz), 7.19 (s, 1H), 6.96-7.02 (m, 2H), 6.63 (d, 1H, J=1.9 Hz), 6.53 (d, 2H, J=8.6 Hz), 5.06 (t, 2H, J=4.9 Hz), 4.45 (d, 1H, J=10.7 Hz), 4.34 (d, 1H, J=7.1 Hz), 4.21 (m, 1H), 4.12 (s, 2H), 2.96-3.72 (m, 32H), 2.36-2.48 (m, 4H), 1.97 (m, 2H), 1.28 (d, 3H, J=7.1 Hz), 0.85 (m, 6H).

Additional seco-CPI-linker compounds, as listed in Table VIII below, were prepared generally following following the procedures of this example and the scheme of FIG. 5, but using alternative precursor materials.

TABLE VIII

Seco-CPI-Linker Compounds Made Following FIG. 5

| Compound No. | Mass spectrum | Remarks |
|---|---|---|
| IIIa-06 | [M + H]$^+$ = 1088.4 | 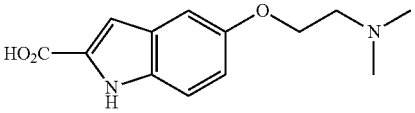 made analogously to compound 18 in FIG. 2, was used instead. |
| IIIa-07 | [M + H]$^+$ = 1087.3 | 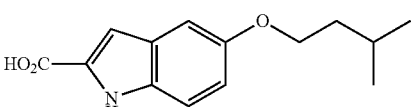 made analogously to compound 18 in FIG. 2, was used instead. |

TABLE VIII-continued

Seco-CPI-Linker Compounds Made Following FIG. 5

| Compound No. | Mass spectrum | Remarks |
| --- | --- | --- |
| IIIa-08 | [M + H]$^+$ = 1113.4 | 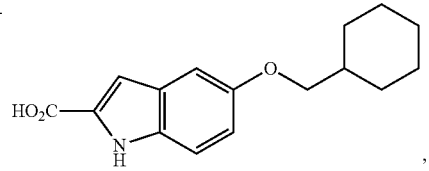 made analogously to compound 18 in FIG. 2, was used instead. |
| IIIa-09 | [M + H]$^+$ = 1091.3 | 5,6,7-Trimethoxy-1H-indole-2-carboxylic acid (CAS Reg. No. 128781-0707) was used instead of compound 18. |
| IIIa-10 | [M + H]$^+$ = 1134.5 | Compound 48a (FIG. 9) was used instead of compound 18, followed by removal of the Boc protecting group and HATU mediated coupling with 4-hydroxybenzoic acid. |
| IIIa-11 | [M + H[$^+$ = 1059.5 | 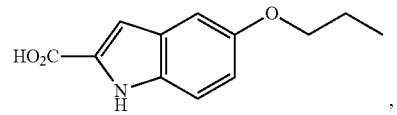 made analogously to compound 18 in FIG. 2, was used instead. |
| IIIa-12 | [M + H]$^+$ = 1045.4 | 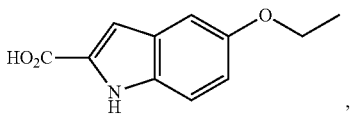 made analogously to compound 18 in FIG. 2, was used instead. |

Example 13

Seco-CPI Compound Ia-15

Figure 6:
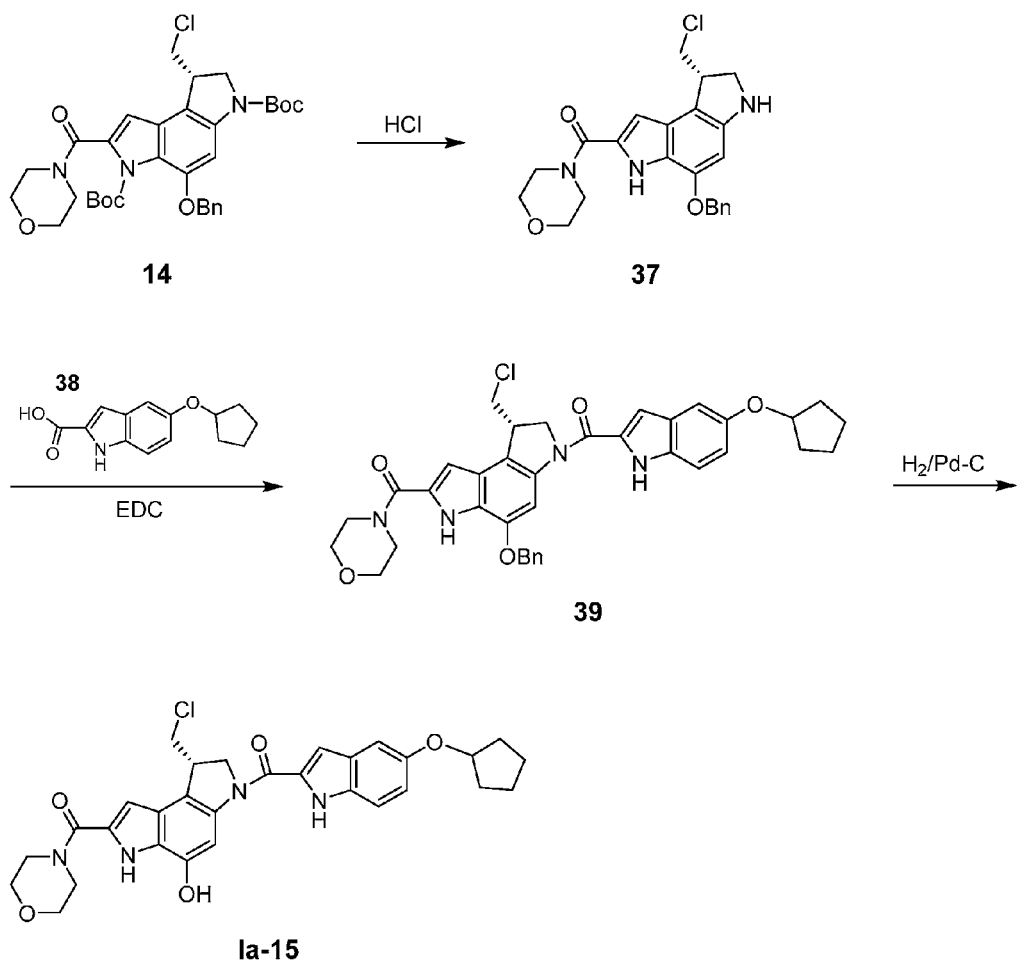

FIG. 6 shows the scheme for the synthesis of seco-CPI compound Ia-15. The reagents used, and the conditions for their use, are known in the art and/or have been exemplified in the preceding examples. Table IX shows analytical data for compound Ia-15 and other compounds similarly prepared.

TABLE IX

Seco-CPI Compounds Made Following FIG. 6

| Compound No. | Mass spectrum | Remarks |
| --- | --- | --- |
| Ia-03 | [M + H]$^+$ = 537.3 | 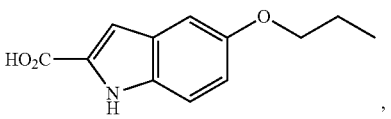 made analogously to compound 18 in FIG. 2, was used instead of compound 38. |

TABLE IX-continued

Seco-CPI Compounds Made Following FIG. 6

| Compound No. | Mass spectrum | Remarks |
|---|---|---|
| Ia-04 | [M + H]⁺ = 549.1 | 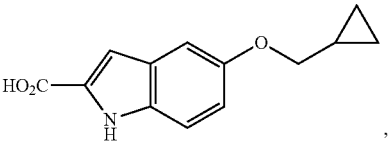 made analogously to compound 18 in FIG. 2, was used instead of compound 38. |
| Ia-05 | [M + H]⁺ = 551.3 | 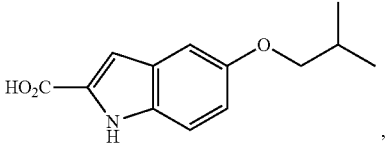 made analogously to compound 18 in FIG. 2, was used instead of compound 38. |
| Ia-06 | [M + H]⁺ = 549.2 | 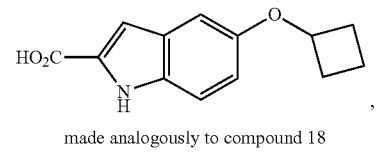 made analogously to compound 18 in FIG. 2, was used instead of compound 38. |
| Ia-07 | [M + H]⁺ = 563.5 | 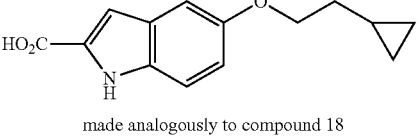 made analogously to compound 18 in FIG. 2, was used instead of compound 38. |
| Ia-12 | [M + H]⁺ = 555.3 | 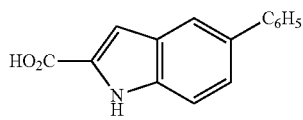 (CAS Reg. No. 66616-71-5) was used instead of compound 38. |
| Ia-13 | [M + H]⁺ = 537.3 | 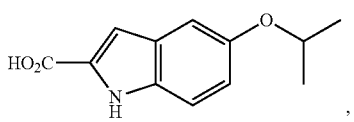 made analogously to compound 18 in FIG. 2, was used instead of compound 38. |
| Ia-14 | [M + H]⁺ = 579.2 | 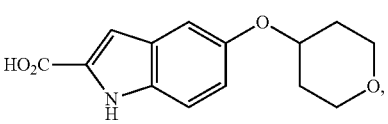 made analogously to compound 18 in FIG. 2, was used instead of compound 38. |

TABLE IX-continued

Seco-CPI Compounds Made Following FIG. 6

| Compound No. | Mass spectrum | Remarks |
|---|---|---|
| Ia-15 | $[M + H]^+ = 563.4$ | As depicted |
| Ia-28 | $[M + H]^+ = 551.1$ | 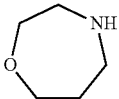 was used instead of morpholine to make counterpart of compound 14 per the procedure of FIG. 2 and 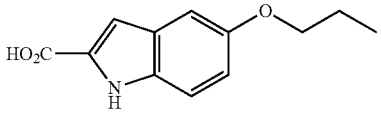 was used instead of compound 38. |

Example 14

Seco-CPI Compound Ia-18

Figure 7:
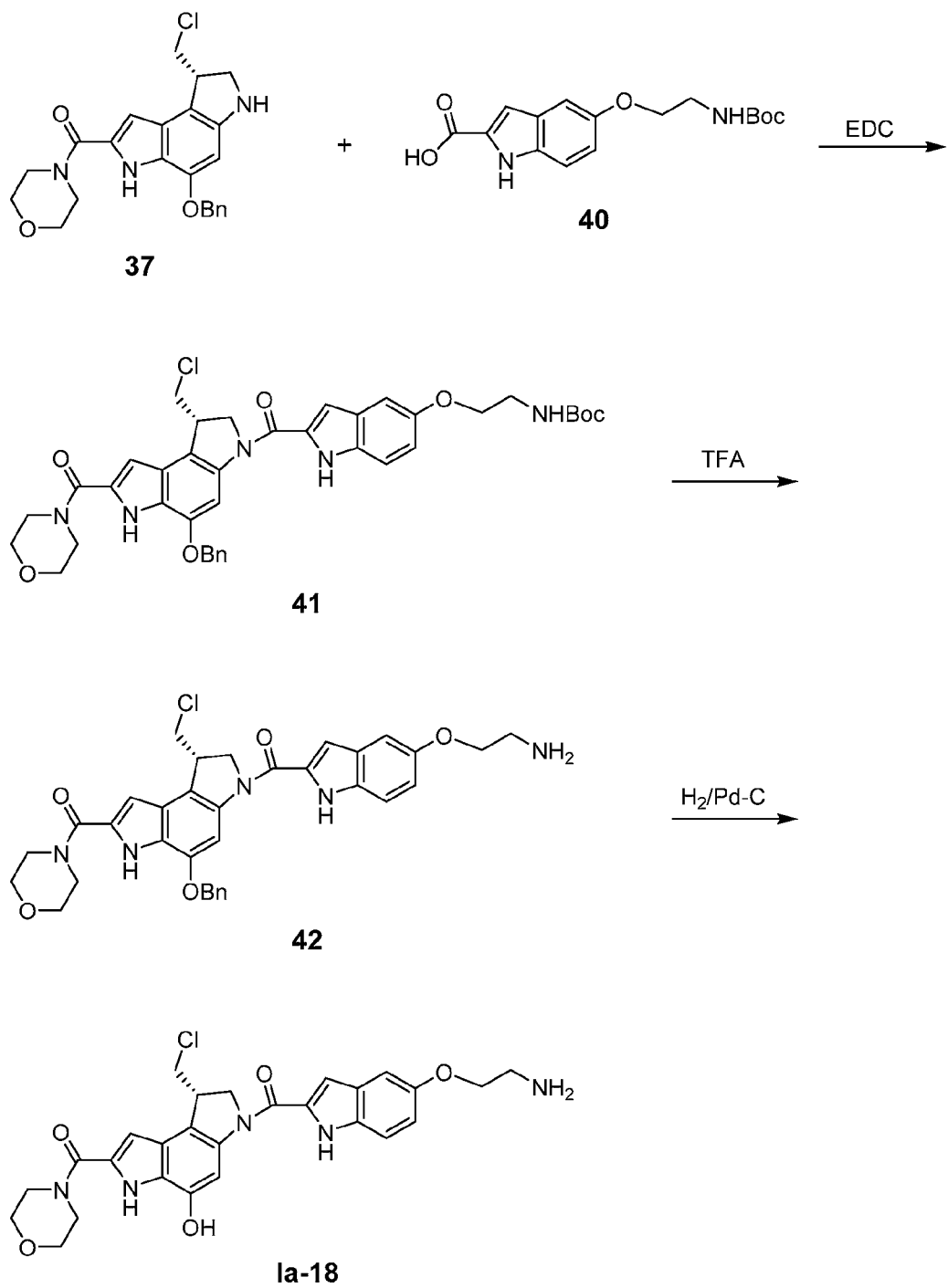

FIG. 7 shows the scheme for the synthesis of seco-CPI compound Ia-18. The reagents used, and the conditions for their use, are known in the art and/or have been exemplified in the preceding examples. Table X shows analytical data for compound Ia-18 and another compound similarly prepared.

TABLE X

Seco-CPI Compounds Made Following FIG. 7

| Compound No. | Mass spectrum | Remarks |
|---|---|---|
| Ia-17 | $[M + H]^+ = 552.2$ | 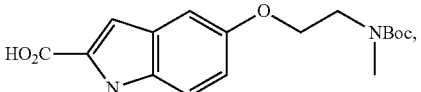 analogously to compound 18 (FIG. 2) using 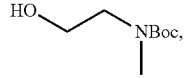 was used instead of compound 40. |
| Ia-18 | $[M + H]^+ = 538.2$ | Compound 40 was made analogously to compound 18 (FIG. 2), using 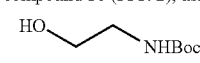 |

Example 15

Seco-CPI Compounds Ib-01 and Ib-02

Figure 8:
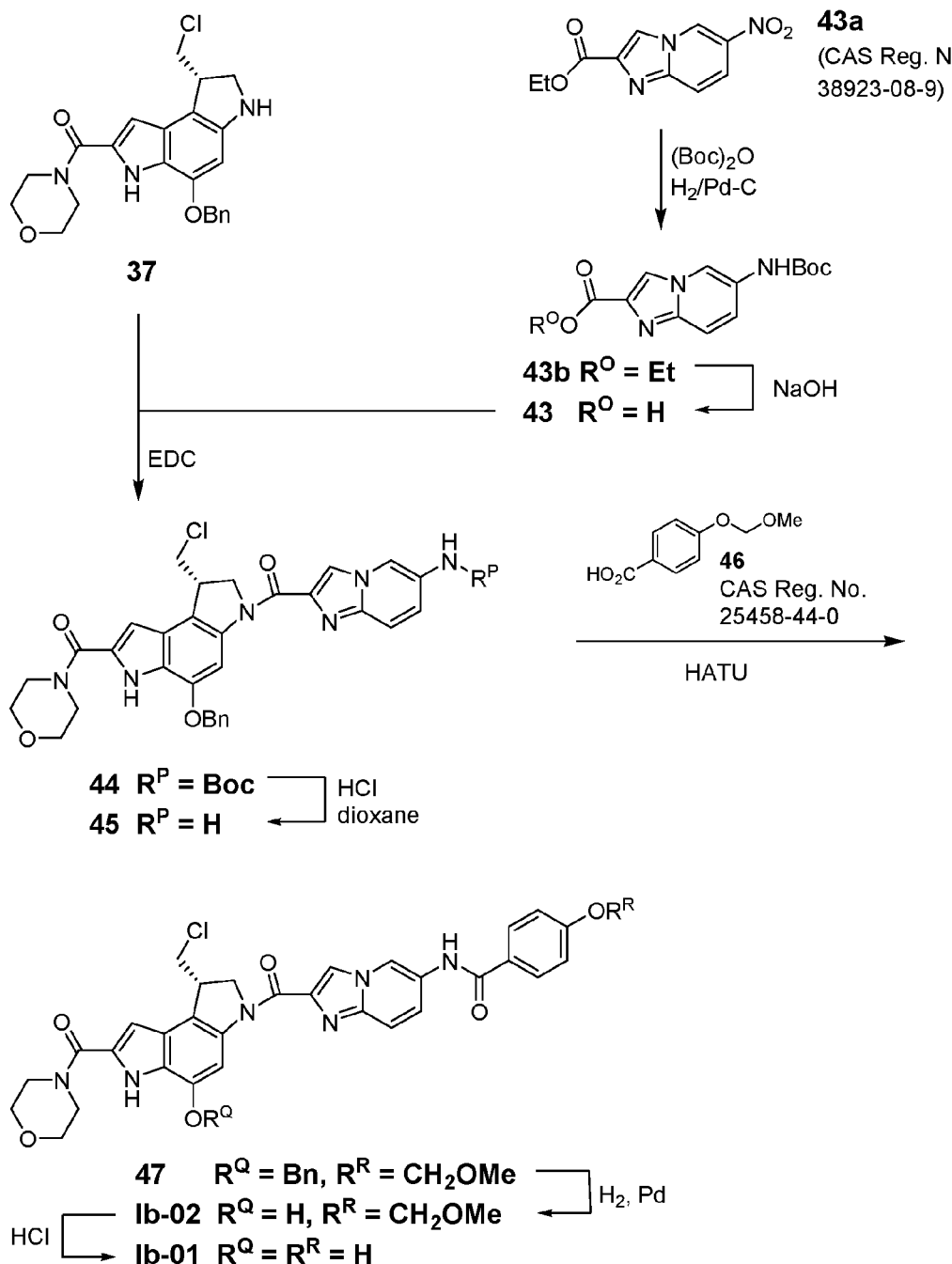

FIG. 8 shows a scheme for the synthesis of seco-CPI compounds Ib-01 and Ib-02. The reagents used, and the conditions for their use, are known in the art and/or have been exemplified in the preceding examples. Ib-01 $[M+H]^+$ =615.0; Ib-02 $[M+H]^+$=659.4.

Example 16

Seco-CPI Compound Id-02

Figure 9:
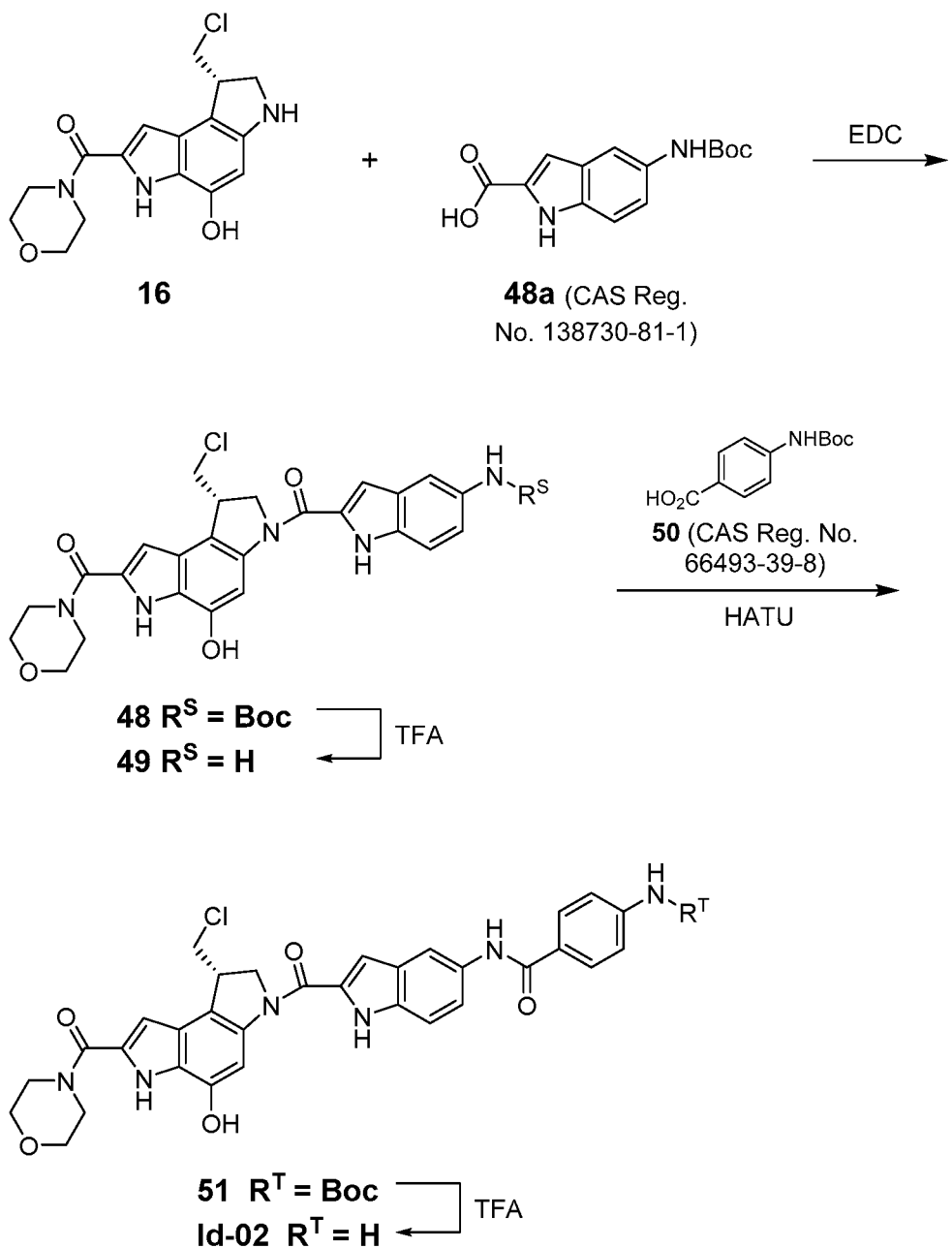

FIG. 9 shows the scheme for the synthesis of seco-CPI compound Id-02. The reagents used, and the conditions for their use, are known in the art and/or have been exemplified in the preceding examples. Table XI shows analytical data for compound Id-02 and other compounds similarly prepared.

TABLE XI

Seco-CPI Compounds Made Following FIG. 9

| Compound No. | Mass spectrum | Remarks |
|---|---|---|
| Ic-01 | $[M + H]^+ = 652.3$ | Compound 48a was used instead of compound 50. |

TABLE XI-continued

Seco-CPI Compounds Made Following FIG. 9

| Compound No. | Mass spectrum | Remarks |
|---|---|---|
| Id-01 | [M + H]$^+$ = 614.1 | 4-Hydroxybenzoic acid was used instead of compound 50. |
| Id-02 | [M + H]$^+$ = 613.1 | As depicted. |

Example 17

Seco-CPI Compound Ia-25

Figure 10:
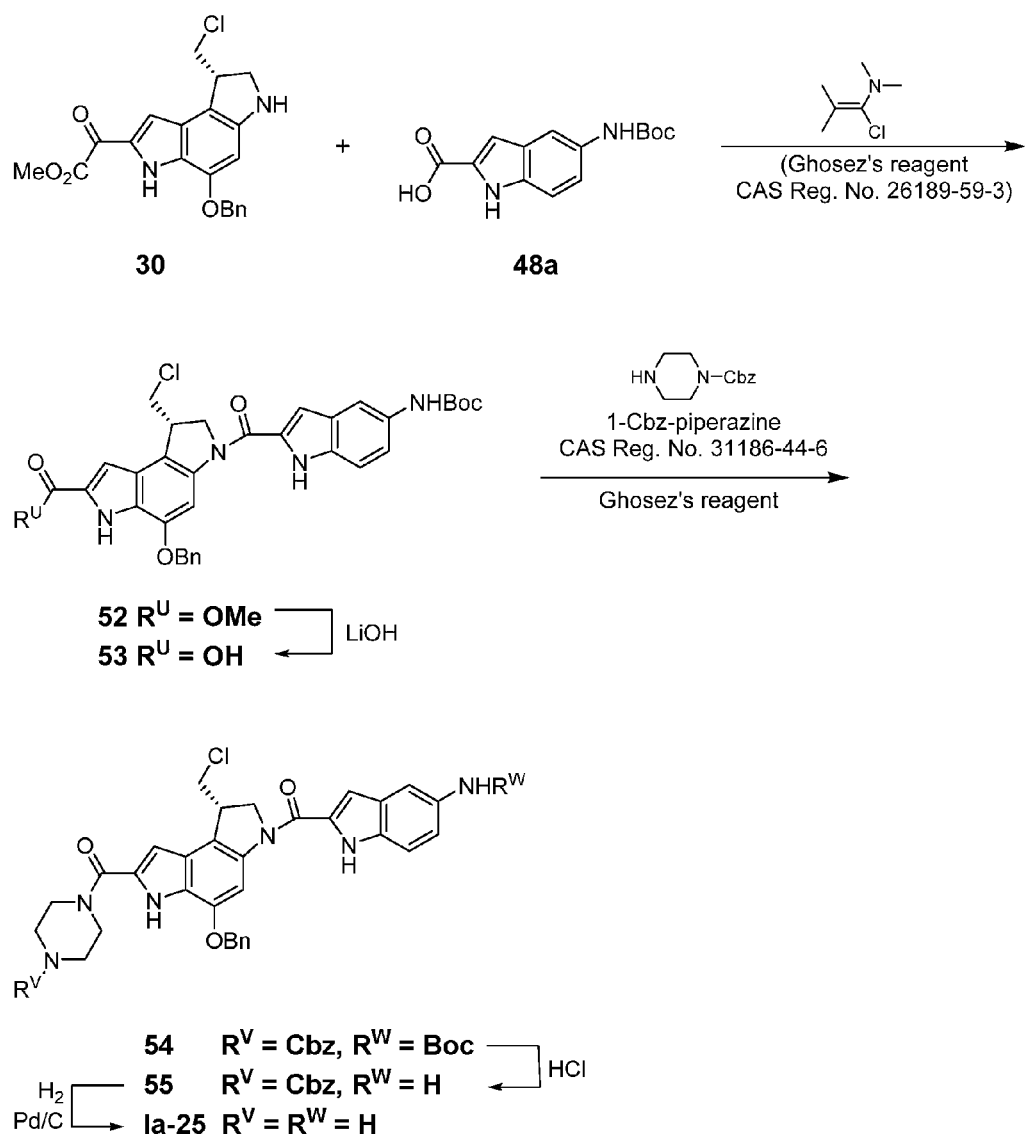

FIG. 10 shows the scheme for the synthesis of seco-CPI compound Ia-25. The reagents used, and the conditions for their use, are known in the art and/or have been exemplified in the preceding examples.

Compound Ia-26 was analogously prepared, using 1-methylpiperazine instead of 1-Cbz-piperazine.

The mass spectral data for the two compounds were: Ia-25 [M+H]$^+$=493.2; Ia-26 [M+H]+=507.3.

Example 18

Seco-CPI Compound Ia-27

Figure 11:
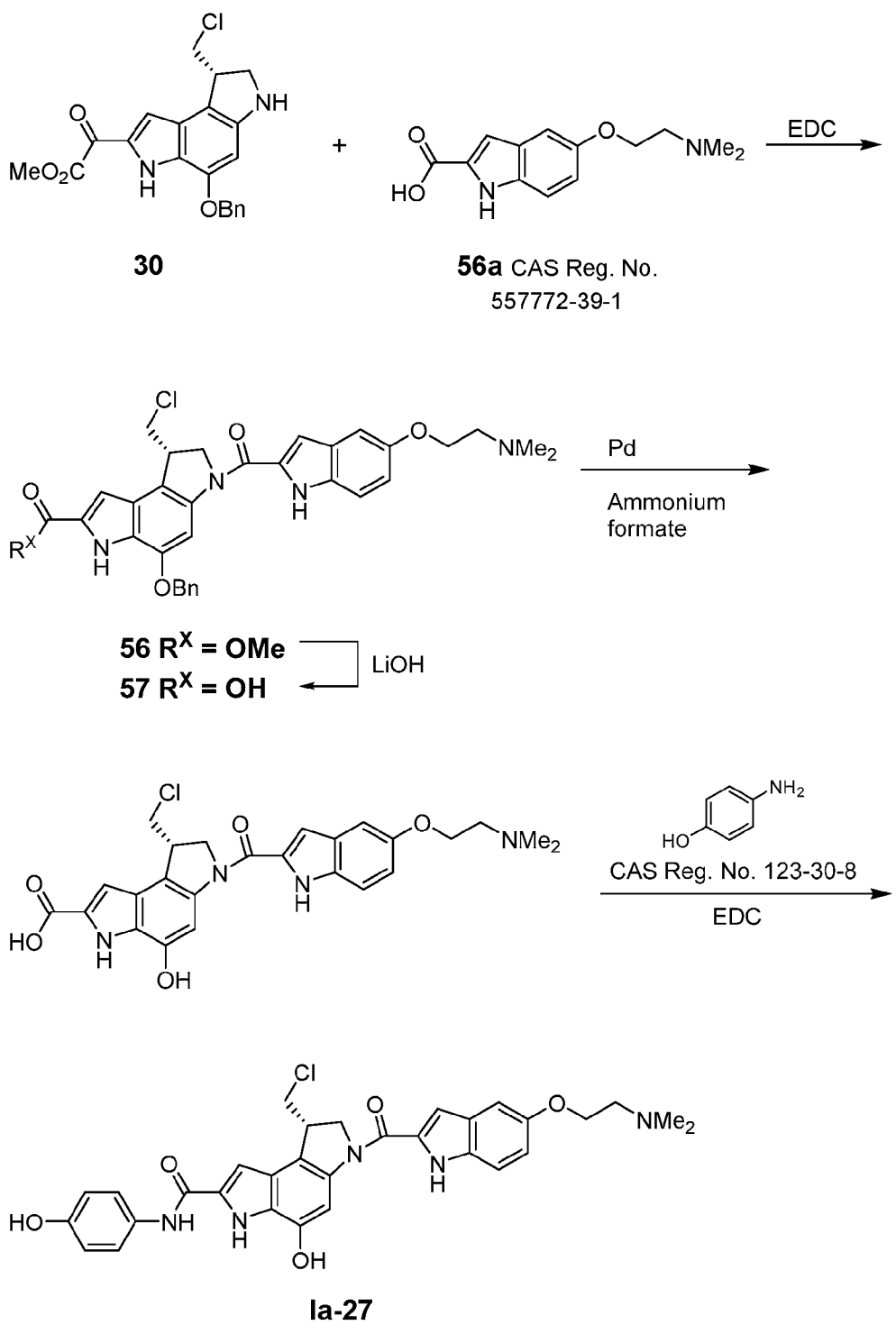

FIG. 11 shows the scheme for the synthesis of seco-CPI compound Ia-27. The reagents used, and the conditions for their use, are known in the art and/or have been exemplified in the preceding examples. Mass spectral data for compound Ia-27: [M+H]$^+$=588.1.

Example 19

Seco-CPI Compound Ia-29

Figure 12:
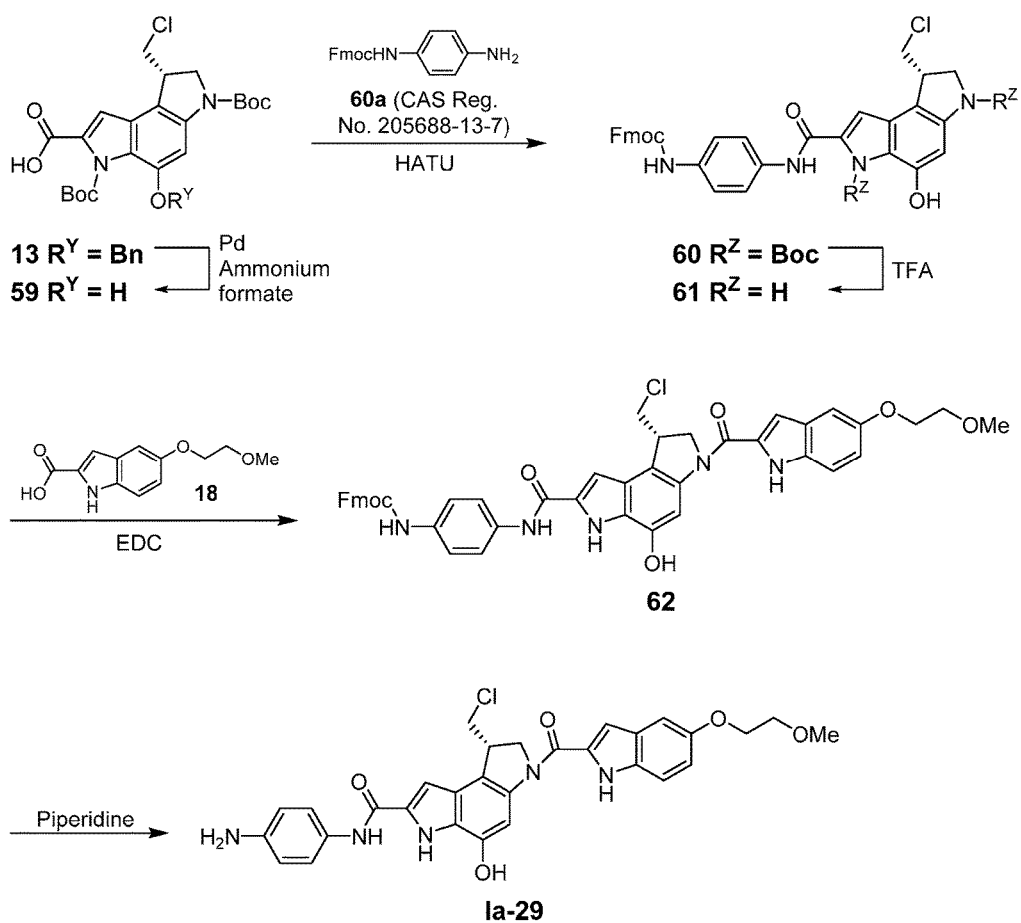

FIG. 12 shows the scheme for the synthesis of seco-CPI compound Ia-29. The reagents used, and the conditions for their use, are known in the art and/or have been exemplified in the preceding examples. Mass spectral data for compound Ia-29: [M+H]$^+$=574.1.

Example 20

Biological Activity of Conjugates

Seco-CPI-linker compounds IIIa-01, IIIa-02, IIIa-03, and IIIa-04 were conjugated to the anti-mesothelin antibody 6A4 (Terrett et al., U.S. Pat. No. 8,268,970 B2 (2012)) generally following the Michael addition procedure of Example 1 above. The resulting antibody-drug conjugates were designated 6A4/IIIa-01 ADC, 6A4/IIIa-02 ADC, 6A4/IIIa-03 ADC, and 6A4/IIIa-04 ADC, respectively.

Additionally, seco-CPI-linker compounds IIIa-06 and IIIa-12 were conjugated to anti-mesothelin antibody 6A4 engineered to have an N297A (EU as in Kabat) substitution in the heavy chain, generally following the transglutaminase mediated conjugation procedure of Example 2. The N297A substitution abrogates glycosylation of the antibody and makes nearby glutamine 295 (Q295) available as an amine acceptor for a transglutamine-catalyzed transamidation reaction (Jeger et al., Angew. Chem. Int. Ed. 2010, 49, 9995). The resulting antibody-drug conjugates were designated 6A4 (N297A)/IIIa-06 ADC and 6A4(N297A)/IIIa-12 ADC, respectively.

The activities of these ADCs against H226 and N87 cancer cells, both of which express mesothelin, was measured using a $^3$H thymidine incorporation assay (Cheng et al., U.S. Pat. No. 8,394,922 B2 (2013)). Results are presented in Table XII.

TABLE XII

Biological Activity of Conjugates

| | EC$_{50}$ (nM) | |
|---|---|---|
| Conjugate | H226 Cells | N87 Cells |
| 6A4/IIIa-01 ADC | 1.2, 0.45 | 256 |
| 6A4/IIIa-02 ADC | 5.8 | — |
| 6A4/IIIa-03 ADC | 0.3 | 3.5 |
| 6A4/IIIa-04 ADC | 0.10 | 0.12 |
| 6A4(N297A)/IIIa-06 ADC | 0.18 | — |
| 6a4(N297A)/IIIa-12 ADC | 0.20 | — |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Boger, U.S. Pat. No. 6,281,354 B1 (2001).
Boger, U.S. Pat. No. 6,548,530 B1 (2003).
Boger and Johnson, Proc. Nat. Acad. Sci. (USA) 1995, 92, 3642.
Boger et al., J. Org. Chem. 1990, 55, 5823.
Boger et al., J. Am. Chem. Soc. 1997, 119, 4987.
Boger et al., Synthesis 1999, SI, 1505.
Boger et al., J. Org. Chem. 2000, 65, 4101.
Boyd et al., US 2008/0279868 A1 (2008).
Chari et al., Cancer Res. 1995, 55, 4079.
Chen et al., U.S. Pat. No. 8,664,407 B2 (2014).
Ducry et al., Bioconjug. Chem. 2010, 21, 5.
Gangwar et al., U.S. Pat. No. 7,968,586 B2 (2011).
Hurley et al., Science 1984, 226, 843.
Kobayashi et al., Cancer Res. 1994, 54, 2404.
Lajiness et al., J. Med. Chem. 2010, 53, 7731.
Li et al., Cancer Res. 1992, 52, 4904.
Nagamura and Saito, Chem. Heterocyclic Compounds 1998, 34 (12), 1386.
Nagamura et al., Chem. Pharm. Bull. 1996, 44 (9), 1723.
Ng et al., U.S. Pat. No. 7,129,261 B2 (2006).

Ng et al., U.S. Pat. No. 7,507,420 B2 (2009).
Ng et al., U.S. Pat. No. 8,034,959 B2 (2011).
Schrama et al., *Nature Rev. Drug Disc.* 2006, 5, 147-159.
Sufi et al., U.S. Pat. No. 8,461,117 B2 (2013).
Tichenor et al., *J. Am. Chem. Soc.* 2007, 129, 10858.
Tietze et al., *ChemBioChem* 2001, 2, 758.
Tietze et al., *Bioorg. Med. Chem.* 2008, 16, 6312.
Zhang et al., U.S. Pat. No. 8,852,599 B2 (2014).
Zhao et al., U.S. Pat. No. 7,655,660 B2 (2010).

What is claimed is:

1. A compound having a structure represented by formula (I)

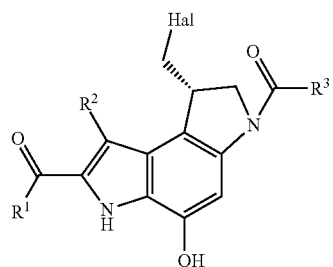

wherein

Hal is Cl or Br;

$R^1$ is

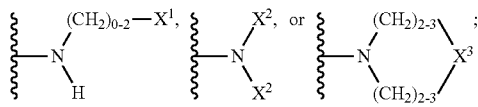

$R^2$ is H, $C_1$-$C_3$ alkyl, $CO_2H$, $CO_2(C_1$-$C_3$ alkyl), $C(=O)NH_2$, $C(=O)NH(C_1$-$C_3$ alkyl), or $C(=O)N(C_1$-$C_3$ alkyl)$_2$;

$R^3$ is

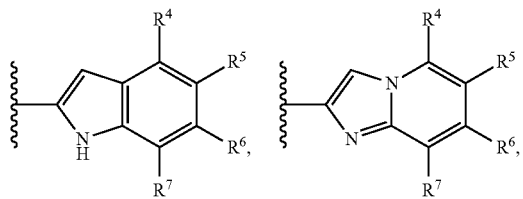

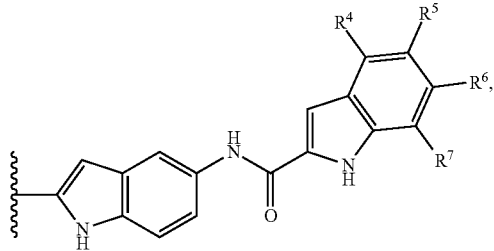

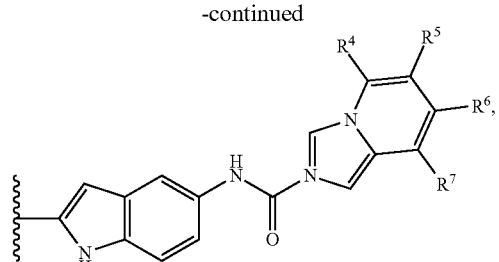

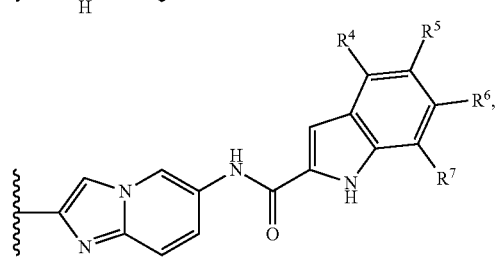

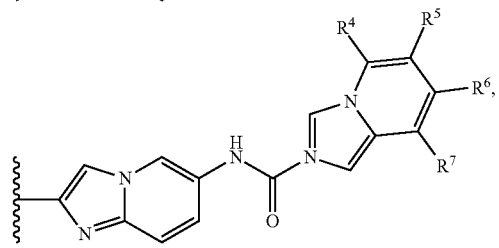

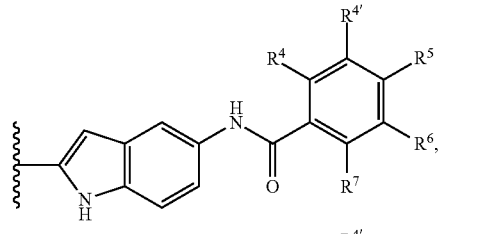

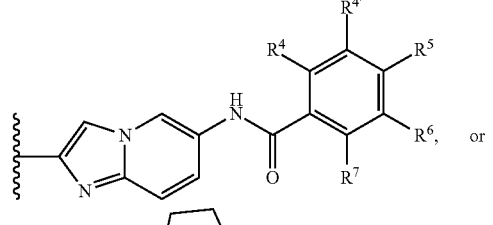

$R^4$, $R^{4'}$, $R^5$, $R^6$, or $R^7$ are independently H, OMe, OH, a 6-membered aryl group, a 5- or 6-membered heteroaryl group, $NH_2$, NHMe, $NMe_2$, $NH(C_2$-$C_4$ alkyl), $N(C_2$-$C_4$ alkyl)$_2$, $NHC(=O)X^1$, $O(C_2$-$C_4$ alkyl), $O(CH_2)_{0-2}(C_3$-$C_6$ cycloalkyl), $O(CH_2)_{0-2}X^1$, or

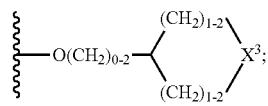

wherein a $C_2$-$C_4$ alkyl group may unsubstituted or substituted with $OCH_2CH_2OH$, $OCH_2CH_2NH_2$, $NHCH_2CH_2OH$, $NHCH_2CH_2NH_2$, OH, or $NH_2$ and an aryl or heteroaryl group may be substituted with $C_1$-$C_2$ alkyl, OH, $NH_2$, NH($C_1$-$C_2$ alkyl), N($C_1$-$C_2$ alkyl)$_2$, F, Cl, Br, $NO_2$, or CN;

with the proviso that at least one of $R^4$, $R^{4'}$, $R^5$, $R^6$, and $R^7$ is other than H;

$R^8$ and $R^{8'}$ are independently H, OH, O($C_1$-$C_3$ alkyl), Cl, Br, F, O(CH$_2$)$_{2-4}$NH$_2$, or O(CH$_2$)$_{2-4}$OH;

$R^9$ is H, C(=O)($C_1$-$C_3$ alkyl), C(=O)NH$_2$, C(=O)NH($C_1$-$C_3$ alkyl), C(=O)($C_1$-$C_3$ alkyl)$_2$, (CH$_2$)$_{2-4}$OH, (CH$_2$)$_{2-4}$O($C_1$-$C_3$ alkyl), (CH$_2$)$_{2-4}$NH$_2$, (CH$_2$)$_{2-4}$NH($C_1$-$C_3$ alkyl), or (CH$_2$)$_{2-4}$N($C_1$-$C_3$ alkyl)2;

each $X^1$ is independently a 6-membered aryl or 5- to 6-membered heteroaryl group that is unsubstituted or substituted with $C_1$-$C_3$ alkyl, OH, O($C_1$-$C_3$ alkyl), NH$_2$, NH($C_1$-$C_3$ alkyl), N($C_1$-$C_3$ alkyl)$_2$, F, Cl, Br, $NO_2$, or CN;

each $X^2$ is independently H, Me, or a $C_2$-$C_4$ alkyl group that may be unsubstituted or substituted with $OCH_2CH_2OH$, $OCH_2CH_2NH_2$, $NHCH_2CH_2OH$, $NHCH_2CH_2NH_2$, OH, or $NH_2$; and each $X^3$ is independently O, NH, N($C_1$-$C_3$ alkyl), or S;

or a pharmaceutically acceptable salt thereof.

2. A compound according to claim 1, wherein $R^2$ is H and Hal is Cl.

3. A compound according to claim 1, wherein $R^3$ is

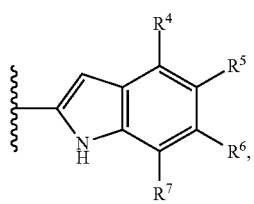

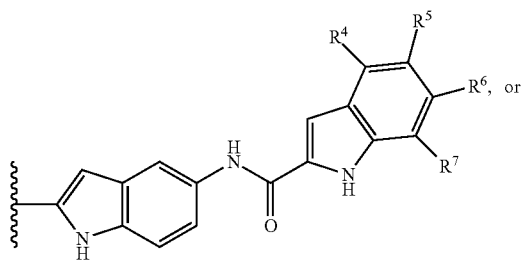

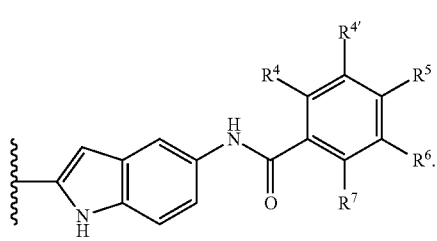

4. A compound according to claim 1, having a structure represented by formula (Ia):

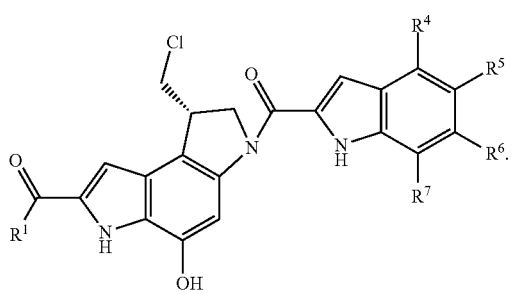

5. A compound according to claim 4, wherein $R^4$, $R^6$, and $R^7$ are each H, $R^1$ is

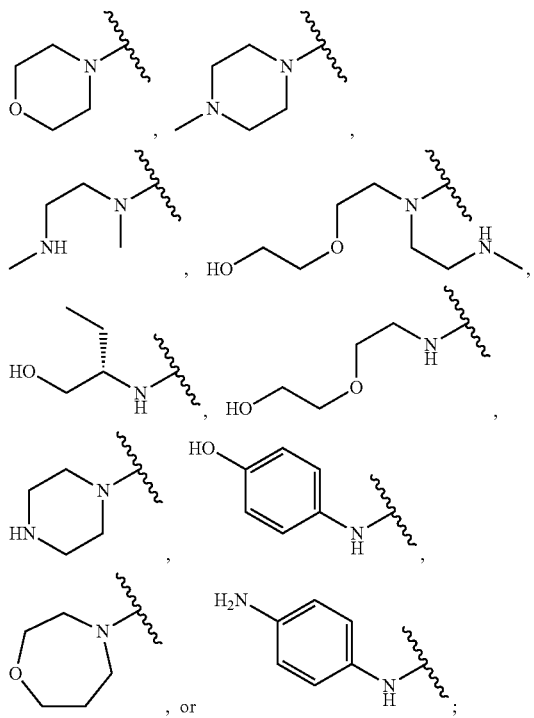

and $R^5$ is

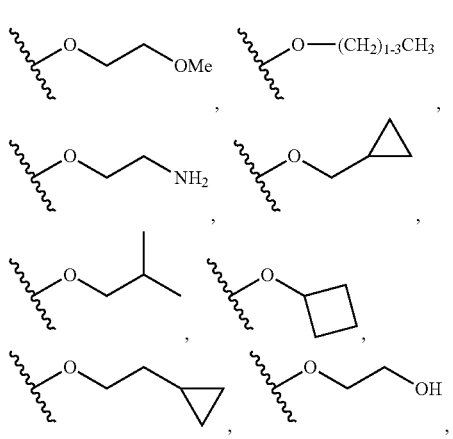

-continued

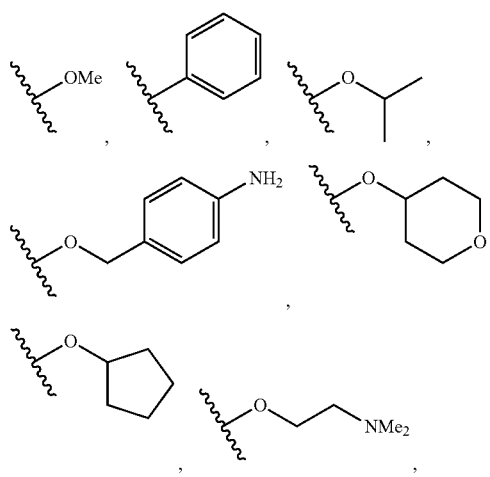

9. A compound according to claim 1, having a structure represented by formula (Ic):

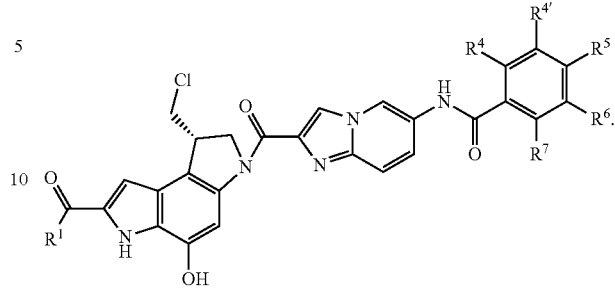

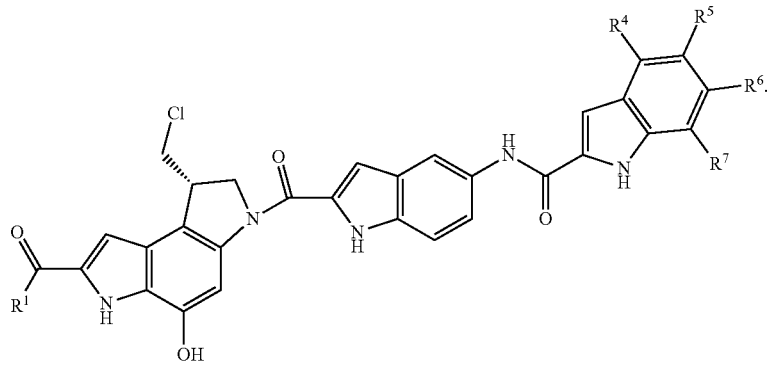

10. A compound according to claim 1, having a structure represented by formula (Id):

-continued

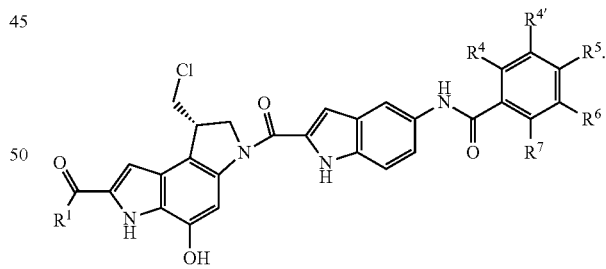

6. A compound according to claim 1, wherein R¹ is a group whose corresponding compound R¹H has a CLogP value of less than 0.300.

7. A compound according to claim 4, wherein R¹ is

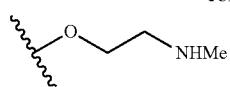

11. A method of treating a cancer in a subject suffering from such cancer, comprising administering to the subject a therapeutically effective amount of a compound according to claim 1 or a conjugate thereof with an antibody, wherein the cancer is selected from lung cancer, gastric cancer, ovarian cancer, or colon cancer.

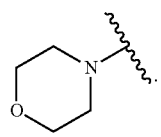

8. A compound according to claim 1, having a structure represented by formula (Ib):

12. A compound according to claim 7, selected from the group consisting of

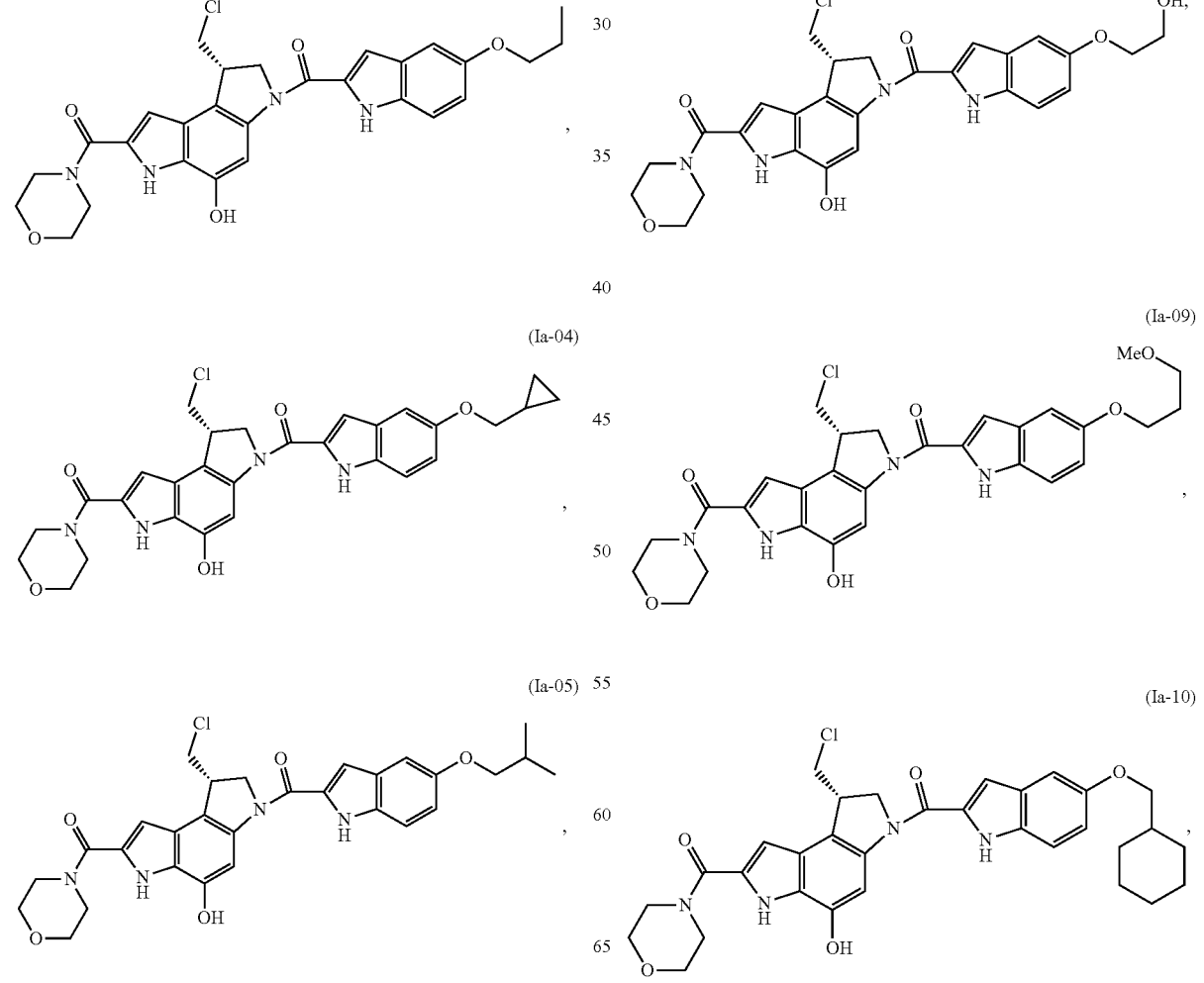

(Ia-11) 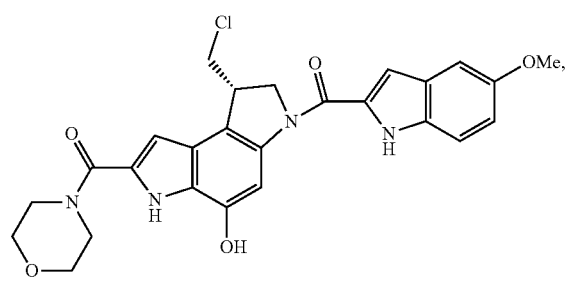
(Ia-12) 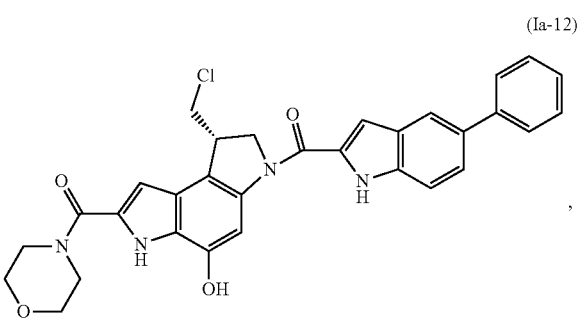
(Ia-13) 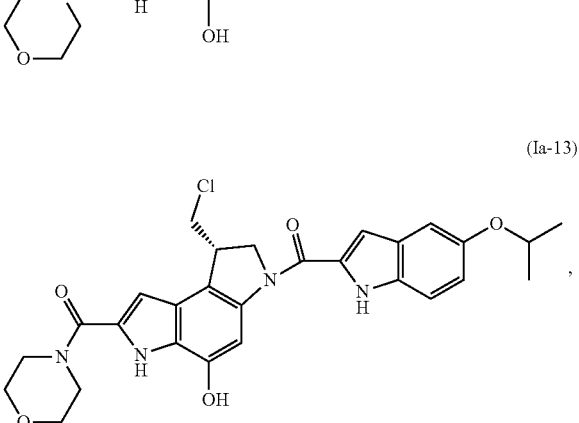
(Ia-14) 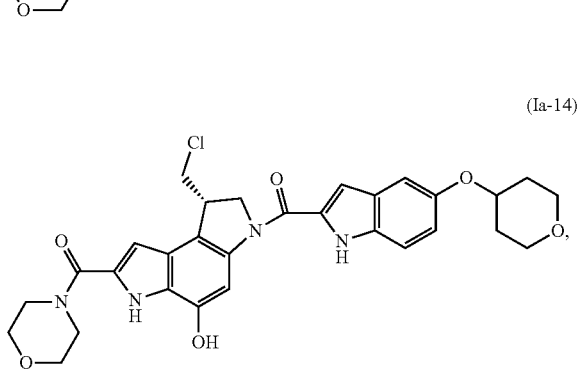
(Ia-15) 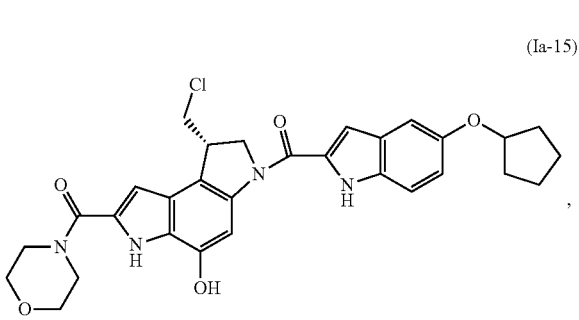
(Ia-16) 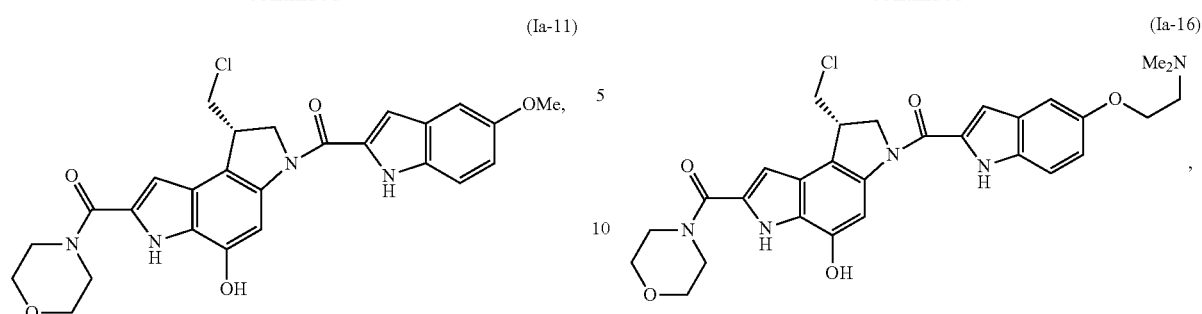
(Ia-17) 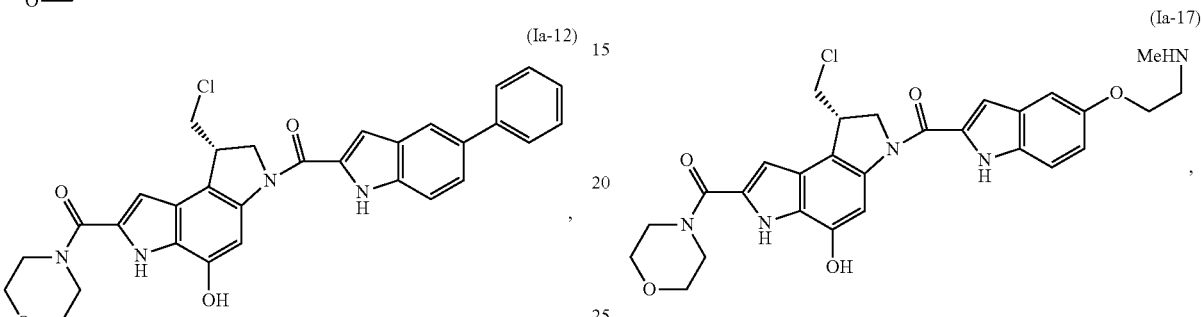
(Ia-18) 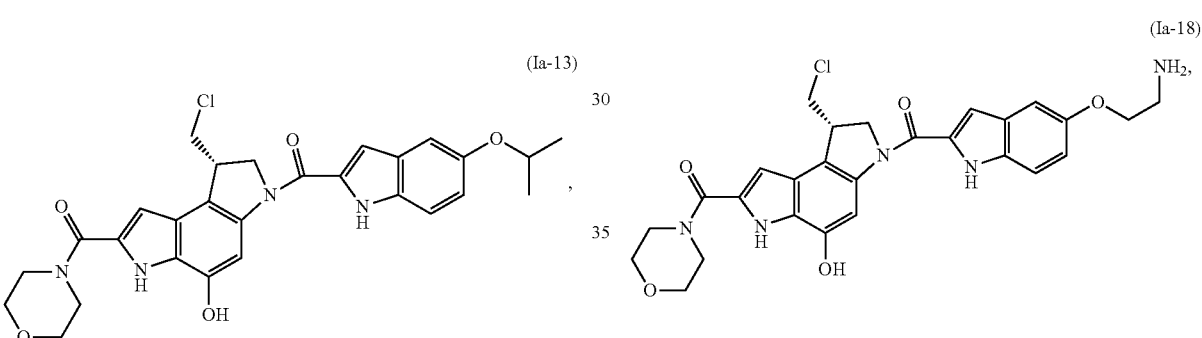
(Ia-19) 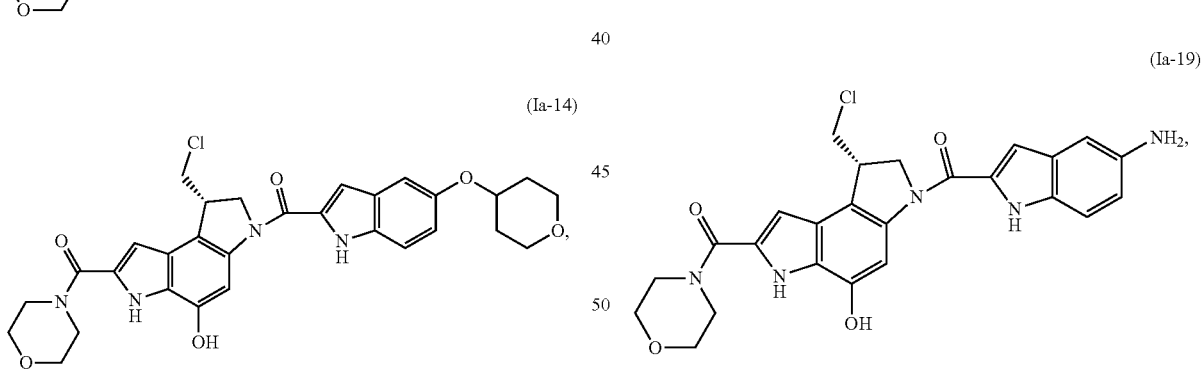
(Ia-20) 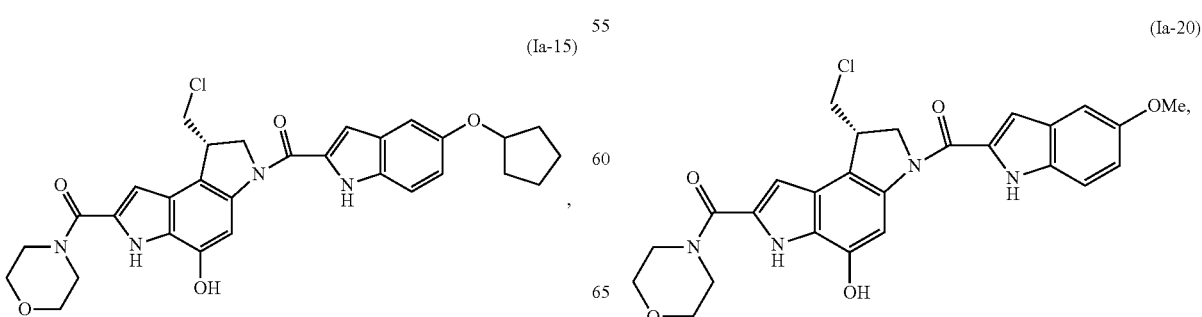

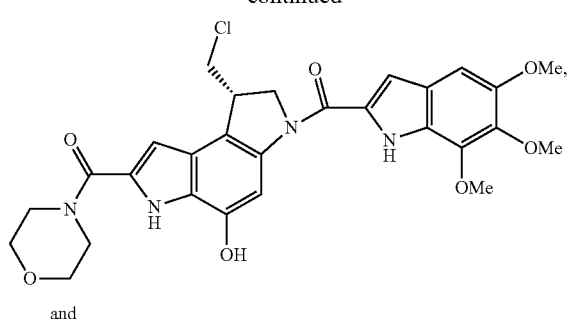
and
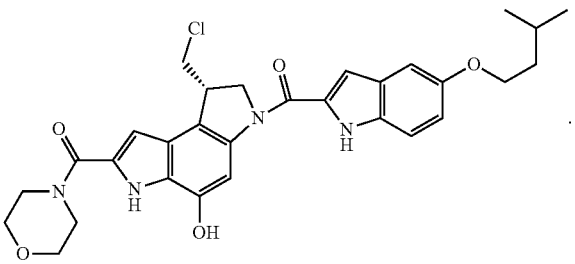
13. A compound according to claim 7, having a structure represented by formula (Ia-01):
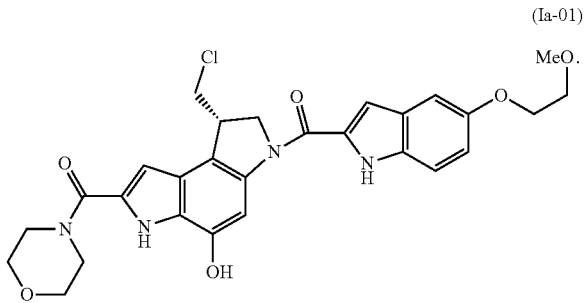 [SMILES: COCCOc1ccc2[nH]c(C(=O)N3C[C@@H](CCl)c4c3cc(O)c3[nH]c(C(=O)N5CCOCC5)cc43)cc2c1]
* * * * *